(12) United States Patent
Blake et al.

(10) Patent No.: US 8,372,842 B2
(45) Date of Patent: *Feb. 12, 2013

(54) PYRAZOLOPYRIDINES AS KINASE INHIBITORS

(75) Inventors: James F. Blake, Boulder, CO (US); Indrani W. Gunawardana, Boulder, CO (US); Yvan Le Huerou, Boulder, CO (US); Peter J. Mohr, Boulder, CO (US); Eli M. Wallace, Boulder, CO (US); Bin Wang, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/812,448

(22) PCT Filed: Jan. 8, 2009

(86) PCT No.: PCT/US2009/030450
§ 371 (c)(1),
(2), (4) Date: Jul. 9, 2010

(87) PCT Pub. No.: WO2009/089359
PCT Pub. Date: Jul. 16, 2009

(65) Prior Publication Data
US 2010/0280043 A1    Nov. 4, 2010

Related U.S. Application Data

(60) Provisional application No. 61/019,865, filed on Jan. 9, 2008.

(51) Int. Cl.
*A61K 31/496* (2006.01)
*C07D 471/04* (2006.01)
(52) U.S. Cl. .................. 514/253.04; 544/362
(58) Field of Classification Search .............. None
See application file for complete search history.

(56) References Cited

U.S. PATENT DOCUMENTS

| | | | |
|---|---|---|---|
| 6,423,716 B1 | 7/2002 | Matsuno et al. |
| 6,627,628 B1 | 9/2003 | Schindler et al. |
| 7,115,741 B2 | 10/2006 | Levy et al. |
| 7,968,545 B2 | 6/2011 | Wilson et al. |
| 7,994,172 B2 | 8/2011 | Rice et al. |
| 8,003,651 B2 | 8/2011 | Mitchell et al. |
| 8,063,050 B2 | 11/2011 | Mitchell et al. |
| 8,076,338 B2 | 12/2011 | Anand et al. |
| 8,178,131 B2 | 5/2012 | Le Huerou et al. |
| 2003/0162785 A1 | 8/2003 | Lin et al. |
| 2004/0053933 A1 | 3/2004 | Pontillo et al. |
| 2005/0130954 A1 | 6/2005 | Mitchell et al. |
| 2005/0256157 A1 | 11/2005 | Gesner et al. |
| 2007/0027156 A1 | 2/2007 | Nakai et al. |
| 2007/0082900 A1 | 4/2007 | Guzi et al. |
| 2007/0135466 A1 | 6/2007 | Ledeboer et al. |
| 2009/0099213 A1 | 4/2009 | Berdini et al. |
| 2009/0111850 A1 | 4/2009 | Linsell et al. |
| 2009/0124610 A1 | 5/2009 | Saxty et al. |
| 2010/0210639 A1 | 8/2010 | Collins et al. |
| 2010/0260868 A1 | 10/2010 | Humphries et al. |
| 2010/0292244 A1 | 11/2010 | Bencsik et al. |
| 2010/0324041 A1 | 12/2010 | Blake et al. |
| 2011/0015204 A1 | 1/2011 | Bencsik et al. |
| 2011/0065716 A1 | 3/2011 | Bencsik et al. |
| 2011/0160221 A1 | 6/2011 | Bencsik et al. |
| 2011/0183933 A1 | 7/2011 | Guzi et al. |
| 2011/0245230 A1 | 10/2011 | Mitchell et al. |
| 2011/0251181 A1 | 10/2011 | Banka et al. |
| 2011/0269773 A1 | 11/2011 | Mitchell et al. |
| 2012/0040935 A1 | 2/2012 | Wilson et al. |

FOREIGN PATENT DOCUMENTS

| | | |
|---|---|---|
| WO | WO 03/028724 A1 | 4/2003 |
| WO | 2005/051304 | * 6/2005 |
| WO | WO 2005/063746 A1 | 7/2005 |
| WO | WO 2005/103036 A1 | 11/2005 |
| WO | WO 2006/077319 A1 | 7/2006 |
| WO | WO 2006/106326 A1 | 10/2006 |
| WO | WO 2006/120573 A2 | 11/2006 |

(Continued)

OTHER PUBLICATIONS

Bartek et al. Cancer Cell, vol. 3, p. 421-429 (2003).*

(Continued)

*Primary Examiner* — Emily Bernhardt
(74) *Attorney, Agent, or Firm* — Viksnins Harris & Padys PLLP

(57) ABSTRACT

Compounds of Formula I are useful for inhibition of CHK1 and/or CHK2. Methods of using compounds of Formula I and stereoisomers and pharmaceutically acceptable salts thereof, for in vitro, in situ, and in vivo diagnosis, prevention or treatment of such disorders in mammalian cells, or associated pathological conditions are disclosed.

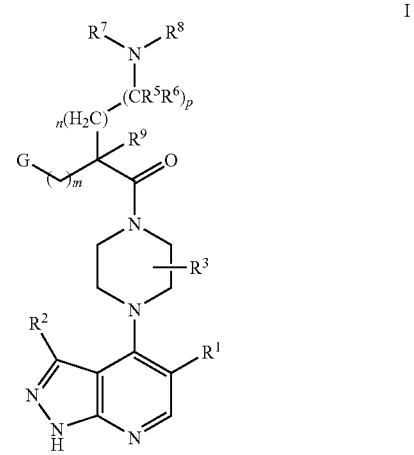

53 Claims, No Drawings

FOREIGN PATENT DOCUMENTS

| | | |
|---|---|---|
| WO | WO 2006/130673 A1 | 12/2006 |
| WO | WO 2007/002433 A1 | 1/2007 |
| WO | WO 2007/059219 A1 | 5/2007 |
| WO | WO 2007/090493 A1 | 8/2007 |
| WO | WO 2007/090494 A1 | 8/2007 |
| WO | WO 2007/103308 A2 | 9/2007 |
| WO | WO 2007/125321 A2 | 11/2007 |
| WO | WO 2008/006039 A1 | 1/2008 |
| WO | WO 2008/012635 A2 | 1/2008 |
| WO | WO 2008/075007 A1 | 6/2008 |
| WO | WO 2010/118390 A1 | 10/2010 |
| WO | WO 2012/074754 A1 | 6/2012 |

OTHER PUBLICATIONS

Antoni et al. Nature Reviews/Cancer vol. 7, p. 925-936 (2007).*

Ahn, et al., "The Chk2 protein kinase", *DNA Repair 3*, 1039-1047 (2004).

Arrington et al. "Novel Inhibitors of Checkpoint Kinase 1", *CHEMEDCHEM*, vol. 2, 1571-1585 (2007).

Bartek, et al., "CHK2 Kinase—A Busy Messenger", *Nature Reviews Molecular Cell Biology*, vol. 2 (12), 877-886 (2001).

Foloppe et al., "Identification of a buried pocket for potent and selective inhibition of Chk1: Prediction and verification", *Bioorganic & Medicinal Chemistry 14*, 1792-1804 (2006).

Foloppe et al., "Structure-Based Design of Novel Chk1 Inhibitors: Insights into Hydrogen Bonding and Protein—Ligand Affinity", *J. Med. Chem. 48*, 4332-4345 (2005).

Janetka, et al., "Inhibitors of checkpoint kinases: From discovery to the clinic", *Drug Discovery & Development*, vol. 10, No. 4, 473-486 (2007).

Li et al., "Targeting Serine/Threonine Protein Kinase B/Akt and Cell-cycle Checkpoint Kinases for Treating Cancer", *Current Topics in Medicinal Chemistry*, 2, 939-971 (2002).

Patent Cooperation Treaty, International Search Report and Written Opinion for PCT/US2009/030450, 14 pages, Mar. 17, 2009.

Pommier et al., "Targeting Chk2 Kinase: Molecular Interaction Maps and Therapeutic Rationale", *Current Pharmaceutical Design vol. 11*, No. 22, 2855-2872 (2005).

Reader et al., "Identification and Structure-guided Optimisation of Novel Inhibitors of Checkpoint Kinase 1 (Chk1) through Combined Biochemical and Crystallographic Screening", *AACR, Poster, Abstract 757, Sareum Ltd, UK, Cancer Research UK Centre for Cancer Therapeutics, and The Institute of Cancer Research, UK*, 1 page.

Tao et al., "Chk1 Inhibitors for Novel Cancer Treatment", *Anti-Cancer Agents in Medicinal Chemistry*, 6, 377-388 (2006).

Tse et al., "Targeting Checkpoint Kinase 1 in Cancer Therapeutics", *Clin. Cancer Res. 13* (7), 1955-1960 (2007).

Wang et al., "1-(5-Chloro-2-alkoxyphenyl)-3-(5-cyanopyrazin-2-l)ureas as potent and selective inhibitors of Chk1 kinase: synthesis, preliminary SAR, and biological activities", *Journal of Medicinal Chemistry, American Chemical Society*, vol. 48, No. 9, 3118-3121, XP002456672 (2005).

* cited by examiner

PYRAZOLOPYRIDINES AS KINASE INHIBITORS

RELATED APPLICATIONS

This application claims priority to U.S. Provisional Application No. 61/019,865 that was filed on Jan. 9, 2008.

BACKGROUND OF THE INVENTION

1. Field of the Invention

The present invention relates to novel compounds, to pharmaceutical compositions comprising the compounds, to a process for making the compounds and to the use of the compounds in therapy. More particularly it relates to certain 4-substituted 1H-pyrazolo[3,4-b]pyridines useful in the treatment and prevention of hyperproliferative diseases.

2. Description of the State of the Art

Protein kinases are kinase enzymes that phosphorylate other proteins. The phosphorylation of these proteins usually produces a functional change in the protein. Most kinases act on serine and threonine or tyrosine, and some kinases act on all three. Through these functional changes, kinases can regulate many cellular pathways. Protein kinase inhibitors are compounds that inhibit these protein kinases, and thus can be used to affect cellular pathways.

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al, "Targeting Checkpoint Kinase 1 in Cancer Therapeutics." *Clin. Cancer Res.* 13(7) (2007)1955-1960). It has been observed that many tumors are deficient in the $G_1$ DNA damage checkpoint pathway, resulting in the reliance on S and $G_2$ checkpoints to repair DNA damage and survive. (Janetka, James W., et al., "Inhibitors of checkpoint kinases: From discovery to the clinic." *Drug Discovery & Development* Vol. 10, No. 4 (2007)473-486). The S and $G_2$ checkpoints are regulated by CHK1. Inhibition of CHK1 has been shown to cancel the S and $G_2$ checkpoints, thereby impairing DNA repair and resulting in increased tumor cell death. However, non-cancerous cells have a functioning $G_1$ checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al, "The Chk2 protein kinase." *DNA Repair* 3 (2004) 1039-1047). CHK2 is activated in response to genotoxic insults and propagates the checkpoint signal along several pathways, which eventually causes cell-cycle arrest in the $G_1$, S and $G_2$/M phases, activation of DNA repair, and apoptotic cell death. (Bartek, Jiri, et al., "CHK2 Kinase—A Busy Messenger." *Nature Reviews Molecular Cell Biology* Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs. Normal cells would still activate other checkpoints and recover, while cancer cells deprived of checkpoints would be more likely to die. It has been demonstrated that a peptide-based inhibitor of CHK2 abrogated the G2 checkpoint and sensitized p53-defective cancer cells to DNA damaging agents. (Pommier, Yves, et al., "Targeting Chk2 Kinase: Molecular Interaction Maps and Therapeutic Rationale." *Current Pharmaceutical Design* Vol. 11, No. 22 (2005)2855-2872).

CHK1 and/or CHK2 inhibitors are known, see for example, International Publication Number WO 2007/090493, International Publication Number WO 2007/090494, International Publication WO 2006/106326, International Publication WO 2005/103036 and International Publication WO 03/028724.

Certain pyrazolopyridines are known, but not as CHK1/2 inhibitors, see for example, International Publication Number WO 2007/103308, International Publication Number WO 2007/073199, International Publication Number WO 2007/059219, International Publication WO 2006/130673, International Publication WO 2006/077319 and International Publication WO 2005/051304.

SUMMARY OF THE INVENTION

In one aspect, the present invention relates to compounds that are inhibitors of CHK1 and/or CHK2. Accordingly, the compounds of the present invention are useful in the treatment of diseases and conditions that can be treated by the inhibition of CHK1 and/or CHK2 protein kinases.

More specifically, one aspect of the present invention provides compounds of Formula I:

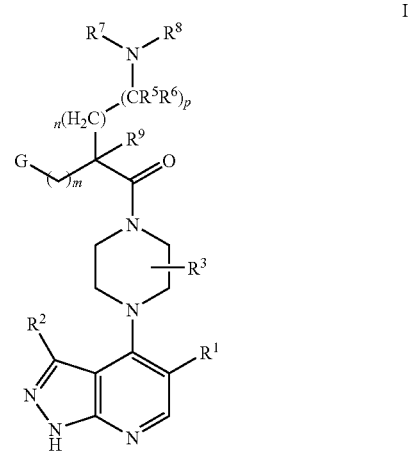

and stereoisomers and pharmaceutically acceptable salts thereof, wherein G, $R^1$, $R^2$, $R^3$, $R^5$, $R^6$, $R^7$, $R^8$, $R^9$, m, n, and p are as defined herein.

More specifically, one aspect of the present invention provides compounds of Formula I:

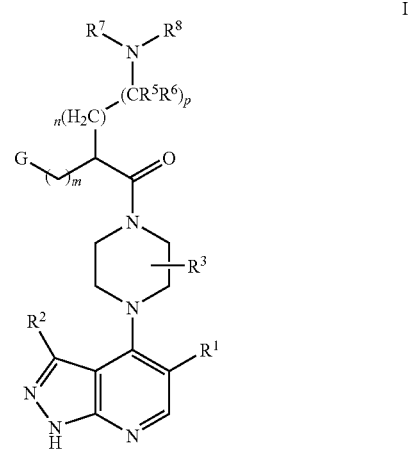

and stereoisomers and pharmaceutically acceptable salts thereof, wherein G, $R^1$, $R^2$, $R^3$, $R^5$, $R^6$, $R^7$, $R^8$, m, n, and p are as defined herein.

Another aspect of the present invention provides methods of preventing or treating a disease or disorder modulated by CHK1 and/or CHK2, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer), neurodegeneration, cardiac hypertrophy, pain, migraine and neurotraumatic disease.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

Another aspect of the present invention provides a method of treating a hyperproliferative disease in a mammal comprising administering a therapeutically effective amount of a compound of this invention to the mammal.

Another aspect of the present invention provides the compounds of this invention for use in therapy.

Another aspect of the present invention provides the compounds of this invention for use in the treatment of a hyperproliferative disease.

Another aspect of the present invention provides the use of a compound of this invention in the manufacture of a medicament, for use as a CHK1 and/or CHK2 inhibitor in the treatment of a patient undergoing cancer therapy.

Another aspect of the present invention provides a pharmaceutical composition comprising a compound of this invention or a pharmaceutically acceptable salt thereof, and a pharmaceutically acceptable carrier or excipient.

Another aspect of the present invention provides a pharmaceutical composition comprising a compound of the present invention for use in the treatment of a hyperproliferative disease.

Another aspect of the present invention provides a pharmaceutical composition comprising a compound of the present invention for use in the treatment of cancer.

Another aspect of the present invention includes methods of preparing, methods of separation, and methods of purification of the compounds of this invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations used throughout the application include benzyl ("Bn") and phenyl ("Ph").

The term "heteroaryl" includes 5 to 6 membered aromatic rings containing one, two or three heteroatoms selected from the group consisting of oxygen, nitrogen and sulfur.

The term "heterocycle" includes 5 to 6 membered rings containing one, two or three heteroatoms selected from the group consisting of oxygen, nitrogen and sulfur.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer, including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancers, including melanoma, as well as head and neck cancer.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

CHK1/2 Inhibitor Compounds

The present invention provides certain 4-substituted 1H-pyrazolo[3,4-b]pyridines that are CHK1 and/or CHK2 inhibitors useful in the treatment of diseases, conditions and/or disorders modulated by CHK1 and/or CHK2.

It has surprisingly been found that 4-substituted 1H-pyrazolo[3,4-b]pyridines having particular substituents at the 3 and/or 5 positions are inhibitors of CHK1 and/or CHK2. Furthermore, some of these compounds have been found to be selective for CHK1 over certain other protein kinases.

Accordingly, the present invention provides compounds of Formula I:

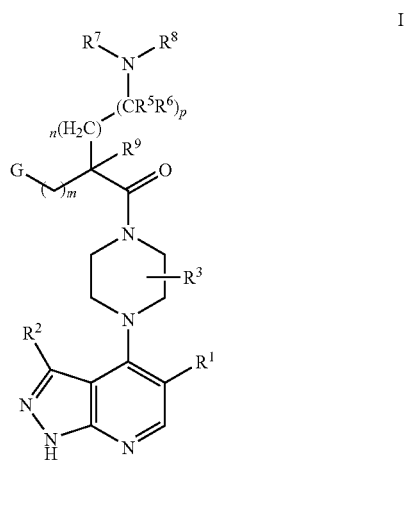

and stereoisomers and pharmaceutically acceptable salts thereof, wherein:

G is phenyl optionally substituted by 1-3 independent $R^4$ groups, or when m is 0, G may additionally be absent or $C_1$-$C_4$ alkyl;

$R^1$ is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$, $CH_2CH_3$, $CF_3$, $C_2$-$C_4$ alkenyl optionally substituted with one or two $R^c$ groups, $NHR^a$ or —$OR^f$, provided that when $R^1$ is hydrogen, then $R^2$ is —$OR^f$;

$R^3$ is selected from hydrogen or $C_1$-$C_4$ alkyl;

each $R^4$ is independently selected from halogen, $CF_3$, $OCF_3$ and CN;

$R^5$ and $R^6$ are independently selected from hydrogen or $CH_3$;

$R^7$ and $R^8$ are independently selected from hydrogen or $C_1$-$C_6$ alkyl;

$R^9$ is hydrogen or $CH_3$;

$R^a$ is hydrogen or a five to six membered heterocycle optionally substituted with an oxo group;

$R^b$ is halogen;

$R^c$ is OH, $OCH_3$, oxo, or a 5 to 6 membered heteroaryl;

$R^e$ is is $C_1$-$C_4$ alkyl optionally substituted with OH or a 5-6 membered heterocycle;

$R^f$ is $C_1$-$C_4$ alkyl optionally substituted with one or more OH groups;

m, n and p are independently 0 or 1;

or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl), such that the compound of Formula I has the structure of Formula II:

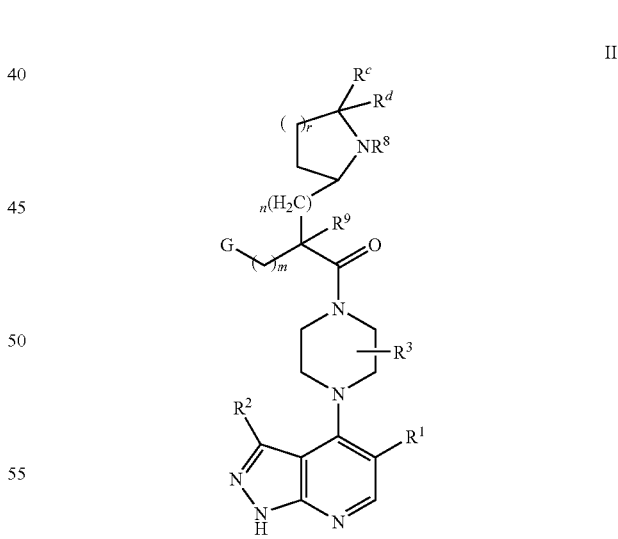

wherein $R^c$ and $R^d$ are independently selected from hydrogen or $C_1$-$C_4$ alkyl; and r is 1 or 2.

Accordingly, the present invention provides compounds of Formula I:

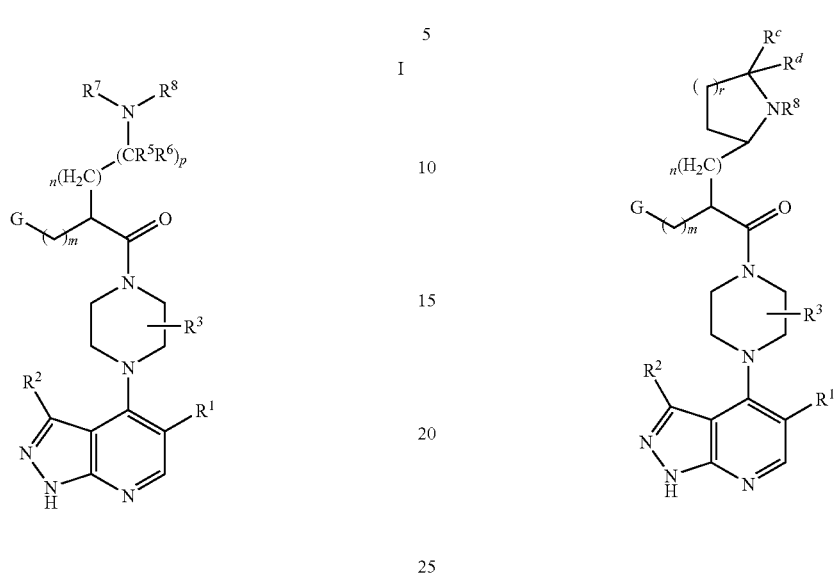

and stereoisomers and pharmaceutically acceptable salts thereof, wherein:

G is phenyl optionally substituted by 1-3 independent $R^4$ groups, or when m is 0, G may additionally be absent or $C_1$-$C_4$ alkyl;

$R^1$ is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$ or —$OR^f$, provided that when $R^1$ is hydrogen, then $R^2$ is —$OR^f$;

$R^3$ is selected from hydrogen or $C_1$-$C_4$ alkyl;

each $R^4$ is independently selected from halogen, $CF_3$, $OCF_3$ and CN;

$R^5$ and $R^6$ are independently selected from hydrogen or $CH_3$;

$R^7$ and $R^8$ are independently selected from hydrogen or $C_1$-$C_6$ alkyl;

$R^b$ is halogen;

$R^e$ is is $C_1$-$C_4$ alkyl optionally substituted with OH or a 5-6 membered heterocycle;

$R^f$ is $C_1$-$C_4$ alkyl optionally substituted with one or more OH groups;

m, n and p are independently 0 or 1;

or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl), such that the compound of Formula I has the structure of Formula II:

wherein $R^c$ and $R^d$ are independently selected from hydrogen or $C_1$-$C_4$ alkyl; and r is 1 or 2.

In certain embodiments, G is phenyl optionally substituted by one to three $R^4$ groups. In certain embodiments, G is phenyl substituted by one $R^4$ group. In certain embodiments, G is phenyl substituted by chlorine. In particular embodiments, G is 4-chlorophenyl.

Referring to the G group of Formula I, examples include phenyl optionally substituted with one or more $R^4$ groups independently selected from halogen, $CF_3$, $OCF_3$ and CN.

In certain embodiments, m is 0 and G is phenyl optionally substituted by 1-3 independent $R^4$ groups, absent or $C_1$-$C_4$ alkyl.

In certain embodiments, m is 0 and G is absent, provided that when G is absent, $R^2$ is —$OR^f$.

In certain embodiments, $R^1$ is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is selected from hydrogen, Br, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is selected from hydrogen, halogen, CN, $C_1$-$C_4$ alkyl optionally substituted with halogen, —$OR^e$, $C_3$-$C_6$ cycloalkyl, phenyl or —O-phenyl, wherein the phenyl or —O-phenyl may be optionally substituted with one or two $R^b$ groups.

In certain embodiments, $R^1$ is selected from hydrogen, Br, CN, $C_1$-$C_4$ alkyl optionally substituted with halogen, —$OR^e$, $C_3$-$C_6$ cycloalkyl, phenyl or —O-phenyl, wherein the phenyl or —O-phenyl may be optionally substituted with one or two $R^b$ groups.

In certain embodiments, $R^1$ is selected from hydrogen, CN, $C_1$-$C_4$ alkyl optionally substituted with halogen, —$OR^e$, $C_3$-$C_6$ cycloalkyl, phenyl or —O-phenyl, wherein the phenyl or —O-phenyl may be optionally substituted with one or two $R^b$ groups.

In certain embodiments, $R^1$ is selected from halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is selected from CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups.

In certain embodiments, $R^1$ is CN.

In certain embodiments, $R^1$ is $C_1$-$C_4$ alkyl.

In certain embodiments, $R^1$ is $C_1$-$C_4$ alkyl optionally substituted with halogen. In certain embodiments, $R^1$ is $CF_3$.

In certain embodiments, $R^1$ is —$OR^e$. In certain embodiments, $R^e$ is is $C_1$-$C_4$ alkyl optionally substituted with OH or a 5-6 membered heterocycle.

In certain embodiments, $R^e$ is $C_1$-$C_4$ alkyl optionally substituted with a 5-6 membered heterocycle. In certain embodiments, $R^e$ is morpholinyl.

In certain embodiments, $R^1$ is $C_3$-$C_6$ cycloalkyl.

In certain embodiments, $R^1$ is cyclopropyl.

In certain embodiments, $R^1$ is phenyl optionally substituted with one or two $R^b$ groups. In certain embodiments, $R^b$ is halogen.

In certain embodiments, $R^1$ is phenyl. In certain embodiments, $R^2$ is hydrogen or methyl.

In certain embodiments, $R^1$ is phenyl substituted with one $R^b$ group. In certain embodiments, $R^b$ is halogen. In certain embodiments, $R^1$ is phenyl substituted with F.

In certain embodiments, $R^1$ is phenyl substituted by at least one $R^b$ group at the 3-phenyl position. In certain embodiments, $R^1$ is 3-fluorophenyl.

In certain embodiments, $R^1$ is —O-phenyl (phenoxy), optionally substituted with one or two $R^b$ groups. In certain embodiments, $R^1$ is —O-phenyl substituted with one $R^b$ group. In certain embodiments, $R^1$ is 3-fluorophenoxy.

In certain embodiments, $R^1$ is halogen.

In certain embodiments, $R^1$ is Br.

In certain embodiments, $R^1$ is Cl.

In certain embodiments, $R^1$ is I.

In certain embodiments, $R^1$ is $C_1$-$C_4$ alkyl. In certain embodiment, $R^1$ is methyl.

In certain embodiments, $R^1$ is hydrogen, provided that when $R^1$ is hydrogen, then $R^2$ is —$OR^f$.

In certain embodiments, $R^1$ is hydrogen, provided that when $R^1$ is hydrogen, then $R^2$ is —$OR^f$ and $R^f$ is $C_2$-$C_4$ alkyl optionally substituted with one or more OH groups.

In certain embodiments, $R^2$ is selected from hydrogen, $CH_3$, $CH_2CH_3$, $CF_3$, $C_2$-$C_4$ alkenyl optionally substituted with one or two $R^c$ groups, $NHR^a$ or —$OR^f$, provided that when $R^1$ is hydrogen, then $R^2$ is —$OR^f$.

In certain embodiments, $R^2$ is hydrogen.

In certain embodiments, $R^2$ is selected from $CH_3$, $CH_2CH_3$ and $CF_3$.

In certain embodiments, $R^2$ is $C_2$-$C_4$ alkenyl optionally substituted with one or two $R^c$ groups. In certain embodiments, $R^c$ is OH, $OCH_3$, oxo, or a 5 to 6 membered heteroaryl. In certain embodiments, $R^c$ is a 5 to 6 membered heteroaryl containing one or two nitrogen heteroatoms. In certain embodiments, $R^c$ is a 5 to six membered heteroaryl, wherein the heteroaryl is selected from pyrazole and pyridine. In certain embodiments, $R^2$ is selected from —CH=CHC(=O)$OCH_3$, 2-(pyridin-3-yl)vinyl, and 2-(1H-pyrazol-4-yl)vinyl.

In certain embodiments, $R^2$ is $NHR^a$. In certain embodiments, $R^a$ is hydrogen or a five to six membered heterocycle optionally substituted with an oxo group. In certain embodiments, $R^a$ is a five to six membered heterocycle having one nitrogen heteroatom. In certain embodiments, $R^a$ is a five to six membered heterocycle, wherein the heterocycle is pyrrolidine. In certain embodiments, $R^2$ is selected from $NH_2$ and NH-4-pyrrolidin-2-one.

In certain embodiments, $R^2$ is —$OR^f$.

In certain embodiments, $R^f$ is $C_1$-$C_4$ alkyl optionally substituted with one or more OH groups.

In certain embodiments, $R^f$ is $C_2$-$C_4$ alkyl optionally substituted with one or more OH groups.

In certain embodiments, $R^f$ is $C_1$-$C_4$ alkyl. In certain embodiments, $R^2$ is —$OCH_3$.

In certain embodiments, $R^f$ is $C_1$-$C_4$ alkyl optionally substituted with one or more OH groups. In certain embodiments, $R^f$ is $C_1$-$C_4$ alkyl substituted with one OH group.

In certain embodiments, $R^2$ is —$OCH_2CH_2OH$.

In certain embodiments, $R^f$ is $C_1$-$C_4$ alkyl optionally substituted with one or more OH groups. In certain embodiments, $R^f$ is $C_1$-$C_4$ alkyl substituted with two OH groups.

In certain embodiments, $R^2$ is —$OCH_2CH(OH)CH_2OH$.

In certain embodiments, $R^3$ is hydrogen.

In certain embodiments, m is 0 or 1. In certain embodiments, m is 0. In certain embodiments, m is 1.

In certain embodiments, $R^4$ is a halogen. In a further embodiment, $R^4$ is Cl.

In certain embodiments, n is 0 or 1. In certain embodiments, n is 0. In certain embodiments, n is 1.

In certain embodiments, p is 0 or 1. In certain embodiments, p is 0. In certain embodiments, p is 1.

In certain embodiments, $R^5$ and $R^6$ are independently selected from hydrogen or $CH_3$.

In certain embodiments, $R^5$ and $R^6$ are hydrogen.

In certain embodiments, $R^7$ and $R^8$ are independently selected from hydrogen or $C_1$-$C_6$ alkyl.

In certain embodiments, $R^7$ and $R^8$ are hydrogen.

In certain embodiments, $R^7$ is $C_1$-$C_6$ alkyl. In a further embodiment, $R^7$ is a $C_3$ alkyl. In a further embodiment, $R^7$ is an isopropyl group. In certain embodiments, $R^8$ is hydrogen.

In certain embodiments, $R^8$ is hydrogen.

In certain embodiments, $R^9$ is hydrogen or $CH_3$.

In certain embodiments, $R^9$ is hydrogen.

In certain embodiments, $R^9$ is $CH_3$.

In certain embodiments, $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl), such that the compound of Formula I has the structure of Formula II:

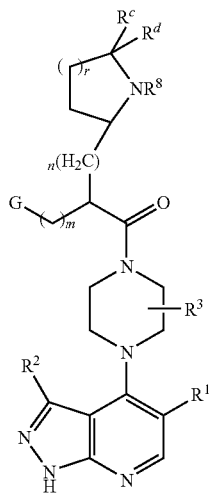

II wherein $R^1$, $R^2$, $R^3$, $R^c$, $R^d$, G, m, n and r are as defined herein.

In certain embodiments of Formula II, r is 1.
In certain embodiments of Formula II, $R^8$ is hydrogen.
In certain embodiments of Formula II, $R^c$ is hydrogen.
In certain embodiments of Formula II, $R^d$ is hydrogen.
In certain embodiments of Formula II, $R^c$ and $R^d$ are hydrogen.
In certain embodiments of Formula II, $R^c$ is methyl.
In certain embodiments of Formula II, $R^d$ is methyl.
In certain embodiments of Formula II, $R^c$ and $R^d$ are methyl.

In certain embodiments, r is 1 (having the structure of Formula IIa):

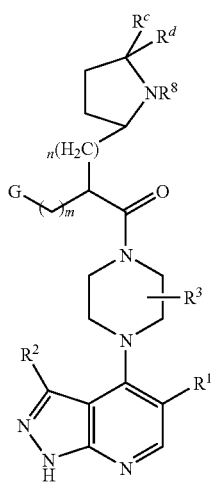

IIa wherein $R^1$, $R^2$, $R^3$, $R^c$, $R^d$, G, m and n are as defined herein.
In certain embodiments of Formula IIa, $R^8$ is hydrogen.
In certain embodiments of Formula IIa, $R^c$ is hydrogen.
In certain embodiments of Formula IIa, $R^d$ is hydrogen.
In certain embodiments of Formula IIa, $R^c$ and $R^d$ are hydrogen.
In certain embodiments of Formula IIa, $R^c$ is methyl.
In certain embodiments of Formula IIa, $R^d$ is methyl.
In certain embodiments of Formula IIa, $R^c$ and $R^d$ are methyl.

In certain embodiments of Formula IIa, n is 0, providing compounds of Formula IIa1:

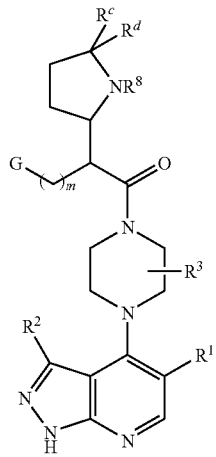

IIa1 wherein $R^1$, $R^2$, $R^3$, $R^c$, $R^d$, G and m are as defined herein.
In certain embodiments of Formula IIa1, $R^8$ is hydrogen.
In certain embodiments of Formula IIa1, $R^c$ is hydrogen.
In certain embodiments of Formula IIa1, $R^d$ is hydrogen.
In certain embodiments of Formula IIa1, $R^c$ and $R^d$ are hydrogen.
In certain embodiments of Formula IIa1, $R^c$ is methyl.
In certain embodiments of Formula IIa1, $R^d$ is methyl.
In certain embodiments of Formula IIa1, $R^c$ and $R^d$ are methyl.

In certain embodiments, r is 2 (having the structure of Formula IIb):

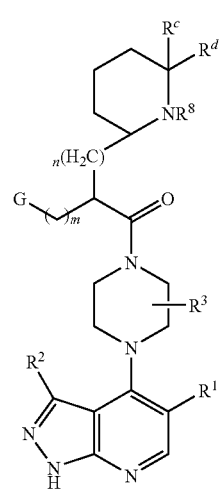

IIb wherein $R^1$, $R^2$, $R^3$, $R^c$, $R^d$, G, m and n are as defined herein.

In certain embodiments of Formula IIb, n is 0, providing the structure of Formula IIb1:

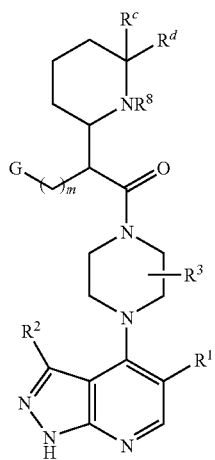

IIb1 wherein $R^1$, $R^2$, $R^3$, $R^c$, $R^d$, G and m are as defined herein.

In certain embodiments, Formula I has the structure of Formula III:

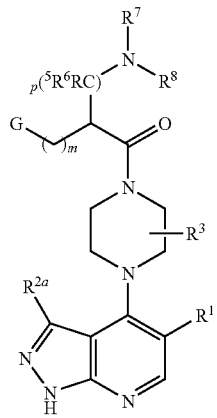

III wherein $R^{2a}$ is hydrogen or methyl, and $R^1$, $R^3$, $R^5$, $R^6$, $R^7$, $R^8$, G, m and p are as defined herein.

In certain embodiments of Formula III, $R^{2a}$ is hydrogen.
In certain embodiments of Formula III, $R^{2a}$ is methyl.
In certain embodiments of Formula III, $R^1$ is phenyl.
In certain embodiments of Formula III, $R^1$ is phenyl substituted with one $R^b$ group. In certain embodiments of Formula III, $R^b$ is halogen. In certain embodiments of Formula III, $R^1$ is phenyl substituted with F.
In certain embodiments of Formula III, $R^1$ is phenyl substituted by at least one $R^b$ group at the 3-phenyl position. In certain embodiments of Formula III, $R^1$ is 3-fluorophenyl.
In certain embodiments of Formula III, $R^1$ is —O-phenyl (phenoxy), optionally substituted with one or two $R^b$ groups. In certain embodiments of Formula III, $R^1$ is —O-phenyl substituted with one $R^b$ group. In certain embodiments of Formula III, $R^1$ is 3-fluorophenoxy.
In certain embodiments of Formula III, $R^1$ is CN.
In certain embodiments of Formula III, $R^1$ is $CF_3$.
In certain embodiments of Formula III, $R^1$ is Br.

In certain embodiments, Formula I has the structure of Formula IV:

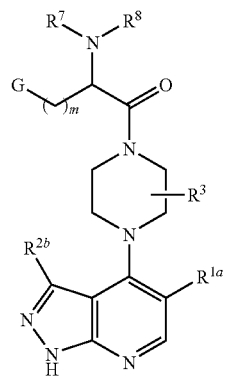

IV wherein $R^{1a}$ is hydrogen, halogen or $C_1$-$C_4$ alkyl optionally substituted with halogen (for example $CF_3$), $R^{2b}$ is —$OR^f$, $R^3$, $R^7$, $R^8$, $R^f$, G and m are as defined herein.

In certain embodiments of Formula IV, $R^{2a}$ is —$OR^f$. In certain embodiments, $R^f$ is $C_1$-$C_4$ alkyl optionally substituted with one or more OH groups.

In certain embodiments of Formula IV, $R^{2a}$ is —$OR^f$. In certain embodiments, $R^f$ is $C_2$-$C_4$ alkyl optionally substituted with one or more OH groups.

In certain embodiments of Formula IV, $R^{2a}$ is —$OCH_2CH_2OH$.

In certain embodiments of Formula IV, $R^{2a}$ is —$OCH_2CH(OH)CH_2OH$.

In certain embodiments of Formula IV, $R^f$ is $C_1$-$C_4$ alkyl optionally substituted with one or more OH groups. In certain embodiments of Formula IV, $R^f$ is $C_1$-$C_4$ alkyl substituted with one OH group. In certain embodiments of Formula IV, $R^{2a}$ is —$OCH_2CH_2OH$.

In certain embodiments of Formula IV, $R^f$ is $C_1$-$C_4$ alkyl optionally substituted with one or more OH groups. In certain embodiments of Formula IV, $R^f$ is $C_1$-$C_4$ alkyl substituted with two OH groups. In certain embodiments of Formula IV, $R^{2a}$ is —$OCH_2CH(OH)CH_2OH$.

In certain embodiments, m is 0 and G is $G^1$, such that the compounds of Formula I have the structure of Formula V:

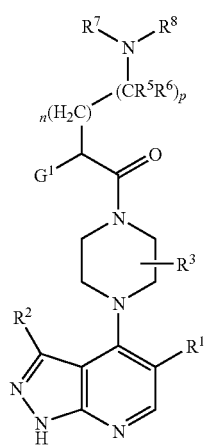

V wherein $G^1$ is absent or $C_1$-$C_4$ alkyl, and $R^1$, $R^2$, $R^3$, $R^5$, $R^6$, $R^7$, $R^8$, n and p are as defined above.

In certain embodiments of Formula V, $R^2$ is —$OR^f$. In certain embodiments, $R^f$ is $C_1$-$C_4$ alkyl optionally substituted with one or more OH groups.

In certain embodiments of Formula V, $R^2$ is —$OR^f$. In certain embodiments, $R^f$ is $C_2$-$C_4$ alkyl optionally substituted with one or more OH groups.

In certain embodiments of Formula V, $R^f$ is $C_1$-$C_4$ alkyl optionally substituted with one or more OH groups.

In certain embodiments of Formula IV, $R^f$ is $C_1$-$C_4$ alkyl substituted with two OH groups.

In certain embodiments of Formula IV, $R^{2b}$ is —$OCH_2CH(OH)CH_2OH$.

In certain embodiments, m and n are 0, $R^5$ is hydrogen, $R^6$ and $R^7$ together with the atoms to which they are attached form an optionally substituted 5-6 membered heterocyclic ring having one ring nitrogen atom, $R^8$ is selected from the group consisting of hydrogen or $C_1$-$C_4$ alkyl optionally substituted with OH or $O(C_1$-$C_3$ alkyl) and G is $G^1$, such that the compounds of Formula I h structure of Formula VI:

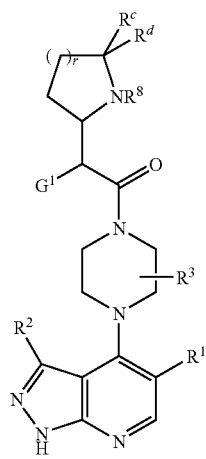

VI wherein $G^1$ is absent or $C_1$-$C_4$ alkyl, and $R^1$, $R^2$, $R^3$, $R^c$, $R^d$ and r are as defined herein.

In certain embodiments, m and n are 0, r is 1, $R^5$ is hydrogen, $R^6$ and $R^7$ together with the atoms to which they are attached form an optionally substituted 5 membered heterocyclic ring having one ring nitrogen atom, $R^8$ is selected from the group consisting of hydrogen or $C_1$-$C_4$ alkyl optionally substituted with OH or $O(C_1$-$C_3$ alkyl) and G is $G^1$, such that the compounds of Formula I have the structure of Formula VIa:

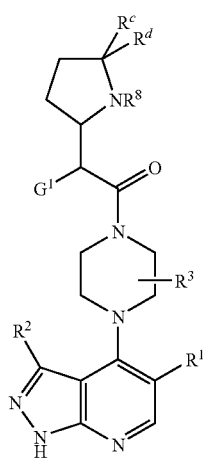

VIa wherein $G^1$ is absent or $C_1$-$C_4$ alkyl, and $R^1$, $R^2$, $R^3$, $R^c$, and $R^d$ are as defined herein.

In certain embodiments, m and n are 0, r is 2, $R^5$ is hydrogen, $R^6$ and $R^7$ together with the atoms to which they are attached form an optionally substituted 6 membered heterocyclic ring having one ring nitrogen atom, $R^8$ is selected from the group consisting of hydrogen or $C_1$-$C_4$ alkyl optionally substituted with OH or $O(C^1$-$C_3$ alkyl) and G is $G^1$, such that the compounds of Formula I have the structure of Formula VIb:

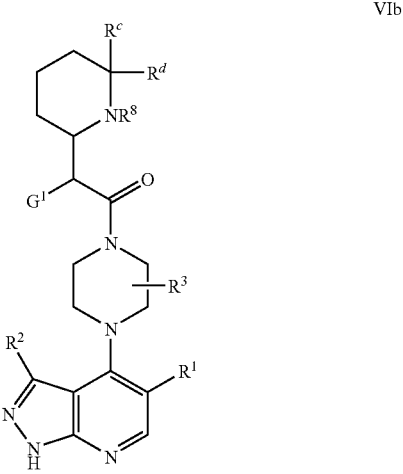

VIb wherein $G^1$ is absent or $C_1$-$C_4$ alkyl, and $R^1$, $R^2$, $R^3$, $R^c$, and $R^d$ are as defined herein.

It will be appreciated that certain compounds of the present invention may contain asymmetric or chiral centers, and therefore exist in different stereo isomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will be further appreciated that the compounds of the present invention may exist in unsolvated as well as solvated forms with pharmaceutically acceptable solvents such as water, ethanol, and the like, and it is intended that the invention embrace both solvated and unsolvated forms.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database)).

For illustrative purposes, Schemes 1-5 and Schemes A-H shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

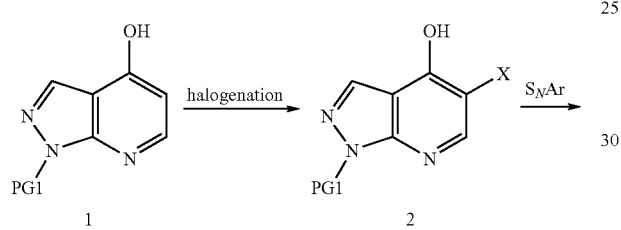

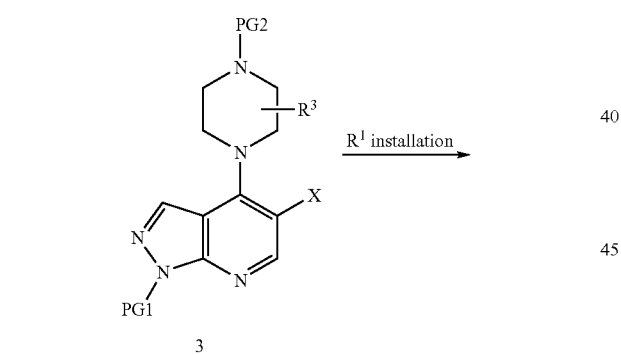

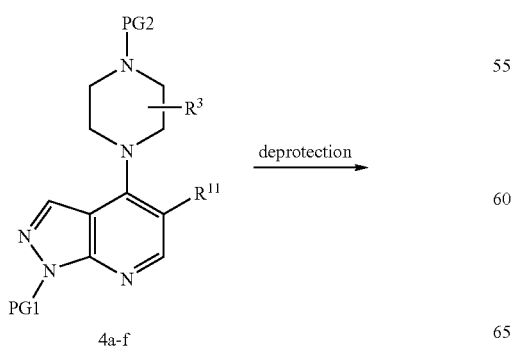

-continued

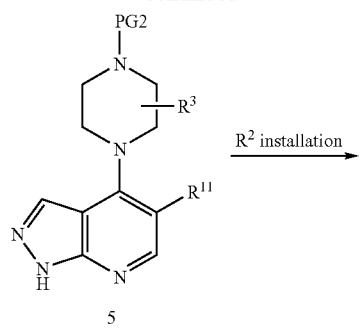

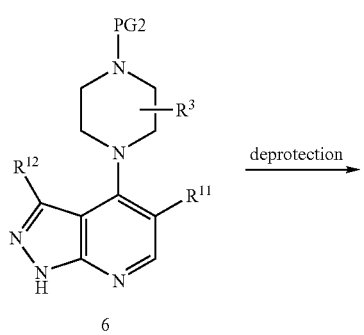

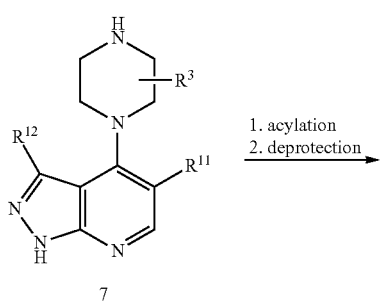

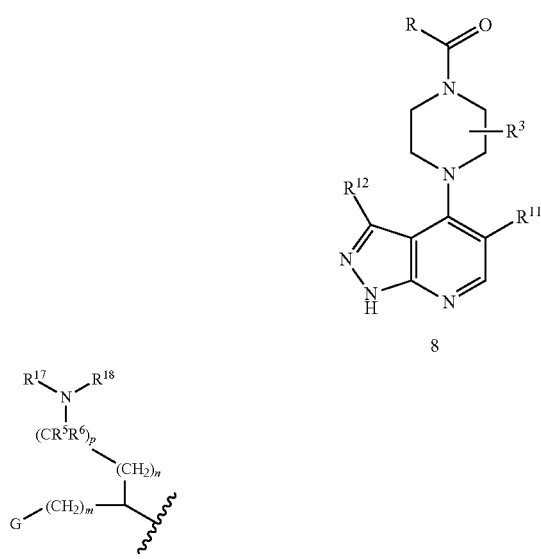

Scheme 1 shows a method of preparing compound 8, wherein $R^{11}$ is halogen, CN, $CF_3$, alkyl, cycloalkyl, aryl, heteroaryl, or $OR^g$, $R^g$ is alkyl, aryl or heteroaryl, $R^{12}$ is W—Y, and W is O, $CH_2$, NH or a direct bond to Y and Y is $C_1$-$C_6$ alkyl, $C_1$-$C_6$ alkenyl (wherein when Y is alkenyl, W is a direct bond to Y), $C_3$-$C_6$ cycloalkyl, aryl, a 5 or 6 membered heterocycle or a 5 or 6 membered heteroaryl, wherein the aryl, heterocycle or heteroaryl may be further optionally substituted with one to three substituents selected from halogen, OH, $CF_3$, CN or oxo (only on heterocycle); and the alkyl, alkenyl, and cycloalkyl may be optionally substituted with one to three substituents selected from aryl, heterocycle, heteroaryl, halogen, OH, $CF_3$, CN or oxo; and $R^3$ is as defined herein. Preparation of compound 1, wherein PG1 is a protecting group such as paramethoxylbenzyl ("PMB"), or other appropriately substituted benzyl groups, can be carried out as described in the literature (WO 2007/103308). Halogenation of compound 1 using $Br_2$, $I_2$ or N-chlorosuccinimide ("NCS") provides compound 2, wherein X is Cl, Br or I. Conversion of 2 to the triflate, followed by an $S_NAr$ reaction with an appropriately substituted piperazine gives compound 3, wherein PG2 is a protecting group such as t-butoxycarbonyl ("Boc"), benzyloxycarbonyl ("Cbz"), benzyl, or other appropriately substituted benzyl groups. Standard coupling reactions (for example, Suzuki coupling, ether formation, etc., as detailed in Scheme 2) provides compounds 4a-f. Removal of the protecting group under standard conditions (for example, trifluoroacetic acid ("TFA") to remove PMB or Boc) group) provides compound 5. Further elaboration of 5 can be carried out as necessary as shown in Scheme 3, 4 and 5 to provide compounds 6. Compound 6 is then deprotected to give compound 7, followed by acylation with an appropriate acid in the presence of a coupling reagent (such as 2-(1H-benzotriazole-1-yl)-1,1,3,3-tetramethyluronium hexafluorophosphate, "HBTU") to give compound 8, wherein $R^{17}$ and $R^{18}$ are independently selected from hydrogen; $C_1$-$C_6$ alkyl optionally substituted with halogen, oxo, OH, $OCH_3$, $CF_3$, $NH_2$, $NH(C_1$-$C_6$ alkyl), $N(C_1$-$C_6$ alkyl$)_2$, $C_3$-$C_6$ cycloalkyl, a 4-6 membered heterocycle, $C_4$-$C_6$ aryl, a 5-6 membered heteroaryl and the cycloalkyl, heterocycle, aryl and heteroaryl are further optionally substituted with one to three substituents selected from halogen, $C_1$-$C_3$ alkyl, OH, O($C_1$-$C_3$ alkyl), $CF_3$, CN, cyclopropylmethyl or oxo (only on the cycloalkyl or heterocycle); —O—($C_1$-$C_6$ alkyl) wherein the alkyl is optionally substituted with halogen, oxo, OH, O($C_1$-$C_3$ alkyl), $CF_3$, $NH_2$, $NH(C_1$-$C_6$ alkyl), $N(C_1$-$C_6$ alkyl)2, $C_3$-$C_6$ cycloalkyl, a 4-6 membered heterocycle, $C_4$-$C_6$ aryl, a 5-6 membered heteroaryl and the cycloalkyl, heterocycle, aryl and heteroaryl are further optionally substituted with one to three substituents selected from halogen, $C_1$-$C_3$ alkyl, OH, O($C_1$-$C_3$ alkyl), $CF_3$, CN, cyclopropylmethyl or oxo (only on the cycloalkyl or heterocycle); $C_3$-$C_6$ cycloalkyl, a 4-6 membered heterocycle, $C_4$-$C_6$ aryl, a 5-6 membered heteroaryl, wherein the cycloalkyl, heterocycle, aryl and heteroaryl are further optionally substituted with one to three substituents selected from halogen, $C_1$-$C_3$ alkyl, OH, O($C_1$-$C_3$ alkyl), $CF_3$, CN, $NH_2$, $NH(C_1$-$C_6$ alkyl), $N(C_1$-$C_6$ alkyl$)_2$, cyclopropyl, cyclopropylmethyl or oxo (only on the cycloalkyl or heterocycle); or —CH($CH_3$)CH(OH)phenyl; and $R^5$, $R^6$, G, m, n and p are as defined herein.

In another embodiment of the present invention, a process for preparing compounds of Formula I is provided, comprising:

(a) acylation of a compound of Formula 7:

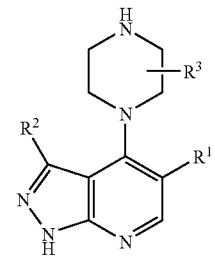

7 wherein $R^1$ is is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$ or —$OR^f$, provided that when $R^1$ is hydrogen, then $R^2$ is —$OR^f$;

$R^3$ is selected from H or $C_1$-$C_3$ alkyl;

$R^e$ is is $C_1$-$C_4$ alkyl optionally substituted with OH or a 5-6 membered heterocycle;

$R^f$ is $C_1$-$C_4$ alkyl optionally substituted with one or more OH groups;

with a compound of Formula A:

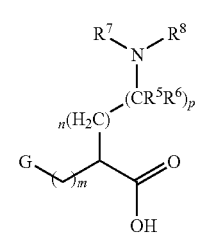

A wherein G is phenyl optionally substituted by 1-3 independent $R^4$ groups, or when m is 0, G may additionally be absent or $C_1$-$C_4$ alkyl;

each $R^4$ is independently selected from halogen, $CF_3$, $OCF_3$ and CN;

$R^5$ and $R^6$ are independently selected from hydrogen or $CH_3$;

$R^7$ and $R^8$ are independently selected from hydrogen or $C_1$-$C_6$ alkyl;

m, n and p are independently 0 or 1;

in the presence of a coupling reagent;

(b) followed by optional elaboration of $R^1$; and (c) followed by optional deprotection provides compounds of Formula I.

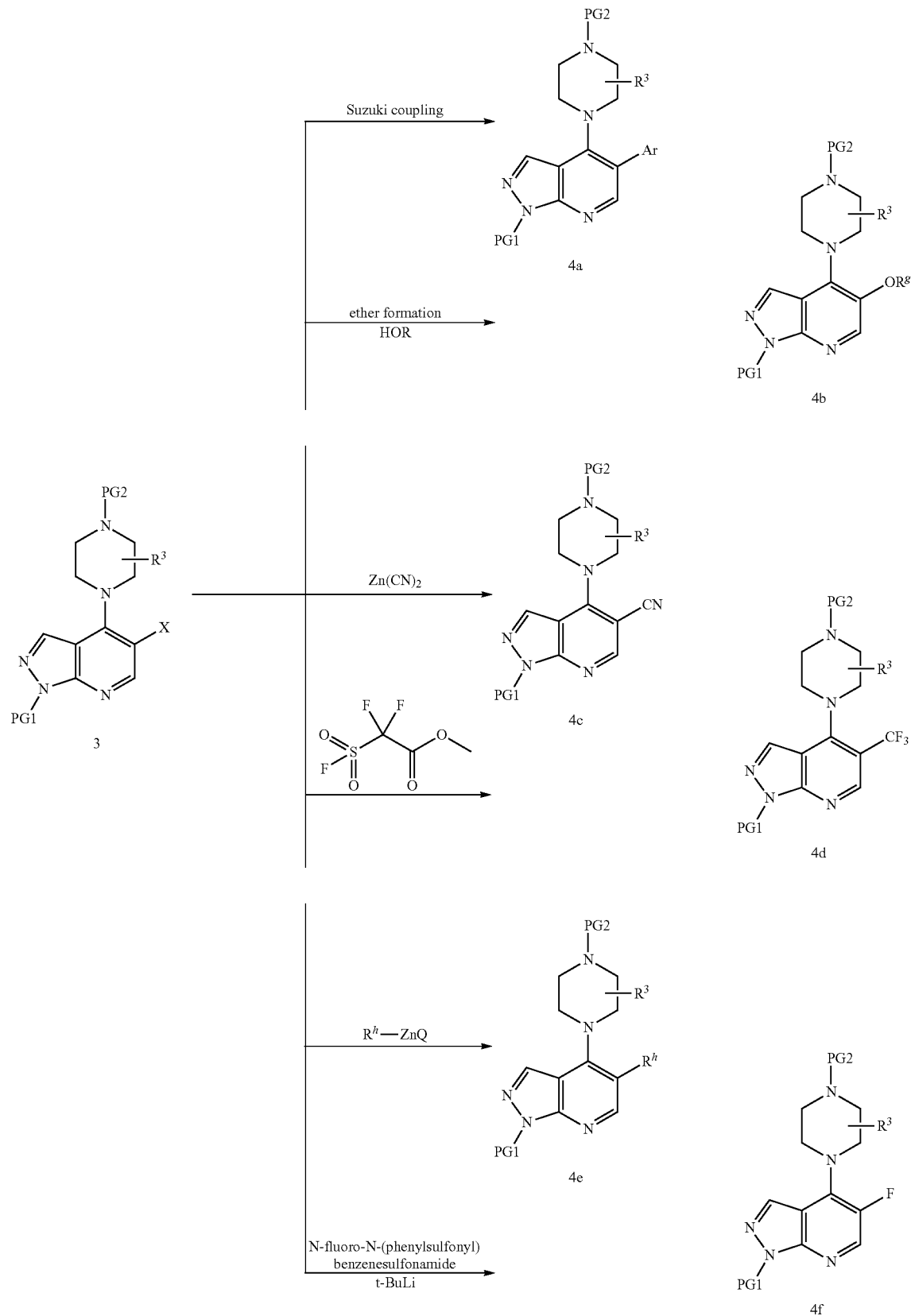
Scheme 2

Scheme 2 shows methods of installing $R^{11}$ to prepare compounds 4a-f, wherein X is Cl, Br or I, PG1 and PG2 are defined in Scheme 1 and $R^3$ is as defined herein. A variety of Pd(0) or Cu(I) catalyzed reactions can be used, including a Pd(0) catalyzed Suzuki coupling to give 4a, wherein Ar=aryl or heteroaryl. Alternatively, a Cu(I) catalyzed ether formation gives 4b, wherein $R^g$=alkyl, aryl or heteroaryl. Cyanation can be achieved using a palladium catalyzed reaction and $Zn(CN)_2$ to give 4c. When X=I, treatment with Cu(I)I and methyl 2,2-difluoro-2-(fluorosulfonyl)acetate gives 4d. Conversion of 3 to 4e can be achieved using a palladium mediated coupling reaction with an appropriate alkylzinc halide ($R^hZnQ$), wherein $R^h$ is alkyl and Q is halogen. Conversion of compound 3 to compound 4f can be carried out via standard lithium exchange reaction (e.g., t-BuLi in an appropriate solvent such as tetrahydrofuran, "THF") and trapping with a suitable electrophile (e.g., N-fluoro-N-(phenylsulfonyl)benzenesulfonamide) to give compound 4f. Specific examples are detailed in the experimental section.

three substituents selected from halogen, OH, $CF_3$, CN or oxo (only on heterocycle); and the alkyl, alkenyl, and cycloalkyl may be optionally substituted with one to three substituents selected from aryl, heterocycle, heteroaryl, halogen, OH, $CF_3$, CN or oxo; PG2 is defined in Scheme 1 and $R^{11}$ and $R^3$ are as defined herein. Halogenation of compound 5 under standard conditions gives compound 5d, wherein X is a halogen. Compound 5d can be converted to compound 6 by protecting the pyrrole N—H, followed by a suitable coupling reaction. These coupling reactions include, but are not limited to, Negishi, Heck, Suzuki or a variety of transition metal mediated coupling methods (including Cu, Pd and Ni), which can be used to install a variety of $R^{12}$ groups. Specific coupling procedures are detailed in the Examples section. Deprotection then gives compound 6.

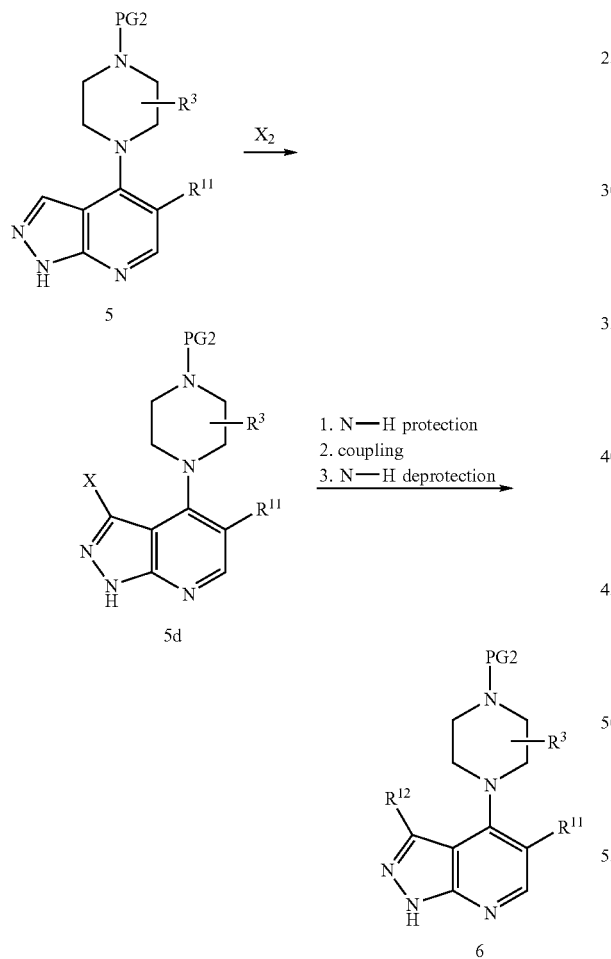

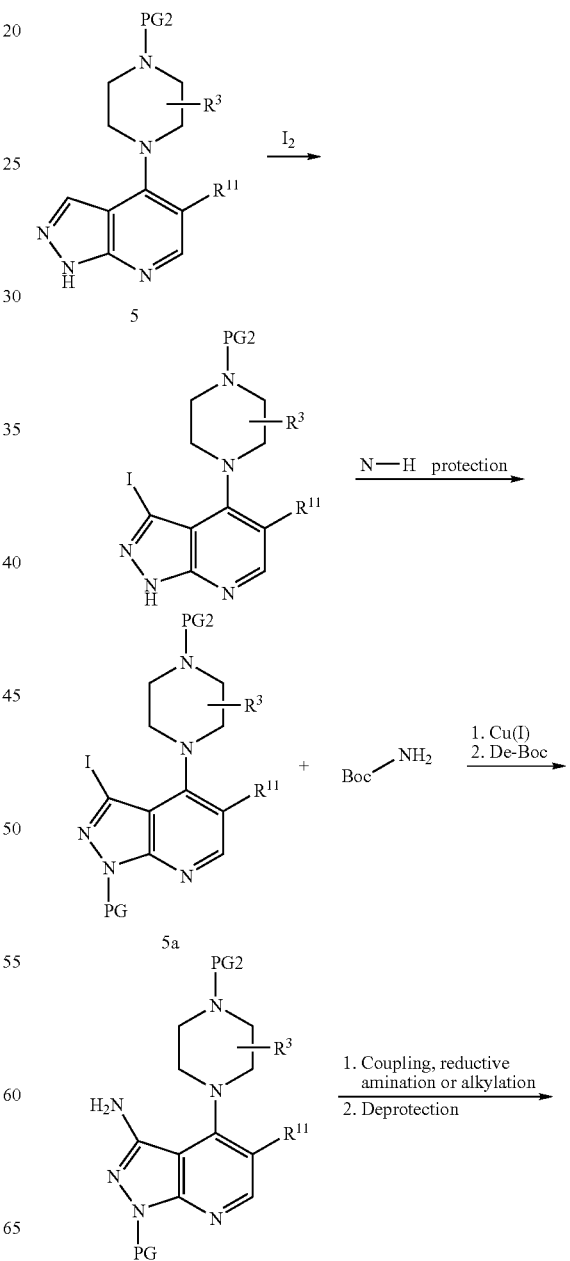

Scheme 3 shows a method for installation of the $R^{12}$ group to provide compounds 6, wherein $R^{12}$ is W—Y, and W is O, $CH_2$, NH or a direct bond to Y and Y is $C_1$-$C_6$ alkyl, $C_1$-$C_6$ alkenyl (wherein when Y is alkenyl, W is a direct bond to Y), $C_3$-$C_6$ cycloalkyl, aryl, a 5 or 6 membered heterocycle or a 5 or 6 membered heteroaryl, wherein the aryl, heterocycle or heteroaryl may be further optionally substituted with one to

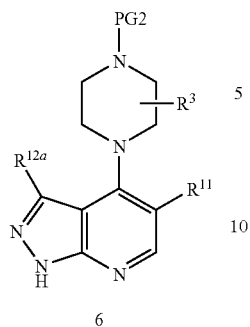

6

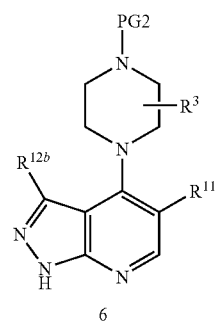

6

Scheme 4 shows another method of installing $R^{12a}$ groups to provide compound 6, wherein $R^{12a}$ is NH—Y, and Y is $C_1$-$C_6$ alkyl, $C_3$-$C_6$ cycloalkyl, aryl, a 5 or 6 membered heterocycle or a 5 or 6 membered heteroaryl, wherein the aryl, heterocycle or heteroaryl may be further optionally substituted with one to three substituents selected from halogen, OH, $CF_3$, CN or oxo (only on heterocycle); and the alkyl and cycloalkyl may be optionally substituted with one to three substituents selected from aryl, heterocycle, heteroaryl, halogen, OH, $CF_3$, CN or oxo; PG2 is defined in Scheme 1 and $R^{11}$ and $R^3$ are as defined herein. Ionization of 5, followed by N—H protection (such as PMB), wherein PG is as defined above, a Cu(I) catalyzed coupling reaction with tert-butyl carbamate and deprotection of the Boc group gives the 3-amino intermediate. The 3-amino compound can then be used in a transition metal catalyzed coupling reaction, reductive amination or alkylation reaction to install $R^{12a}$, followed by deprotection to give compound 6.

Scheme 5 shows yet another method of installing $R^{12b}$ group to provide compound 6, wherein $R^{12b}$ is $C_1$-$C_6$ alkenyl optionally substituted with one to three substituents selected from halogen, OH, $CF_3$, CN, $C_1$-$C_6$ alkyl, $C_3$-$C_6$ cycloalkyl, aryl, a 5 or 6 membered heterocycle or a 5 or 6 membered heteroaryl, wherein the alkyl, cycloalkyl, aryl, heterocycle or heteroaryl may be optionally substituted with one to three substituents selected from halogen, OH, $CF_3$, CN or oxo (only on the alkyl, cycloalkyl or heterocycle), PG2 is defined in Scheme 1 and $R^{11}$ and $R^3$ are as defined herein. Compound 5a can be converted to the 3-formyl intermediate 5b, wherein Z is B(OH)2 or Sn(Bu)$_3$ and R″ is H, alkyl, or aryl, using a palladium mediated coupling followed by oxidative cleavage (using conditions such as, but not limited to, ozonolysis or OsO$_4$/NaIO$_4$) to give the aldehyde. The formyl substitution can then be further elaborated to $R^{12b}$ by a variety of substitution reactions, such as, but not limited to, Wittig, Horner-Emmons or Emmons-Wadsworth, to provide compound 6.

The amino acids used in the synthesis of compounds of Formula I as illustrated in Schemes 1-5 and in the Examples are either commercially available or may be prepared according to the methods disclosed herein. For example, in certain embodiments the amino acids used to prepare compounds of Formula I include β-phenylglycine amino acids having the Formula 1A, γ-phenylglycine amino acids having the Formula 2A, β-phenylalanine amino acids having the Formula 3A, and γ-phenylalanine amino acids having the Formula 4A:

Scheme 5

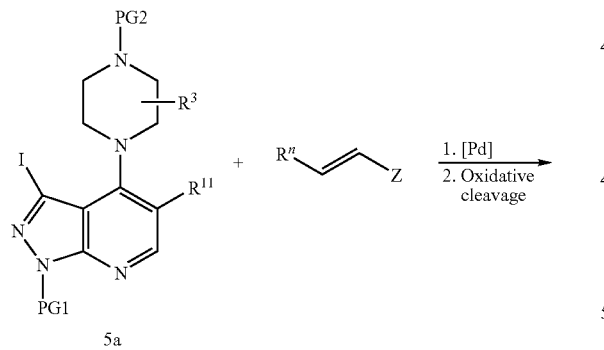

5a

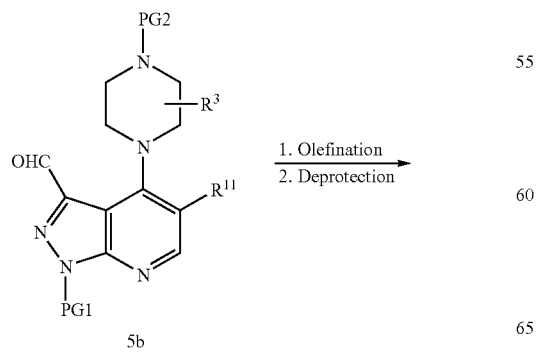

5b

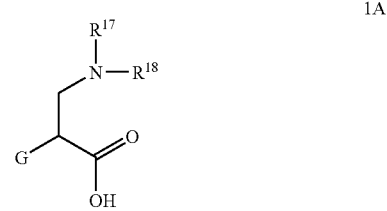

1A

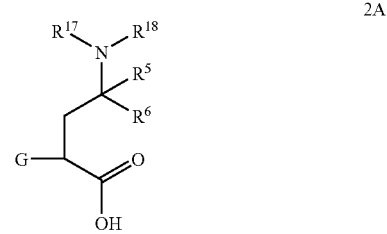

2A

-continued

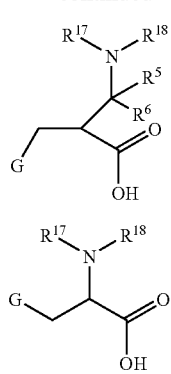

wherein $R^{17}$, $R^{18}$, G, $R^5$ and $R^6$ are as defined above.

Methods of preparing amino acids of Formulas 1A-4A are shown in Schemes A-H.

alcohol (e.g. MeOH) in the presence of a catalytic amount of an acid such as concentrated $H_2SO_4$ or a coupling agent such as dicyclohexylcarbodiimide ("DCC")/4-dimethylaminopyridine ("DMAP"); or alternatively by treatment with an appropriate electrophile (e.g., MeI, EtBr, BnBr) in the presence of a base such as $NEt_3$/DMAP at an appropriate temperature (e.g., −20° C. to 100° C.). The appropriate choice of ester is determined by the conditions required to reform the acid at the end of the synthesis, with many appropriate examples and conditions being listed in 'Protective Groups in Organic Synthesis' by Greene and Wuts, Wiley-Interscience, third edition, Chapter 5. Introduction of the hydroxymethyl group to provide compound 11 may be performed by treatment with an appropriate aldehyde (e.g., formaldehyde) in the presence of base, such as NaOEt at an appropriate temperature (e.g., −20° C. to room temperature). Activation of the alcohol group of compound 11 to form a leaving group (e.g., a mesylate, tosylate, halide) may be accomplished by treatment with, for example, methanesulphonyl chloride in the

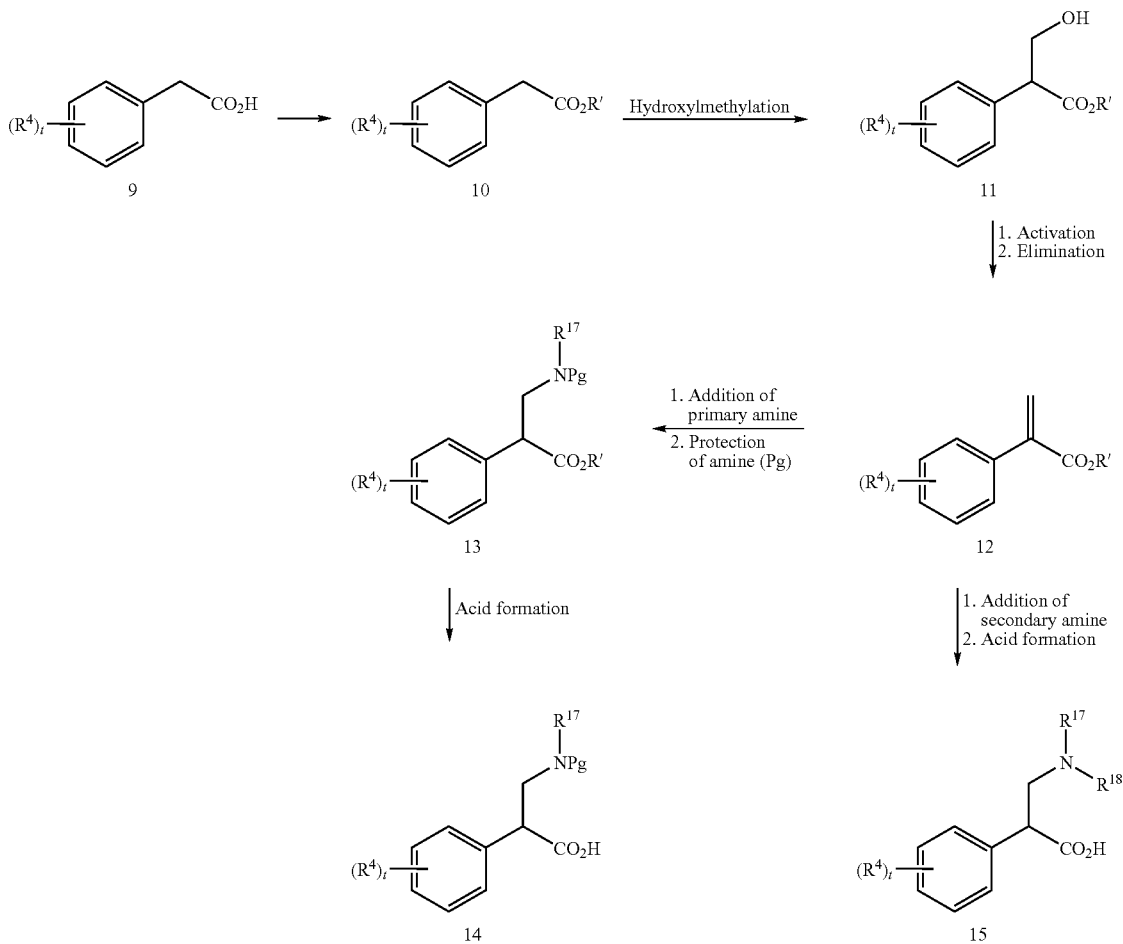

Scheme A illustrates a method of preparing optionally substituted β-phenylglycine amino acids 14 and 15 of the Formula 1A, wherein t is 0 to 4, PG is an amine protecting group, $R^{17}$ is an amine protecting group or as defined above and $R^{18}$ and $R^4$ are as defined above. According to Scheme A, the acid 9 is converted to an ester 10, wherein R' is alkyl, using standard conditions such as treatment with an appropriate presence of excess base such as $NEt_3$, N,N-diisopropylethylamine ("DIEA"), or 1,8-diazabicycloundec-7-ene ("DBU") at an appropriate temperature (e.g., −20° C. to room temperature). In many cases the olefin 12 can be isolated directly from this procedure. In other cases, warming (30° C. to 100° C.) or additional base (e.g., DBU in the case of halide) may be required to complete the elimination to provide compound 12. The activated olefin 12 may be treated with the desired primary amine (e.g., ethylamine) in a suitable solvent, such as THF, at an appropriate temperature (e.g., −20° C. to reflux) to generate the amino ester intermediate. In the case where compound 12 has an electron rich aromatic ring or electron poor/bulky primary amine, heating (e.g., 30-240° C. in a sealed tube) or microwave chemistry may be required. Protection of the amine group (for example as Boc-group) may be accomplished using di-tert-butyl dicarbonate ("$Boc_2O$") under standard conditions to provide compound 13, wherein Pg is an amine protecting group. Alternative protecting groups may be used, and many appropriate examples are listed in 'Protective Groups in Organic Synthesis' by Greene and Wuts, Wiley-Interscience, third edition, Chapter 7. Saponification of the ester 13 to form the protected amino acid 14 may be accomplished using conditions appropriate for the ester (e.g., aqueous LiOH for methyl esters, hydrogenation for benzyl esters, acid for t-butyl esters).

Alternatively, the activated olefin 12 may be treated with a secondary amine (e.g., diethylamine) in a suitable solvent such as THF at an appropriate temperature (e.g., −20° C. to reflux) to generate the aminoester intermediate (not shown). In the case where compound 12 has an electron rich aromatic ring or electron poor/bulky secondary amine, heating (e.g., 30-240° C. in a sealed tube) or microwave chemistry may be required. Saponification of the ester to form the amino acid 15 may be accomplished using conditions appropriate for the ester (e.g., aqueous LiOH for methyl esters, hydrogenation for benzyl esters, acid for t-butyl esters, etc.).

Scheme B shows a method of preparing optionally substituted γ-phenylglycine amino acids 19 of Formula 2A, wherein t is 0 to 4 and $R^4$, $R^5$, and $R^6$ are as defined herein. The starting unsaturated ester 12, wherein R' is alkyl (may be prepared according to Scheme A), can be treated with a substituted nitromethane derivative (e.g., nitroethane) in the presence of a base, such as DBU, at an appropriate temperature (e.g., 0° C. to room temperature) to give the homologated adduct 16. The nitro group of compound 16 can be reduced using standard conditions (e.g., hydrogenation, Zn/acid, etc.) at an appropriate temperature (e.g., room temperature to reflux), and the resulting intermediate can be cyclized to give the lactam intermediate 17. Protection of the amine, for example with a Boc-group to provide compound 18, may be accomplished using $Boc_2O$ under standard conditions. Alternative protecting groups may be used, and many appropriate examples are listed in 'Protective Groups in Organic Synthesis' by Greene and Wuts, Wiley-Interscience, third edition, Chapter 7. Treatment of compound 18 with an aqueous base such as LiOH or KOH at an appropriate temperature (e.g., 0° C. to 100° C.) effects ring opening of the lactam to give the appropriately substituted protected amino acid compound 19.

In one alternative of Scheme B, Boc may be replaced with $R^{17}$, as defined above, in compounds 18 and 19.

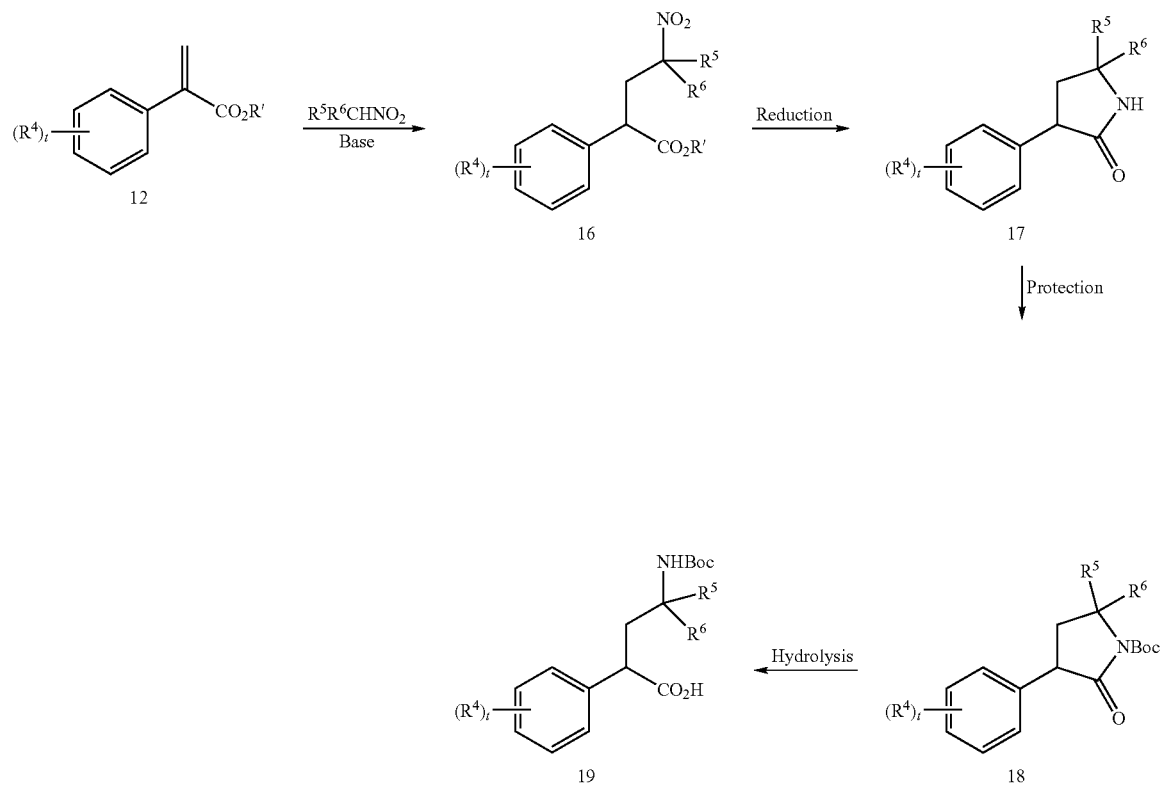

Scheme C

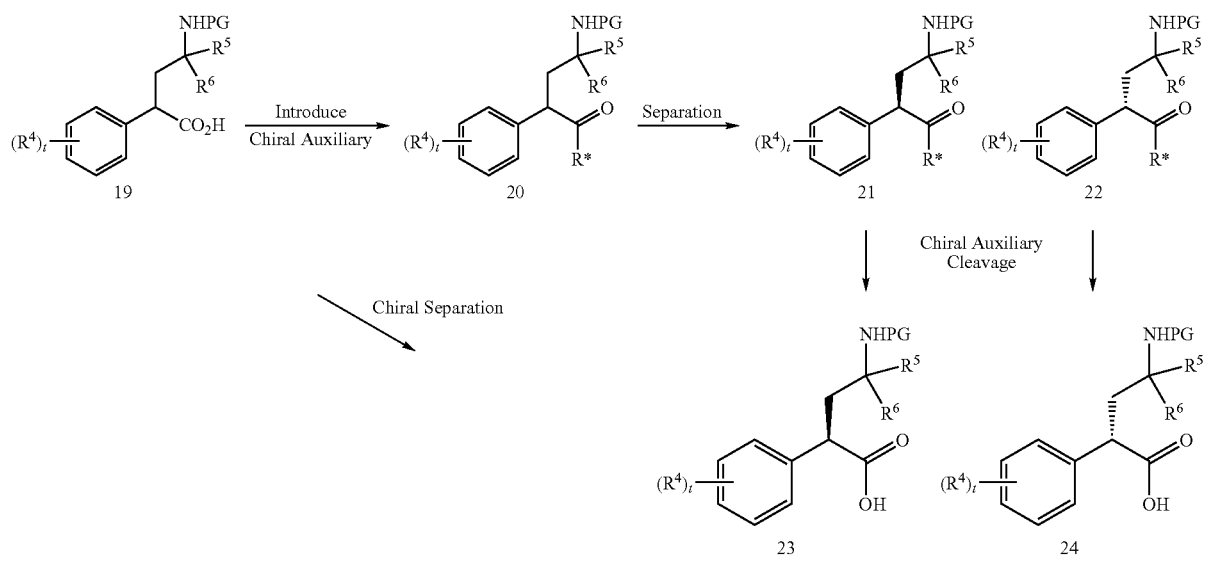

Scheme C shows representative methods of forming the single enantiomers of the gamma amino acids 23 and 24, wherein t is 0 to 4, PG is an amine protecting group such as Boc and $R^4$, $R^5$, and $R^6$ are as defined herein. In one possible method, the racemic amino acid is subject to chiral chromatographic separation using a chiral stationary phase. Alternatively, a diastereomeric mixture may be prepared which could be separated by conventional chromatographic or crystallization techniques. For example, activation of compound 19 (e.g., $COCl_2$, base) and introduction of a chiral auxiliary (e.g. an Evans' oxazolidinone) in the presence of a basic amine (e.g., Hunig's base) at −20° C. to 50° C. gives the diastereomeric mixture of compounds 21 and 22, wherein R* is a chiral auxiliary (such as Evans' oxazolidinone). This mixture may be separated using standard conditions (e.g., column chromatography, HPLC, SFC, etc.) to give the individual diastereomers. These may be converted to the desired acids by cleavage of the chiral auxiliary (in the case of an Evans' auxiliary, by using (for example) LiOH/HOOH at −15° C. to room temperature) to give compounds 23 and 24. The temperature may need to be kept low so as to prevent racemization of the newly separated chiral center.

Scheme D

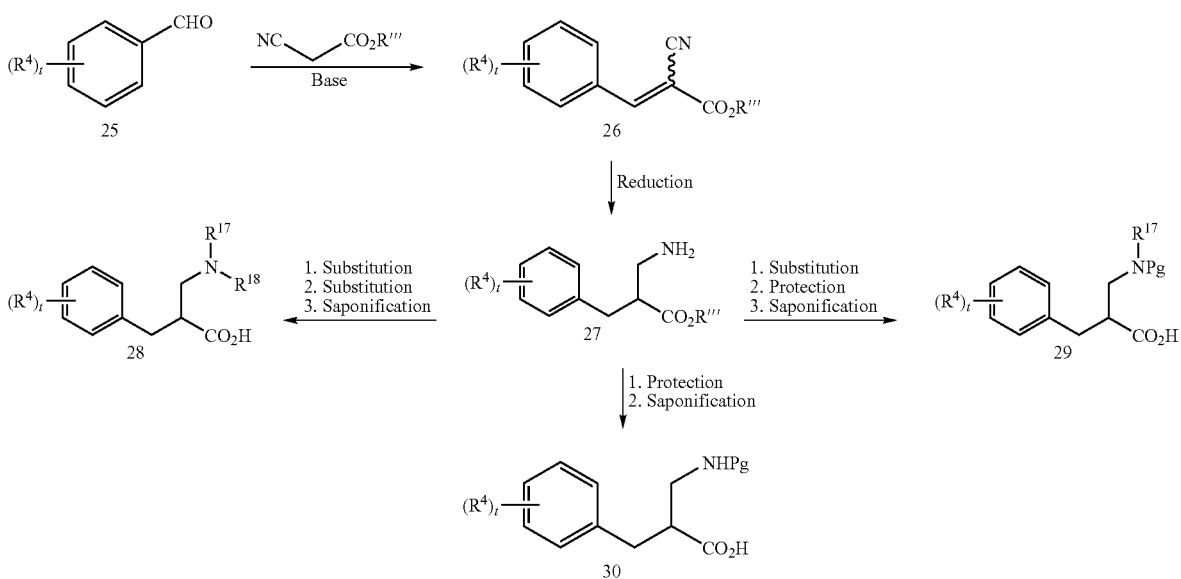

Scheme D shows a method of preparing optionally substituted β-phenylalanine amino acids 28, 29 and 30 of Formula 3A, wherein t is 0 to 4, PG is an amine protecting group, $R^{17}$ and $R^{18}$ are as defined in Scheme A and $R^4$ is as defined herein. An appropriately substituted aldehyde 25 can be treated with a cyanoacetate of the formula CN—CH$_2$CO$_2$R''', wherein R''' is alkyl (e.g., ethyl 2-cyanoacetate), in the presence of a suitable base, such as piperidine, at an appropriate temperature (e.g., room temperature to reflux) to give the unsaturated ester 26. Reduction of the olefin and the nitrile groups of compound 26 to provide compound 27 may be accomplished in a number of ways. For example, the olefin may be reduced with any agent known to effect 1,4-reductions, such as NaBH$_4$. The nitrile may be reduced using agents such as LiAlH$_4$ or NaBH$_4$ in the presence of a Lewis acid such as BF$_3$.OEt$_2$ or TFA. A number of alternative reducing agents may be used, such as those listed in 'Reductions in Organic Chemistry' by Hudlicky, ACS monograph, 2$^{nd}$ edition, Chapter 18. If desired, the primary amine 27 can be monoalkylated or bisalkylated at this stage using standard conditions (e.g., reductive amination using an appropriate aldehyde, Lewis acid and reducing agent) to provide intermediates (not shown) en route to compounds 28 and 29. To prepare primary and secondary amines, protection may be accomplished using any number of protecting groups (e.g., 'Protective Groups in Organic Synthesis' by Greene and Wuts, Wiley-Interscience, third edition, Chapter 7), for example as a Boc-group using Boc anhydride at 0° C. to room temperature. Cleavage of the ester group to form the amino acid 28, 29 or 30 may be accomplished using an aqueous bases such as LiOH or KOH, or any of the alternative reagents listed in the aforementioned 'Protecting Groups' text (e.g., hydrogenation for a benzyl ester).

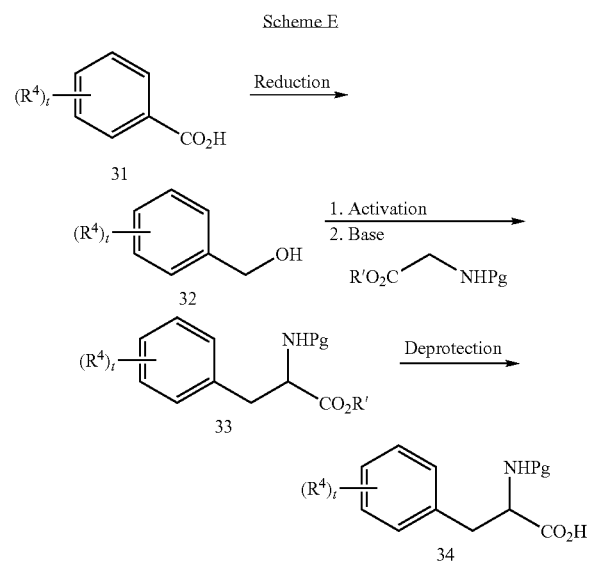

Scheme E shows a method of preparing optionally substituted α-phenylalanine amino acids 34 of Formula 4A, wherein t is 0 to 4, PG is an amine protecting group and R$^4$ is as defined herein. An appropriately substituted acid 31 may be reduced to the benzyl alcohol 32 using, for example, LiAlH$_4$ at a temperature ranging from room temperature to reflux. The alcohol group of compound 32 can be activated as a leaving group (e.g., halide, mesylate, etc.) using, for example, PBr$_3$, MsCl/NEt$_3$, etc. Displacement of this leaving group using a protected glycine derivative such as ethyl 2-(diphenylmethyleneamino)acetate in the presence of strong base, such as lithium diisopropylamide ("LDA") or n-BuLi, provides the amino ester intermediate 33, wherein R' is alkyl. Appropriate protecting groups are listed in 'Protective Groups in Organic Synthesis' by Greene and Wuts, Wiley-Interscience. The amine protecting group may be changed at this stage, for example, to introduce a Boc-group. Subsequent deprotection of the ester 33 (e.g., using 3N HCl, LiOH, hydrogenation for a benzyl ester, etc.) at an appropriate temperature (e.g., 0° C. to reflux) provides the desired N-protected amino acid 34.

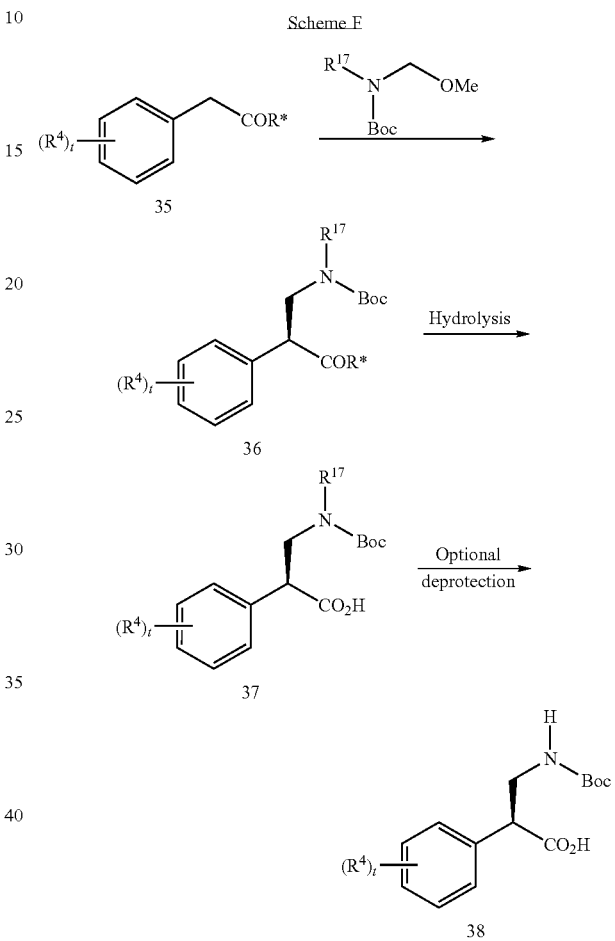

Either enantiomer of the β-amino acids may be prepared using a procedure such as that shown in Scheme F. A 2-phenylacetate 35, wherein t is 0 to 4, R* is an appropriate chiral auxiliary (for example, an Evans' auxiliary or a Sultam) and R$^4$ is as defined herein, having an appropriate chiral auxiliary (R*) with the appropriate stereochemistry to generate the desired chemistry at the β-position of the amino acid may be treated with an imine or iminium ion synthon (e.g., prepared in situ by the presence of a Lewis acid (e.g., TiCl$_4$) and an appropriately substituted alkoxymethanamine or N-(alkoxymethyl)amide/carbamate at −100° C. to 50° C.) to prepare compound 36, wherein R$^{17}$ is an amine protecting group or as defined above. The asymmetric addition may require the presence of Lewis acids (e.g., TiCl$_4$), amine bases (e.g., Hunig's base) and lower temperatures (e.g., −100° C. to 0° C.) to generate the best levels of stereochemical induction. If the diastereoselectivity is lower than required, the separate diastereomers may be separated at this stage by (for example) chromatography or crystallization. Cleavage of the chiral auxiliary, using methods known to cleave the chosen auxiliary (e.g., LiOH/H$_2$O$_2$ at −50° C. to 50° C. for the Evans auxiliary) then leads to the desired N-protected β-amino acid 37 with the desired stereochemistry at the β-position. Additionally, if $R^{17}$ is also a protecting group (e.g., 2,4-dimethoxybenzyl), it may be removed in the presence of the Boc-group (e.g., hydrogenation or DDQ, etc.) to give the Boc-amino acid 38, which upon removal of the Boc-group would provide the primary amine (not shown), which may be further functionalized by alkylation, acylation or reductive amination (either prior to or after coupling with the pyrimidine-piperazine unit). Alternatively, the Boc group of compound 37 may be elaborated to $R^{18}$, which is defined above.

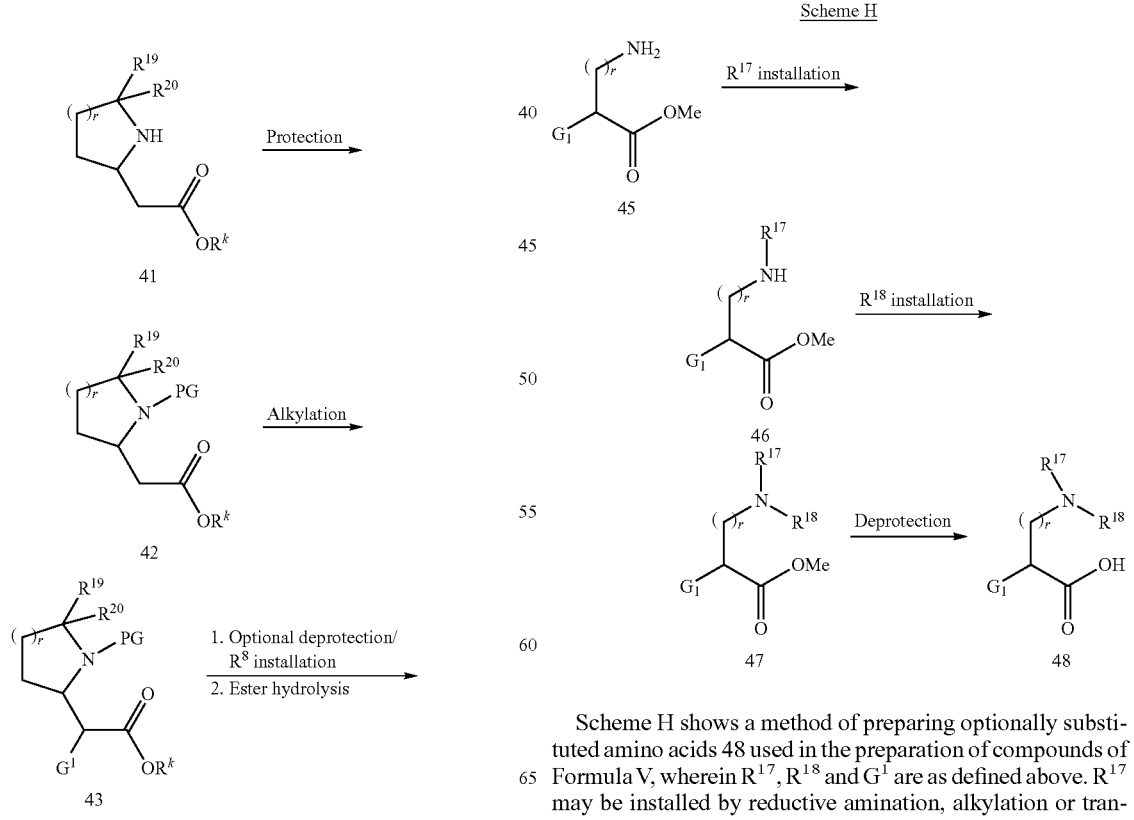

Scheme G shows a method of preparing optionally substituted amino acids 44 used in preparing compounds of Formula VI, wherein $R^{19}$ and $R^{20}$ are independently selected from hydrogen, halogen, $C_1$-$C_4$ alkyl optionally substituted with one to three substituents selected from halogen, OH, $CF_3$, CN or oxo, $R^k$ is methyl or ethyl, PG is an amine protecting group, and $R^8$, $G^1$ and r are as defined above. An appropriately substituted lactam 39 may be reduced to an aminal using, for example, $LiBEt_3H$. The aminal can then be treated with sodium hydride and a reagent such as $(EtO)_2P(O)CH_2CO_2Et$ to provide the unsaturated ester 40. Removal of the protecting group PG, and treatment with base (for example, $Et_3N$), provides the cyclized compound 41. Subsequent protection of the amine gives compound 42. Optional installation of the $G^1$ group can be carried out on compound 42 using an appropriate base (for example, LiHMDS) and an alkyl halide to provide compound 43. Ester hydrolysis can then be carried out directly on 43 to give the corresponding acid directly, or compound 43 can be optionally deprotected, followed by $R^8$ installation and ester hydrolysis to give compound 44.

Scheme H shows a method of preparing optionally substituted amino acids 48 used in the preparation of compounds of Formula V, wherein $R^{17}$, $R^{18}$ and $G^1$ are as defined above. $R^{17}$ may be installed by reductive amination, alkylation or transition metal catalyzed coupling reactions of a commercially available amino acid methyl ester or prepared by the corresponding amino acid to give compound 46. $R^{18}$ may be installed in a similar manner and followed by hydrolysis to give the optionally substituted amino acid 48.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, BOC, CBz and 9-fluorenylmethyleneoxycarbonyl ("Fmoc"). The need for such protection is readily determined by one skilled in the art. For a general description of protecting groups and their use, see T. W. Greene, Protective Groups in Organic Synthesis, John Wiley & Sons, New York, 1991.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982)47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (W. J. Lough, Ed., Chapman and Hall, New York, "Chiral Liquid Chromatography" (1989); Okamoto, J. of Chromatogr., 513:375-378 (1990)). Enriched or purified enantiomers can be distinguished by methods used to distinguish other chiral molecules with asymmetric carbon atoms, such as optical rotation and circular dichroism.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Howard C. Ansel et al., Pharmaceutical Dosage Forms and Drug Delivery Systems, ($8^{th}$ Ed. 2004); Alfonso R. Gennaro et al, Remington: The Science and Practice of Pharmacy, ($20^{th}$ Ed. 2000); and Raymond C. Rowe, Handbook of Pharmaceutical Excipients, ($5^{th}$ Ed. 2005). The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of the present invention, or a stereoisomer or pharmaceutically acceptable salt thereof. In a further embodiment, the present invention provides a pharmaceutical composition comprising a compound of the present invention, or a stereoisomer or pharmaceutically acceptable salt thereof, together with a pharmaceutically acceptable carrier or excipient.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of the present invention, or a stereoisomer or pharmaceutically acceptable salt thereof, and a pharmaceutically acceptable carrier, adjuvant, or vehicle in an amount to detectably inhibit CHK1 activity.

In another embodiment of the present invention, a method of treating a hyperproliferative disease in a mammal comprising administering a therapeutically effective amount of the compound of the present invention, or a stereoisomer or pharmaceutically acceptable salt thereof, to the mammal is provided.

In another embodiment, a method of treating or preventing cancer, including the below identified conditions, in a mammal in need of such treatment, wherein the method comprises administering to said mammal a therapeutically effective amount of a compound of the present invention, or a stereoisomer or pharmaceutically acceptable salt thereof.

Because of the ability of a CHK1 inhibitor to potentiate the activity of many anti-cancer agents it is expected that a wide range of tumor types may be treated by the compositions and methods of the invention. These conditions include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma. The term hyperproliferative disease includes the above identified conditions. The term "cancerous cell" as provided herein, includes a cell afflicted by any one of the above identified conditions.

Another embodiment of the present invention provides the use of a compound of the present invention, or a stereoisomer or pharmaceutically acceptable salt thereof, in the manufacture of a medicament for the treatment of cancer.

In another embodiment, a method of treating or preventing a disease or disorder modulated by CHK1 and/or CHK2, comprising administering to a mammal in need of such treatment an effective amount of a compound of the present invention, or a stereoisomer or pharmaceutically acceptable salt thereof.

In another embodiment, a method of preventing or treating cancer, comprising administering to a mammal in need of such treatment an effective amount of a compound of the present invention, alone or in combination with one or more additional compounds having anti-cancer properties.

CHK1 inhibitors are expected to potentiate the activity of a wide range of anti-cancer agents, when such agent(s) trigger the CHK1 dependent cell cycle checkpoint.

The invention relates to a composition for the treatment of a hyperproliferative disease in a mammal, comprising a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The invention also relates to a method for the treatment of a hyperproliferative disorder in a mammal that comprises administering to said mammal a therapeutically effective amount of a compound of the present invention, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

Another embodiment provides the compounds of the present invention for use in therapy.

Another embodiment provides the compounds of the present invention for use in the treatment of a hyperproliferative disease. In a further embodiment, the hyperproliferative disease is cancer, including the above identified conditions.

This invention also relates to a pharmaceutical composition for inhibiting abnormal cell growth in a mammal which comprises an amount of a compound of the present invention, or a stereoisomer or a pharmaceutically acceptable salt thereof, in combination with an amount of a chemotherapeutic, wherein the amounts of the compound, stereoisomer or salt and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

This invention relates to a method for inhibiting abnormal cell growth in a mammal or treating a hyperproliferative disorder in which the method comprises administering to the mammal an amount of a compound of the present invention, or a stereoisomer or a pharmaceutically acceptable salt thereof, in combination with radiation therapy, wherein the amounts of the compound or salt, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a compound of the present invention or a stereoisomer or a pharmaceutically acceptable salt thereof, which amount is effective in sensitizing abnormal cells to radiation treatment. The amount of the compound, stereoisomer or salt to be used in this method can be determined according to means for ascertaining effective amounts of such compounds as described herein or by methods know to those skilled in the art.

Another embodiment of the present invention provides the use of a compound of the present invention, or a stereoisomer or pharmaceutically acceptable salt thereof, in the manufacture of a medicament for the treatment of hyperproliferative diseases. In a further embodiment, the hyperproliferative disease may be cancer, including the above identified conditions.

Another embodiment provides the use of a compound of the present invention in the manufacture of a medicament, for use as a CHK1 and/or CHK2 inhibitor in the treatment of a patient undergoing cancer therapy.

In another embodiment, a pharmaceutical composition comprising a compound of the present invention for use in the treatment of a hyperproliferative disease is provided.

In another embodiment, a pharmaceutical composition comprising a compound of the present invention for use in the treatment of cancer is provided.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, including compounds that work by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) or on a Biotage SP4 system using C18H columns (unless otherwise stated). $^1$H NMR spectra were recorded on a Varian instrument operating at 400 MHz. $^1$H-NMR spectra were obtained as CDCl$_3$, d$_6$-DMSO, CH$_3$OD or d$_6$-acetone solutions (reported in ppm), using TMS as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Example A

CHK1 Enzymatic Assay

Compounds were diluted in dimethylsulfoxide ("DMSO") in 3 fold serial dilutions and then added to the reaction to give a final concentration of 1% DMSO. Compounds were tested in an enzymatic assay using human CHK1 kinase domain, amino acids 1 to 273, with 10 additional histidine residues on the carboxy terminus, purified from bacculovirus. The substrate was the flourescent Omnia peptide S/T11 from Invitrogen. The assay contained 25 mM HEPES pH 7.4, 10 mM $MgCl_2$, 1 mM DTT, 0.01% Triton-X100, 0.5 nM CHK1 enzyme, 2 uM S/T 11 peptide substrate, 60M ATP, test compound, 1% DMSO, in a 25 μL reaction volume. The assay was run at room temperature in white 384 well polypropylene plates (available from Nunc, Inc of Naperville, Ill.) collecting data every 50 seconds for 45 minutes in an Envision plate reader (PerkinElmer, Inc. of Waltham, Mass.), excitation 340 nM, emission 495 nM. The collected data from each well was fit to a straight line and the resulting rates were used to calculate a percent of control. $IC_{50}$ values for each test compound were determined from the percent of control vs. compound concentration plots using a four parameter fit.

The compounds of Examples 1-38 were tested in the above assay and found to have an $IC_{50}$ of less than 10 μM.

Example B

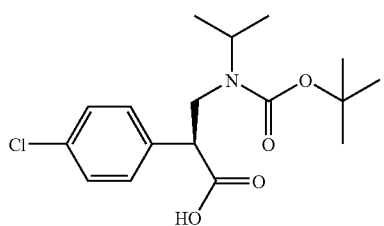 [SMILES: CC(C)N(C[C@@H](C(=O)O)c1ccc(Cl)cc1)C(=O)OC(C)(C)C]

(S)-3-(tert-butoxycarbonyl(isopropyl)amino)-2-(4-chlorophenyl)propanoic acid

Methyl 2-(4-chlorophenyl)acetate (36.7 g, 199 mmol) and paraformaldehyde (6.27 g, 209 mmol) were dissolved/suspended in DMSO (400 mL) and treated with NaOMe (537 mg, 9.94 mmol). The mixture was allowed to stir at room temperature for 2 hours to completion by thin layer chromatography ("TLC") analysis of the crude. The reaction was poured into ice-cold water (700 mL; white emulsion) and neutralized with the addition of 1M HCl solution. The aqueous layer was extracted with ethyl acetate (3×), and the organics were combined. The organic layer was washed with water (2×), brine (1×), separated, dried over $MgSO_4$, filtered, and concentrated in vacuo to afford the crude product as an oil. The residue was loaded onto a large fritted filtered with silica gel and eluted with 9:1 hexanes:ethyl acetate until the starting material/olefin were collected. The plug was then eluted with 1:1 hexanes:ethyl acetate until the pure desired product was eluted completely. The concentrated pure fractions yielded methyl 2-(4-chlorophenyl)-3-hydroxypropanoate as an oil (39.4 g, 92%).

Methyl 2-(4-chlorophenyl)-3-hydroxypropanoate (39.4 g, 184 mmol) was dissolved in dichloromethane ("DCM"; 500 mL) and treated with triethylamine ("TEA"; 64.0 mL, 459 mmol). The solution was cooled to 0° C. and slowly treated with MsCl (15.6 mL, 202 mmol), then allowed to stir for 30 minutes to completion by TLC analysis. The solution was partitioned with 1N HCl solution, and the aqueous layer was extracted once with DCM. The combined organic layer was washed once more with 1N HCl solution, separated, washed with diluted $NaHCO_3$ solution, and separated. The organic layer was dried over $MgSO_4$, filtered, and concentrated in vacuo to afford an oil. The residue was loaded onto a large fritted filter with a plug of silica gel and eluted with 9:1 hexanes:ethyl acetate affording the pure desired product by TLC analysis. The concentrated pure fractions yielded the methyl 2-(4-chlorophenyl)acrylate as an oil (30.8 g, 85%). This methyl 2-(4-chlorophenyl)acrylate (500 mg, 2.54 mmol) was added as a solution in THF (1.35 mL) to a stirring solution of i-$PrNH_2$ (217 μL, 2.54 mmol) in THF (5.0 mL) at 0° C. The reaction was allowed to stir at room temperature overnight to completion by LCMS analysis. The $Boc_2O$ (584 μL, 2.54 mmol) was added to the stirring amine via pipet. The reaction was allowed to stir overnight to completion by LCMS and TLC analysis of the mixture. The solution was concentrated in vacuo to afford methyl 3-(tert-butoxycarbonyl(isopropyl)amino)-2-(4-chlorophenyl)propanoate as an oil (854 mg, 94%). LC/MS (APCI+) m/z 256.1 [M-Boc]+.

Methyl 3-(tert-butoxycarbonyl(isopropyl)amino)-2-(4-chlorophenyl)propanoate (133 g, 374 mmol) was dissolved in THF (1.0 L) and treated with potassium trimethylsilanolate ("KOTMS"; 56.0 g, 392 mmol) at room temperature. The mixture was allowed to stir overnight to completion by LCMS analysis of the crude. The mixture was concentrated in vacuo to afford a wet foam, which was allowed to dry under vacuum overnight to afford potassium 3-(tert-butoxycarbonyl(isopropyl)amino)-2-(4-chlorophenyl)propanoate as a solid (148.7 g, 105%). LC/MS (APCI+) m/z 242.1 [M-Boc-K]+.

Potassium 3-(tert-butoxycarbonyl(isopropyl)amino)-2-(4-chlorophenyl)propanoate (77.2 g, 203 mmol) was dissolved in THF (515 mL) and treated with pivaloyl chloride (26.3 mL, 213 mmol) at room temperature. The mixture was allowed to stir for 3 hours to form the mixed anhydride. (S)-4-Benzyloxazolidin-2-one (46.1 g, 260 mmol) was dissolved in THF (600 mL) and cooled to −78° C. in a separate flask. The solution was treated with n-BuLi (102 mL of a 2.50M solution in hexanes, 254 mmol) and allowed to stir for one hour. The prepared anhydride solution was added to the stirring Li-oxazolidinone via cannula, and the mixture was allowed to warm to room temperature overnight. The mixture was quenched with the addition of saturated ammonium chloride solution, and then partitioned between more water and ethyl acetate. The aqueous layer was extracted several times, and the organics were combined. The organic layer was washed with water, then brine, separated, dried over $MgSO_4$, filtered, and concentrated in vacuo. The residue was purified/separated (diastereomers) via chromatography (silica gel eluted with 4:1 hexanes:ethyl acetate) to afford the completely separated diastereomers as viscous oils: tert-butyl(R)-3-((S)-4-benzyl-2-oxooxazolidin-3-yl)-2-(4-chlorophenyl)-3-oxopropyl(isopropyl)carbamate (12.16 g, 24% based on ½ of acid racemate) and tert-butyl(S)-3-((S)-4-benzyl-2-oxooxazolidin-3-yl)-2-(4-chlorophenyl)-3-oxopropyl(isopropyl) carbamate (39.14 g, 77% based on ½ of acid racemate). LC/MS (APCI+) m/z 401.2 [M-Boc]+.

LiOH—$H_2O$ (168 mg, 4.00 mmol) was added to a stirring solution of THF (30 mL) and water (15 mL) at room temperature until it was dissolved. The mixture was treated with hydrogen peroxide (658 μL of a 35% wt. solution in water, 8.00 mmol) and allowed to stir at room temperature for 10 minutes. The reaction was cooled to 0° C. in an ice bath, and the tert-butyl(S)-3-((S)-4-benzyl-2-oxooxazolidin-3-yl)-2-(4-chlorophenyl)-3-oxopropyl(isopropyl)carbamate (1.00 g, 2.00 mmol) was added dropwise via addition funnel as a solution in THF (15 mL) over 10 minutes. The mixture was allowed to stir overnight at room temperature to completion by LCMS analysis of the crude. The reaction was cooled to 0° C., and then treated with 1M $Na_2SO_3$ (9.00 mL) solution via addition funnel over a 10 minute period. After the addition was complete, the mixture was allowed to warm to room temperature for 10 minutes. The mixture was concentrated to remove the THF, and then diluted with water. The aqueous layer was washed twice with ethyl acetate (discarded). The aqueous layer was partitioned with ethyl acetate, and then 1M HCl was added dropwise while stirring until a pH of about 2 to about 3 was attained. The aqueous layer was extracted twice with ethyl acetate, and the organics were combined. The organic was washed with brine, separated, dried over $MgSO_4$, filtered, and concentrated in vacuo. The oil product was dried under high vacuum for one hour to afford (S)-3-(tert-butoxycarbonyl(isopropyl)amino)-2-(4-chlorophenyl) propanoic acid as a viscous oil/foam (685 mg, 100%). LC/MS (APCI+) m/z 242.1 [M-Boc]+.

Example C

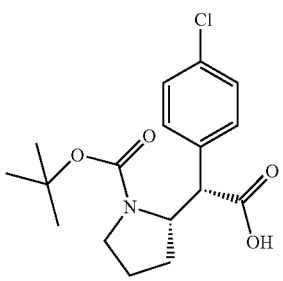 [SMILES: CC(C)(C)OC(=O)N1CCC[C@H]1[C@@H](C(=O)O)c1ccc(Cl)cc1]

(S)-2-((S)-1-(tert-butoxycarbonyl)pyrrolidin-2-yl)-2-(4-chlorophenyl)acetic acid 2-(4-Chlorophenyl)acetic acid (20.00 g, 117.2 mmol) and (R)-4-benzyloxazolidin-2-one (10.39 g, 58.62 mmol) were combined in toluene (100 mL). Triethylamine (32.68 mL, 234.5 mmol) was added, and the solution was heated to 80° C. A solution of pivaloyl chloride (14.42 mL, 117.2 mmol) in toluene (25 mL) was added dropwise. After addition, the mixture was heated to reflux for 16 hours. The reaction was cooled and washed with 2N HCl (2×), water, 5% $Na_2CO_3$ (2×), saturated NaCl, dried over $Na_2SO_4$ and concentrated in vacuo to a solid. The crude solid was subjected to chromatography on $SiO_2$ eluting with 4:1 hexane/ethyl acetate. (R)-4-Benzyl-3-(2-(4-chlorophenyl)acetyl)oxazolidin-2-one was recovered as a solid (30.7 g, 80%). $^1$H NMR ($CDCl_3$, 400 MHz) δ 7.34-7.26 (m, 7H), 7.16-7.11 (m, 2H), 4.71-4.64 (m, 1H), 4.35-4.16 (m, 4H), 3.26 (dd, $J_1$=2.9, $J_2$=13.2, 1H), 2.76 (dd, $J_1$=9.3, $J_2$=13.2, 1H).

tert-Butyl 2-oxopyrrolidine-1-carboxylate (12.33 g, 66.57 mmol) was dissolved in $Et_2O$ (60 mL) and cooled to −78° C. The suspension was treated dropwise with diisobutylaluminium hydride ("DIBAL-H"; 45.27 mL, 67.90 mmol; 1.5M in toluene), and the mixture was stirred at −78° C. for 2 hours. The mixture was allowed to warm to ambient temperature with a bath and stirred overnight. The reaction was quenched by addition of a solution of p-toluenesulfonic acid hydrate (0.075 g) in MeOH (75 mL). The mixture was stirred at ambient temperature for 16 hours. The suspension was concentrated in vacuo to a solid. This was resuspended in a mixture of Rochelle's salt (0.5N) and ethyl acetate. The layers were separated, and the aqueous layer was washed with methylene chloride (2×). The combined organic layers were washed with saturated NaCl, dried over $Na_2SO_4$ and concentrated in vacuo to provide an oil. A solution of titanium (IV) chloride (10.0 mL, 10.0 mmol; 1M in toluene) was cooled to 0° C. and treated with a solution of (R)-4-benzyl-3-(2-(4-chlorophenyl)acetyl)oxazolidin-2-one (3.00 g, 9.10 mmol) dissolved in dichloromethane (20 mL). After 5 minutes, diisopropylethylamine (1.74 mL, 10.0 mmol) was added. The resultant solution was stirred for 1 hour at 0° C. then cooled to −20° C. A solution of tert-butyl 2-methoxypyrrolidine-1-carboxylate (2.55 g, 13.65 mmol) dissolved in dichloromethane (20 mL) was added, and the mixture was stirred at −20° C. for 75 minutes. The mixture was quenched with saturated $NH_4Cl$ (about 100 mL) and diluted with water to dissolve the solids. After separation, the aqueous layer was washed with methylene chloride (3×). The combined organics were washed with water (2×), dried over $Na_2SO_4$ and concentrated in vacuo. The recovered oil was subjected to chromatography on $SiO_2$ eluting with 8:1 hexanes/ethyl acetate. (S)-tert-Butyl 2-((S)-2-((R)-4-benzyl-2-oxooxazolidin-3-yl)-1-(4-chlorophenyl)-2-oxoethyl)pyrrolidine-1-carboxylate was recovered as a sticky foam (1.55 g, 40%). MS (APCI+) [M+Na] 521.1.

Lithium hydroxide hydrate (0.0471 g, 1.12 mmol) was added to a solution of THF/water (3:1, 19 mL) and stirred until dissolved. The mixture was cooled to 0° C. and treated with 30% hydrogen peroxide (0.231 mL, 2.24 mmol) and stirred for 10 minutes. A solution of (S)-tert-butyl 2-((S)-2-((R)-4-benzyl-2-oxooxazolidin-3-yl)-1-(4-chlorophenyl)-2-oxoethyl)pyrrolidine-1-carboxylate (0.280 g, 0.561 mmol) in THF (2 mL) was added. The reaction was stirred for 30 minutes at 0° C. TLC did not show much progress, therefore the reaction was allowed to warm to ambient temperature and stirred overnight. The reaction was quenched by addition of 1.5 M $Na_2SO_3$ (1 mL) and stirred for 15 minutes. The reaction mixture was diluted with $Et_2O$ and separated. The aqueous portion was washed (2×) with $Et_2O$ then adjusted to a pH of 1 with 3N HCl. The aqueous portion was extracted (3×) with ethyl acetate. The combined organic layers were washed with water (2×), saturated NaCl, dried over $Na_2SO_4$ and concentrated in vacuo to a thick oil which slowly solidified to give (S)-2-((S)-1-(tert-butoxycarbonyl)pyrrolidin-2-yl)-2-(4-chlorophenyl)acetic acid as a foam (0.55 g, 72%). $^1$H NMR ($CDCl_3$, 400 MHz) δ 7.30 (d, 2H), 7.21 (d, 2H), 4.53-4.40 (m, 1H), 4.37-4.27 (m, 1H), 3.34-3.22 (m, 1H), 2.98-2.90 (m, 1H), 2.02-1.90 (m, 1H), 1.83-1.74 (m, 1H), 1.64-1.53 (m, 2H), 1.50 (s, 9H).

Example D

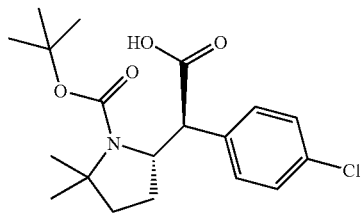 [SMILES: CC(C)(C)OC(=O)N1[C@H]([C@@H](C(=O)O)c2ccc(Cl)cc2)CCC1(C)C]

(S)-2-((S)-1-(tert-butoxycarbonyl)-5,5-dimethylpyrrolidin-2-yl)-2-(4-chlorophenyl)acetic acid 5,5-Dimethylpyrrolidin-2-one (0.108 g, 0.953 mmol; may be prepared as described in Ganem, B. and Osby, J O; Tet Lett 26:6413 (1985)) was dissolved in THF (3 mL) and cooled to −20° C. The solution was treated with lithium hexamethyldisilazide ("LHMDS"; 1.05 mL, 1.05 mmol) and stirred at −20° C. for 30 minutes. di-tert-Butyl dicarbonate (0.250 g, 1.14 mmol) was added, and the reaction mixture was allowed to warm to ambient temperature. The reaction was stirred at ambient temperature for two hours, and then quenched with saturated $NH_4Cl$, diluted with ethyl acetate and separated. The organic layer was washed with saturated $NH_4Cl$, saturated $NaHCO_3$, saturated NaCl, dried over $Na_2SO_4$ and concentrated in vacuo to an oil. The crude product was subjected to chromatography on $SiO_2$ and eluted with 4:1 hexanes/ethyl acetate. tert-Butyl 2,2-dimethyl-5-oxopyrrolidine-1-carboxylate (Rf of 0.11 in 4:1 hexanes/ethyl acetate) was recovered as a solid (0.087 g, 43%). $^1$H NMR ($CDCl_3$, 400 MHz) δ 2.48 (t, J=7.8, 2H), 1.85 (t, 2H), 1.54 (s, 9H), 1.47 (s, 6H).

tert-Butyl 2,2-dimethyl-5-oxopyrrolidine-1-carboxylate (1.17 g, 5.49 mmol) was dissolved in $Et_2O$ (15 mL) and cooled to −78° C. The solution was treated with DIBAL-H (3.73 mL, 5.60 mmol). The mixture was stirred at −78° C. for 2 hours and then warmed to ambient temperature overnight. The reaction was quenched by addition of an aliquot (7 mL) of a solution of p-toluenesulfonic acid hydrate (0.012 g) in MeOH (12 mL). The mixture was stirred at ambient temperature for 60 hours. The suspension was concentrated in vacuo and re-suspended in a mixture of Rochelle's salt (0.5N) and ethyl acetate. After separation, the aqueous portion was washed with ethyl acetate (2×). The combined organics were then washed with saturated NaCl, dried over $Na_3SO_4$ and concentrated in vacuo to an oil (92%). A solution of titanium (IV) chloride (3.71 mL, 3.71 mmol) in toluene was cooled to 0° C. and treated with a solution of (R)-4-benzyl-3-(2-(4-chlorophenyl)acetyl)oxazolidin-2-one (1.11 g, 3.38 mmol) dissolved in dichloromethane (7 mL). After 5 minutes, diisopropylethylamine (0.647 mL, 3.71 mmol) was added. The resultant solution was stirred for 1 hour at 0° C. and then cooled to −20° C. A solution of tert-butyl 5-hydroxy-2,2-dimethylpyrrolidine-1-carboxylate (1.09 g, 5.06 mmol) in dichloromethane (7 mL) was added, and the mixture was stirred at −20° C. for 75 minutes. The reaction was quenched with saturated $NH_4Cl$ (about 4 mL) and diluted with water to dissolve the solids. After separation, the aqueous portion was washed with methylene chloride (3×). The combined organics were washed with water (2×), dried over $Na_3SO_4$ and concentrated in vacuo. The crude product was subjected to chromatography on $SiO_2$ and eluted with 9:1 hexanes/ethyl acetate to produce (S)-tert-butyl 5-((S)-2-((R)-4-benzyl-2-oxooxazolidin-3-yl)-1-(4-chlorophenyl)-2-oxoethyl)-2,2-dimethylpyrrolidine-1-carboxylate (1.62 g, 61%). MS (ESI+) [M+H] 526.7/528.8.

(S)-2-((S)-1-(tert-Butoxycarbonyl)-5,5-dimethylpyrrolidin-2-yl)-2-(4-chlorophenyl)acetic acid was prepared according to the procedure described for Example C using (S)-tert-butyl 5-((S)-2-((R)-4-benzyl-2-oxooxazolidin-3-yl)-1-(4-chlorophenyl)-2-oxoethyl)-2,2-dimethylpyrrolidine-1-carboxylate. $^1$H NMR ($CDCl_3$, 400 MHz) δ 7.33-7.21 (m, 4H), 4.60-4.51 (m, 1H), 4.39-4.32 (m, 1H), 2.04-1.92 (m, 2H), 1.78-1.68 (m, 2H), 1.51 (s, 9H), 1.22 (s, 6H).

Example E

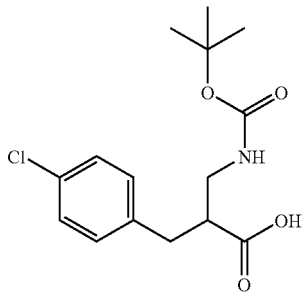 [SMILES: CC(C)(C)OC(=O)NCC(Cc1ccc(Cl)cc1)C(=O)O]

3-(tert-butoxycarbonylamino)-2-(4-chlorobenzyl) propanoic acid

Neat $SOCl_2$ (25.7 g, 216.7 mmol) was added dropwise to a −60° C. solution of MeOH (100 mL). Upon completion of the addition, 3-(4-chlorophenyl)propanoic acid (10.0 g, 54.1 mmol) was added in several portions. Upon completion of the addition, the cooling bath was removed, and the reaction mixture was slowly warmed to room temperature and stirred overnight. The reaction was then concentrated to dryness, and the resulting residue was dissolved in DCM (100 mL), washed with saturated $NaHCO_3$, dried ($MgSO_4$), filtered, and concentrated to give methyl 3-(4-chlorophenyl)propanoate as an oil (10.48 g, 97%).

BuLi (5.2 mL, 1.6M in hexanes) was added to a 0° C. solution of diisopropylamine (0.91 g, 9.0 mmol) in THF (40 mL). The reaction mixture was then stirred at 0° C. for 30 minutes, and then cooled to −78° C. A solution of methyl 3-(4-chlorophenyl)propanoate (1.5 g, 7.5 mmol) in THF (8 mL) was added slowly, and the reaction mixture was stirred at −78° C. for 40 minutes. A solution tert-butyl 2-bromoacetate (4.4 g, 22.7 mmol) in THF (5 mL) was then added. The reaction was then stirred for 30 minutes at −78° C. and then warmed to room temperature and stirred overnight. The reaction was then quenched with saturated $NH_4Cl$ and concentrated to remove THF. The reaction was then extracted with EtOAc, and the combined extracts were dried ($Na_2SO_4$), filtered, concentrated, and dried in vacuo to give 4-tert-butyl 1-methyl 2-(4-chlorobenzyl)succinate (1.91 g, 81%) as an oil.

TFA (15 mL) was added dropwise to a solution of 4-tert-butyl 1-methyl 2-(4-chlorobenzyl)succinate (1.91 g, 6.1 mmol) in DCM (30 mL) at 0° C. The reaction mixture was then warmed to room temperature and stirred for 5 hours. The reaction was then concentrated to dryness to give 3-(4-chlorobenzyl)-4-methoxy-4-oxobutanoic acid as a syrup (1.55 g, 95%), which was used without further purification.

Diphenylphosphoryl azide (2.1 g, 76 mmol) was added to a solution of 3-(4-chlorobenzyl)-4-methoxy-4-oxobutanoic acid (1.6 g, 6.4 mmol) and TEA (0.97 g, 9.58 mmol) in t-BuOH (40 mL). The reaction mixture was then heated to reflux and stirred for 6 hours. The reaction was then cooled to room temperature and concentrated to an oil. Purification by column chromatography (9:1 to 5:1 hexane:EtOAc) gave methyl 3-(tert-butoxycarbonylamino)-2-(4-chlorobenzyl) propanoate (0.64 g, 31%).

LiOH—H$_2$O (0.09 g, 2.1 mmol) was added to a solution of methyl 3-(tert-butoxycarbonylamino)-2-(4-chlorobenzyl) propanoate (0.64 g, 1.9 mmol) in 2:1 THF:H$_2$O (20 mL). The reaction was then stirred for 3 hours at room temperature and then diluted with H$_2$O (50 mL) and washed with ether (50 mL). The aqueous layer was next acidified with solid KHSO$_4$, saturated with solid NaCl, and extracted with DCM. The combined organic extracts were dried (Na$_2$SO$_4$), filtered, concentrated, and dried in vacuo to give 3-(tert-butoxycarbonylamino)-2-(4-chlorobenzyl)propanoic acid (0.523 g, 85%) as a solid. MS ESI (−) m/z 312 detected.

Example F

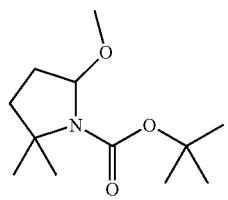 [SMILES: COC1CCC(C)(C)N1C(=O)OC(C)(C)C]

tert-butyl 5-methoxy-2,2-dimethylpyrrolidine-1-carboxylate 5,5-Dimethylpyrrolidin-2-one (0.108 g, 0.953 mmol, prepared as described in Ganem, B., et al, Tet Lett 26:6413 (1985)) was dissolved in THF (3 mL) and cooled to −20° C. The solution was treated with LHMDS (1.05 mL, 1.05 mmol) and stirred at −20° C. for 30 minutes. di-tert-Butyl dicarbonate (0.250 g, 1.14 mmol) was added, and the reaction mixture was allowed to warm to ambient temperature. The reaction was stirred at ambient temperature for two hours and then quenched with saturated NH$_4$Cl, diluted with ethyl acetate and separated. The organic layer was washed with saturated NH$_4$Cl, saturated NaHCO$_3$, saturated NaCl, dried over Na$_2$SO$_4$ and concentrated in vacuo to an oil. The crude product was subjected to chromatography on SiO$_2$ and eluted with 4:1 hexanes/ethyl acetate. tert-Butyl 2,2-dimethyl-5-oxopyrrolidine-1-carboxylate (Rf of 0.11 in 4:1 hexanes/ethyl acetate) was recovered as a solid (43%). $^1$H NMR (CDCl3, 400 MHz) δ 2.48 (t, J=7.8, 2H), 1.85 (t, 2H), 1.54 (s, 9H), 1.47 (s, 6H).

DIBAL-H (73.65 mL, 110.5 mmol, 1.5M in toluene) was added portionwise to a solution of tert-butyl 2,2-dimethyl-5-oxopyrrolidine-1-carboxylate (23.10 g, 108.3 mmol) in dry Et$_2$O (200 mL) cooled to −78° C. The reaction was stirred for 1 hour at −78° C. and then allowed to warm to room temperature and stirred overnight. The reaction was quenched with NH$_4$OH (50 mL) and stirred for 20 minutes. The reaction was then diluted with EtOAc (200 mL), 0.5M Rochelle's Salt (100 mL) was added, and the layers were separated. The organic fraction was washed with 0.5M Rochelle's Salt (2×100 mL), brine (100 mL), dried (MgSO$_4$) and concentrated to an oil. The oil was taken up in a solution of p-TsOH monohydrate (2.06 g, 10.8 mmol) in MeOH (200 mL) and stirred overnight at room temperature. The reaction was then concentrated, taken up in EtOAc (200 mL), washed with saturated Na$_2$CO$_3$ (2×100 mL), brine (50 mL), dried (MgSO$_4$) and concentrated to give tert-butyl 5-methoxy-2,2-dimethylpyrrolidine-1-carboxylate (24.07 g, 96.9% yield) as an oil.

Example G

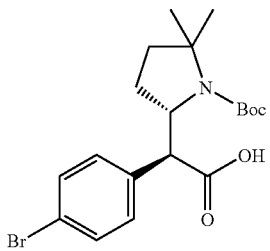

(S)-2-(4-bromophenyl)-2-((S)-1-(tert-butoxycarbonyl)-5,5-dimethylpyrrolidin-2-yl)acetic acid 2-(4-Bromophenyl)acetic acid (7.85 g, 36.5 mmol) and (R)-4-benzyloxazolidin-2-one (3.23 g, 18.3 mmol) were combined in toluene (30 mL) and triethylamine (10.2 mL, 73.0 mmol). The solution was then heated to 80° C., and a solution of pivaloyl chloride (4.49 mL, 36.5 mmol) in toluene (7.5 mL) was added slowly. The reaction was heated to 110° C. and stirred overnight. The reaction was then cooled, and the toluene solution was washed with 2N HCl, water, 5% Na$_2$CO$_3$, brine and then dried over Na$_3$SO$_4$. After removal of the solvent, the residue was purified by column chromatography to give (R)-4-benzyl-3-(2-(4-bromophenyl)acetyl)oxazolidin-2-one (5.65 g, 83%) as a solid.

TiCl$_4$ in toluene (3.52 mL, 3.52 mmol) was added to a solution of (R)-4-benzyl-3-(2-(4-bromophenyl)acetyl)oxazolidin-2-one (1.26 g, 3.35 mmol) in DCM (30 mL) at −78° C. DIEA (0.64 mL, 3.69 mmol) was then added to the cold stirring solution. The reaction was stirred at −78° C. for 15 minutes, followed by the addition of a solution of tert-butyl 5-methoxy-2,2-dimethylpyrrolidine-1-carboxylate (1.00 g, 4.36 mmol, see Example F) in DCM (10 mL). The reaction was then warmed to −10° C. and stirred for 2 hours. The reaction was quenched with a saturated NH$_4$Cl solution (20 mL), and the organic fraction was isolated, dried over sodium sulfate, filtered and concentrated. The resulting residue was purified by column chromatography to give (S)-tert-butyl 5-((R)-2-((R)-4-benzyl-2-oxooxazolidin-3-yl)-1-(4-bromophenyl)-2-oxoethyl)-2,2-dimethylpyrrolidine-1-carboxylate (1.63 g, 85%) as a solid.

30% H$_2$O$_2$ (0.67 mL, 7.0 mmol) was added to a solution of LiOH—H$_2$O (0.24 g, 5.60 mmol) in THF/water (2:1, 93 mL), and the solution was stirred at room temperature for 10 minutes. The solution was then cooled to 0° C. and treated with a solution of (S)-tert-butyl 5-((S)-2-((R)-4-benzyl-2-oxooxazolidin-3-yl)-1-(4-bromophenyl)-2-oxoethyl)-2,2-dimethylpyrrolidine-1-carboxylate (1.60 g, 2.80 mmol) in THF (10 mL). The reaction was stirred at 0° C. for 2 hours and allowed to warm to room temperature and stirred overnight. The reaction was then cooled to 0° C. and treated with 1M Na₂SO₃ (10 mL) and stirred for 10 minutes. The reaction was then warmed to room temperature and stirred for 10 minutes. The reaction was next concentrated and extracted with EtOAc (2×20 mL). The aqueous layer was then acidified with 1N HCl to a pH of about 1 to about 2 and extracted with DCM (2×20 mL). The combined DCM fractions were dried over sodium sulfate, filtered, and concentrated to give (S)-2-(4-bromophenyl)-2-((S)-1-(tert-butoxycarbonyl)-5,5-dimethylpyrrolidin-2-yl)acetic acid (1.01 g, 87% yield) as a solid. MS ESI (+) m/z 412 detected.

Example H

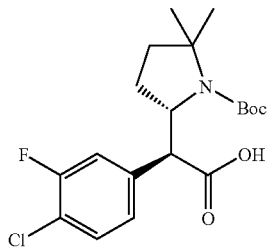 [SMILES: CC(C)(C)OC(=O)N1[C@H]([C@@H](C(=O)O)c2ccc(Cl)c(F)c2)CCC1(C)C]

(S)-2-((S)-1-(tert-butoxycarbonyl)-5,5-dimethylpyrrolidin-2-yl)-2-(4-chloro-3-fluorophenyl)acetic acid 2-(4-Chloro-3-fluorophenyl)acetic acid (1.00 g, 5.30 mmol) was dissolved in THF (14 mL) at 0° C. and treated with triethylamine (0.81 mL, 5.8 mmol). Pivaloyl chloride (0.69 mL, 5.6 mmol) was then added to the solution, and the mixture was allowed to stir for one hour at 0° C. In a separate flask, (R)-4-benzyloxazolidin-2-one (0.987 g, 5.57 mmol) was dissolved in THF (14 mL) at −78° C. and treated with n-BuLi (2.54 mL, 5.83 mmol). The above anion solution was stirred for 20 minutes and then cannulated into the anhydride at −78° C. The reaction was then allowed to stir for one hour at −78° C., and then warmed to 0° C. for two hours. The mixture was quenched with the addition of saturated NH₄Cl solution (20 mL) and concentrated in vacuo. The resulting residue was then partitioned between ethyl acetate and water. The aqueous layer was extracted once with ethyl acetate, and the organic fractions were combined, washed with brine, separated, dried over MgSO₄, filtered, and concentrated in vacuo. The resulting residue was purified by column chromatography (3:1 hexanes:ethyl acetate) to give (R)-4-benzyl-3-(2-(4-chloro-3-fluorophenyl)acetyl)oxazolidin-2-one (0.95 g, 51%) as an oil, which solidified upon standing.

TiCl₄ in toluene (7.79 mL, 7.79 mmol) was added to a solution of (R)-4-benzyl-3-(2-(4-chloro-3-fluorophenyl)acetyl)oxazolidin-2-one (2.58 g, 7.42 mmol) in DCM (60 mL). DIEA (1.42 mL, 8.16 mmol) was added to this stirring cold solution, followed by a solution of tert-butyl 5-methoxy-2,2-dimethylpyrrolidine-1-carboxylate (2.21 g, 9.65 mmol) in DCM (20 mL). The reaction was stirred for 15 minutes at −78° C. and then warmed to −10° C. and stirred for 3 hours. The reaction was quenched with a saturated NH₄Cl solution (20 mL), and the organic layer was separated and dried over sodium sulfate. After removal of the solvent, the resulting residue was purified by column chromatography to give (S)-tert-butyl 5-((R)-2-((R)-4-benzyl-2-oxooxazolidin-3-yl)-1-(4-bromophenyl)-2-oxoethyl)-2,2-dimethylpyrrolidine-1-carboxylate (2.62 g, 65%) as a solid.

30% H₂O₂ (0.159 mL, 1.65 mmol) was added to a solution of LiOH—H₂O (0.055 g, 1.32 mmol) in 2:1 THF:H₂O (40 mL). The mixture was stirred for 20 minutes and then cooled to 0° C. A solution of (S)-tert-butyl 5-((S)-2-((R)-4-benzyl-2-oxooxazolidin-3-yl)-1-(4-chloro-3-fluorophenyl)-2-oxoethyl)-2,2-dimethylpyrrolidine-1-carboxylate (0.360 g, 0.660 mmol) in THF (3 mL) was next added slowly. Upon completion of the addition, the reaction was allowed to warm to room temperature and stirred overnight. The reaction mixture was then recooled to 0° C., and 1M Na₂SO₃ (4 mL) was added. The reaction was stirred for 10 minutes at 0° C. and then warmed to room temperature and stirred for an additional 10 minutes. The reaction was then concentrated in vacuo to remove THF, and the resulting mixture was washed with EtOAc. The organic fraction was then dried over sodium sulfate, filtered and concentrated to give (S)-2-((S)-1-(tert-butoxycarbonyl)-5,5-dimethylpyrrolidin-2-yl)-2-(4-chloro-3-fluorophenyl)acetic acid sodium salt (0.24 g, 94%) as a powder. MS ESI (+) m/z 386 detected.

Example I

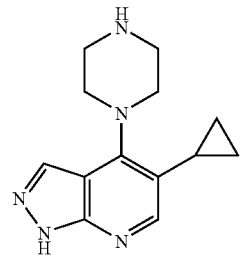 [SMILES: c1nc2[nH]ncc2c(N2CCNCC2)c1C1CC1]

5-cyclopropyl-4-(piperazin-1-yl)-1H-pyrazolo[3,4-b]pyridine

A solution of 1-(4-methoxybenzyl)-1H-pyrazolo[3,4-b]pyridin-4-ol (10.00 g, 39.17 mmol, prepared as described in WO 2007/103308) in absolute ethanol (220 mL) was cooled to 0° C., treated dropwise with bromine (2.15 mL, 43.09 mmol) and stirred at 0° C. for 30 minutes. The ice bath was then removed, and the mixture was allowed to warm to room temperature. After 30 minutes, water (150 mL) and concentrated HCl (10 mL) were added to the slurry, and the mixture was stirred at room temperature for 10 minutes. The solid formed was filtered and washed with water (3×20 mL) followed by EtOH (2×20 mL). The solid collected was triturated with CH₃CN, filtered, washed with additional CH₃CN (2×10 mL), and air dried to provide 5-bromo-1-(4-methoxybenzyl)-1H-pyrazolo[3,4-b]pyridin-4-ol (10.90 g, 83% yield) as a solid. LCMS (APCI+) m/z 333.9 (M+H)+, Retention time=2.33 minutes.

A solution of 5-bromo-1-(4-methoxybenzyl)-1H-pyrazolo[3,4-b]pyridin-4-ol (10.85 g, 32.5 mmol) in DMF (130 mL) was added dropwise to a stirred suspension of sodium hydride (60% in mineral oil, 1.56 g, 39 mmol) in DMF (70 mL) at room temperature. Once the addition was complete, the mixture was stirred at 40° C. for 30 minutes. The resulting solution was cooled to room temperature and treated with 1,1,1-trifluoro-N-phenyl-N-(trifluoromethylsulfonyl)methanesulfonamide (13.92 g, 38.96 mmol). After 1 hour, solid tert-butyl piperazine-1-carboxylate (13.3 g, 71.43 mmol) was added in 2 portions with stirring, and the mixture was stirred at 80° C. for 1.5 hours. The resulting mixture was allowed to cool to room temperature overnight. Saturated NH₄Cl solution (100 mL), water (50 mL) and EtOAc (250 mL) were then added to the reaction mixture. The phases were separated, and the aqueous layer was extracted with EtOAc (2×50 mL). The combined organic phases were washed with water (1×50 mL), dried (MgSO₄), filtered, and concentrated in vacuo. The residue obtained was crystallized from boiling EtOAc (~30 mL) and hexane (~10 mL). The solid formed was filtered, washed with additional hexane (2×10 mL), and dried to provide tert-butyl 4-(5-bromo-1-(4-methoxybenzyl)-1H-pyrazolo[3,4-b]pyridin-4-yl)piperazine-1-carboxylate (14.8 g, 91% yield) as a solid. LCMS (APCI+) m/z 504 (M+H)+, Retention time=4.56 minutes.

Cyclopropylzinc(II) bromide (2.5 mL, 2.49 mmol) was added to a solution of tert-butyl 4-(5-bromo-1-(4-methoxybenzyl)-1H-pyrazolo[3,4-b]pyridin-4-yl)piperazine-1-carboxylate (500 mg, 0.995 mmol) and Pd(PPh₃)₄ (86 mg, 0.075 mmol) in THF (5 mL) under N₂. The reaction mixture was heated at 75° C. (oil bath) under N₂ atmosphere for 18 hours. The reaction mixture was then allowed to cool to room temperature and poured into saturated aqueous NH₄Cl (50 mL) solution and extracted with EtOAc (3×50 mL). The combined organic layers were dried (MgSO₄), filtered, and concentrated in vacuo. The residue obtained was purified by C-18 reverse phase chromatography (Biotage 25M+) on Biotage SP4 unit using a 15-90% CH₃CN/water gradient (14 CV). The fractions containing the product were pooled, and the solvents were removed. The residue was evaporated from CH₃CN (3×20 mL) and dried to provide tert-butyl 4-(5-cyclopropyl-1-(4-methoxybenzyl)-1H-pyrazolo[3,4-b]pyridin-4-yl)piperazine-1-carboxylate (275 mg, 60% yield) as a solid. LCMS (APCI+) m/z 464.2 (M+H)+, Rt=4.32 minutes.

tert-Butyl 4-(5-cyclopropyl-1-(4-methoxybenzyl)-1H-pyrazolo[3,4-b]pyridin-4-yl)piperazine-1-carboxylate (275 mg, 0.593 mmol) was treated with 25% TFA/CH₂Cl₂ for 30 minutes. The solvent was then removed in vacuo, and the residue was evaporated from toluene (3×10 mL) to provide the crude 5-cyclopropyl-1-(4-methoxybenzyl)-4-(piperazin-1-yl)-1H-pyrazolo[3,4-b]pyridine TFA salt (220 mg, 102% yield). LCMS (APCI+) m/z 364.1 (M+H)+, Rt=2.61 minutes.

Neat TFA (10 mL) was added to 5-cyclopropyl-1-(4-methoxybenzyl)-4-(piperazin-1-yl)-1H-pyrazolo[3,4-b]pyridine (215 mg, 0.592 mmol), and the mixture was stirred at reflux for 2 hours. TFA was then removed under reduced pressure, and the oily residue was evaporated from CH₂Cl₂ (2×50 mL). 2M HCl in ether (10 mL) was added to the residue and sonicated for few minutes to give a solid. The solvents were then removed, and the residue obtained was evaporated from additional 2M HCl in ether (10 mL). The resulting residue was triturated with Et₂O, and the solid formed was filtered, washed with ether (2×5 mL) and dried to provide 5-cyclopropyl-4-(piperazin-1-yl)-1H-pyrazolo[3,4-b]pyridine hydrochloride salt (183 mg, 95% yield) as a solid. LCMS (APCI+) m/z 244.1 (M+H)+, Retention time=1.66 minutes.

Example J

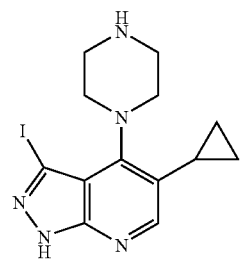 [SMILES: Ic1n[nH]c2ncc(C3CC3)c(N3CCNCC3)c12]

5-cyclopropyl-3-iodo-4-(piperazin-1-yl)-1H-pyrazolo[3,4-b]pyridine

A mixture of 5-cyclopropyl-4-(piperazin-1-yl)-1H-pyrazolo[3,4-b]pyridine hydrochloride salt (2.3 g, 7.27 mmol, see Example I), di-tert-butyl dicarbonate (3.17 g, 14.5 mmol), and N-ethyl-N-isopropylpropan-2-amine (5.1 mL, 29 mmol) in CH₂Cl₂ (100 mL) was stirred at room temperature for 90 minutes. The solvent was then removed. The residue obtained was dissolved in THF/MeOH (10:1, 100 mL) and treated with lithium hydroxide hydrate (916 mg, 21.8 mmol) in water (10 mL). After 18 hours, the solvents were removed in vacuo. The residue was dissolved in EtOAc (150 mL), and the organic layer was washed with water (2×30 mL). The layers were separated, and the organic layer was dried (MgSO₄), filtered and concentrated in vacuo. The residue was dissolved in THF:MeOH (100 mL) and retreated with LiOH.H₂O (610 mg, 14.53 mmol) in water (10 mL) for 18 hours. The solvents were then removed in vacuo, and the residue was dissolved in EtOAc (250 mL). The resulting organic layer was washed with water (2×50 mL), dried (MgSO₄), filtered, and concentrated in vacuo to provide the crude tert-butyl 4-(5-cyclopropyl-1H-pyrazolo[3,4-b]pyridin-4-yl)piperazine-1-carboxylate (1.48 g, 59% yield) as a solid. LCMS (APCI+) m/z 344.1 (M+H)+.

A mixture of tert-butyl 4-(5-cyclopropyl-1H-pyrazolo[3,4-b]pyridin-4-yl)piperazine-1-carboxylate (1.44 g, 4.2 mmol) and powdered potassium hydroxide (692 mg, 10.5 mmol) in DMF (20 mL) was treated with iodine (2.13 g, 8.39 mmol), and the mixture was heated at 60° C. for 5 hours. The mixture was cooled to room temperature, diluted with EtOAc (200 mL) and successively washed with a saturated Na₂S₂O₃ solution (2×20 mL) and water (2×50 mL). The organic layer was separated, dried (MgSO₄), filtered, and concentrated in vacuo to provide the crude tert-butyl 4-(5-cyclopropyl-3-iodo-1H-pyrazolo[3,4-b]pyridin-4-yl)piperazine-1-carboxylate (2 g, 102% yield) as a solid. LCMS (APCI+) m/z 470.1 (M+H)+.

A mixture of tert-butyl 4-(5-cyclopropyl-3-iodo-1H-pyrazolo[3,4-b]pyridin-4-yl)piperazine-1-carboxylate (200 mg, 0.426 mmol) and 4N HCl in dioxane (4 mL) was stirred at room temperature for 2 hours. The solvent was then removed in vacuo, and the residue was triturated with CH₃CN. The solid formed was filtered, washed with Et₂O and dried to provide 5-cyclopropyl-3-iodo-4-(piperazin-1-yl)-1H-pyrazolo[3,4-b]pyridine hydrochloride salt (179 mg, 95% yield) as a solid. ¹H NMR (400 MHz, d₆-DMSO) δ 9.47 (br s, 2H), 8.32 (s, 1H), 3.67-3.62 (m, 4H), 3.42-3.35 (m, 4H), 2.09-2.03

(m, 1H), 1.07-1.01 (m, 2H), 0.80-0.76 (m, 2H); LCMS (APCI+) m/z 370 (M+H)+, Retention time=1.87 minutes.

Example K

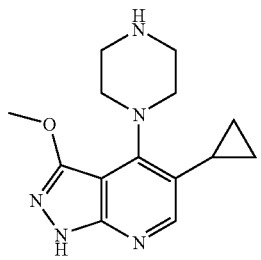 [SMILES: COc1n[nH]c2ncc(C3CC3)c(N3CCNCC3)c12]

5-cyclopropyl-3-methoxy-4-(piperazin-1-yl)-1H-pyrazolo[3,4-b]pyridine

A mixture of 5-cyclopropyl-4-(piperazin-1-yl)-1H-pyrazolo[3,4-b]pyridine dihydrochloride (2.30 g, 7.27 mmol), di-tert-butyl dicarbonate (3.17 g, 14.5 mmol), and N-ethyl-N-isopropylpropan-2-amine (5.08 mL, 29.1 mmol) in $CH_2Cl_2$ (100 mL) was stirred at room temperature for 90 minutes. The solvent was removed. The reaction mixture was dissolved in THF/MeOH (10:1, 100 mL), treated with a solution of lithium hydroxide (0.916 g, 21.8 mmol) in water (10 mL) and was stirred at room temperature overnight. The reaction was concentrated, and the residue was dissolved in EtOAc (150 mL) and washed with water (2×30 mL). The layers were separated, and the organic layer was dried ($MgSO_4$), filtered and concentrated to provide the crude product tert-butyl 4-(5-cyclopropyl-1H-pyrazolo[3,4-b]pyridin-4-yl)piperazine-1-carboxylate (1.48 g, 4.31 mmol, 59% yield) as a solid.

A mixture of tert-butyl 4-(5-cyclopropyl-1H-pyrazolo[3,4-b]pyridin-4-yl)piperazine-1-carboxylate (1.44 g, 4.19 mmol) and powdered potassium hydroxide (0.692 g, 10.5 mmol) in DMF (20 mL) was treated with iodine (2.13 g, 8.39 mmol), and the mixture was heated at 60° C. for 5 hours. The mixture was diluted with EtOAc (200 mL) and successively washed with saturated $Na_2S_2O_3$ solution (2×20 mL) and water (2×50 mL). The organic layer was separated, dried ($MgSO_4$), filtered, and concentrated in vacuo to provide the crude tert-butyl 4-(5-cyclopropyl-3-iodo-1H-pyrazolo[3,4-b]pyridin-4-yl)piperazine-1-carboxylate (2.01 g, 4.28 mmol, 100%) yield) as a solid.

1-(Chloromethyl)-4-methoxybenzene (0.734 g, 4.69 mmol) was slowly added to a stirring mixture of tert-butyl 4-(5-cyclopropyl-3-iodo-1H-pyrazolo[3,4-b]pyridin-4-yl)piperazine-1-carboxylate (2.00 g, 4.26 mmol) and potassium carbonate (0.883 g, 6.39 mmol) in DMF (30 mL) at room temperature, and the reaction was then stirred for 2 hours. EtOAc (200 mL) and water (100 mL) were added to the mixture, and the phases were separated. The organic suspension was washed with water (3×50 mL), dried ($MgSO_4$), filtered, and concentrated in vacuo to provide the crude as an oil. The residue was purified by flash chromatography on silica gel (Biotage Flash 40M+) eluting with 15% EtOAc/hexane to provide tert-butyl 4-(5-cyclopropyl-3-iodo-1-(4-methoxybenzyl)-1H-pyrazolo[3,4-b]pyridin-4-yl)piperazine-1-carboxylate (1.44 g, 57% yield) as a solid.

tert-Butyl 4-(5-cyclopropyl-3-iodo-1-(4-methoxybenzyl)-1H-pyrazolo[3,4-b]pyridin-4-yl)piperazine-1-carboxylate (0.35 g, 0.59 mmol), Cu(I)I (113 mg, 0.59 mmol), KF on $Al_2O_3$ (40%) (241 mg, 4.15 mmol), 1,10-phenanthroline (107 mg, 0.59 mmol) and MeOH (1.2026 mL, 29.688 mmol) were placed in toluene (3 mL), degassed under argon, and then heated to 110° C. overnight. The reaction was then cooled to room temperature. EtOAc was added, and the reaction was filtered through celite and washed with EtOAc. The filtrate was then concentrated, and the resulting residue was purified by column chromatography (1:1 hexanes:EtOAc) to give the product tert-butyl 4-(5-cyclopropyl-3-methoxy-1-(4-methoxybenzyl)-1H-pyrazolo[3,4-b]pyridin-4-yl)piperazine-1-carboxylate (0.21 g, 71% yield).

tert-Butyl 4-(5-cyclopropyl-3-methoxy-1-(4-methoxybenzyl)-1H-pyrazolo[3,4-b]pyridin-4-yl)piperazine-1-carboxylate (0.300 g, 0.608 mmol) was placed in DCM (5 mL). TFA (1.5 mL) was then added, and the reaction was stirred at room temperature for 1 hour. The reaction was then concentrated to dryness to give the crude product 5-cyclopropyl-3-methoxy-1-(4-methoxybenzyl)-4-(piperazin-1-yl)-1H-pyrazolo[3,4-b]pyridine (0.239 g, quant.), which was used in the next step without further purification.

5-Cyclopropyl-3-methoxy-1-(4-methoxybenzyl)-4-(piperazin-1-yl)-1H-pyrazolo[3,4-b]pyridine (239 mg, 0.6 mmol) was placed in neat TFA (5 mL) and heated to 100° C. for 15 hours. The reaction was then cooled to room temperature and concentrated to dryness. The residue was dissolved in minimal DCM and added to a stirring solution of 1M HCl in ether. The resulting yellow solid was filtered, washed with ether and dried to give 5-cyclopropyl-3-methoxy-4-(piperazin-1-yl)-1H-pyrazolo[3,4-b]pyridine hydrochloride (88 mg, 53% yield) as a solid. LCMS (APCI+) m/z 21A (M+H)+.

Example L

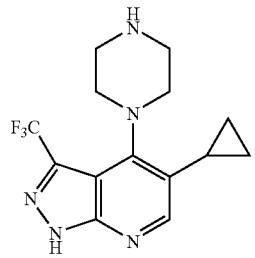 [SMILES: FC(F)(F)c1n[nH]c2ncc(C3CC3)c(N3CCNCC3)c12]

5-cyclopropyl-4-(piperazin-1-yl)-3-(trifluoromethyl)-1H-pyrazolo[3,4-b]pyridine tert-Butyl 4-(5-cyclopropyl-3-iodo-1-(4-methoxybenzyl)-1H-pyrazolo[3,4-b]pyridin-4-yl)piperazine-1-carboxylate (300 mg, 0.5 mmol), methyl 2,2-difluoro-2-(fluorosulfonyl)acetate (0.23 mL, 1.8 mmol), and CuI (97 mg, 0.5 mmol) were placed in DMF (5 mL) and heated to 100° C. for 1 hour. The reaction was then cooled to room temperature, and EtOAc was added. The reaction was filtered thru celite. The filtrate was then washed with brine. The organic fraction was dried, filtered, and concentrated to give the crude product, which was purified by column chromatography (3:1 hexanes:EtOAc) to give the product tert-butyl 4-(5-cyclopropyl-1-(4-methoxybenzyl)-3-(trifluoromethyl)-1H-pyrazolo[3,4-b]pyridin-4-yl)piperazine-1-carboxylate (265 mg, 98% yield).

tert-Butyl 4-(5-cyclopropyl-1-(4-methoxybenzyl)-3-(trifluoromethyl)-1H-pyrazolo[3,4-b]pyridin-4-yl)piperazine-1-carboxylate (270 mg, 0.5 mmol) was placed in DCM (8 mL) at room temperature. TFA (1.5 mL) was then added, and the reaction was stirred at room temperature for 1 hour and concentrated to dryness. The crude product was then azeotroped with toluene (3×) and then dried on a vac line for 1 hour to give the crude product 5-cyclopropyl-1-(4-methoxybenzyl)-4-(piperazin-1-yl)-3-(trifluoromethyl)-1H-pyrazolo[3,4-b]pyridine (0.2 g, 91% yield), which was used without further purification.

5-Cyclopropyl-1-(4-methoxybenzyl)-4-(piperazin-1-yl)-3-(trifluoromethyl)-1H-pyrazolo[3,4-b]pyridine (0.212 g, 0.491 mmol) was placed in neat TFA (3 mL) and heated to 100° C. for 48 hours. The reaction was then cooled to room temperature and concentrated to dryness. The resulting residue was dissolved in minimal DCM and added to a stirring solution of 1M HCl in ether. The resulting solid was filtered, washed with ether and dried to give 5-cyclopropyl-4-(piperazin-1-yl)-3-(trifluoromethyl)-1H-pyrazolo[3,4-b]pyridine hydrochloride (92 mg, 60% yield) as a solid. LCMS (APCI+) m/z 312 (M+H)+.

Example M

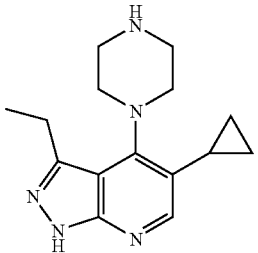 [SMILES: CCc1n[nH]c2ncc(C3CC3)c(N3CCNCC3)c12]

5-cyclopropyl-3-ethyl-4-(piperazin-1-yl)-1H-pyrazolo[3,4-b]pyridine tert-Butyl 4-(5-cyclopropyl-3-iodo-1-(4-methoxybenzyl)-1H-pyrazolo[3,4-b]pyridin-4-yl)piperazine-1-carboxylate (300 mg, 0.5 mmol), Cu(I)I (5 mg, 0.02 mmol), PdCl$_2$(PPh$_3$)$_2$ (18 mg, 0.02 mmol), and triethylamine (0.3 mL, 2.5 mmol) were placed in THF (4 mL) and de-gassed under argon. Ethynyltrimethylsilane (0.2 mL, 1.5 mmol) was then added, and the reaction was stirred at room temperature overnight. The reaction was then concentrated to dryness to give the crude product tert-butyl 4-(5-cyclopropyl-1-(4-methoxybenzyl)-3-((trimethylsilyl)ethynyl)-1H-pyrazolo[3,4-b]pyridin-4-yl)piperazine-1-carboxylate (280 mg, 98% yield).

tert-Butyl 4-(5-cyclopropyl-1-(4-methoxybenzyl)-3-((trimethylsilyl)ethynyl)-1H-pyrazolo[3,4-b]pyridin-4-yl)piperazine-1-carboxylate (280 mg, 0.50 mmol) was placed in THF (8 mL) at 0° C. TBAF (0.54 mL, 0.54 mmol) was then added, and the reaction stirred for 30 minutes at room temperature. The reaction was then poured into saturated Na$_2$CO$_3$, and extracted with DCM. The combined organic fractions were dried, filtered, and concentrated to give the crude product, which was purified by column chromatography to give tert-butyl 4-(5-cyclopropyl-3-ethynyl-1-(4-methoxybenzyl)-1H-pyrazolo[3,4-b]pyridin-4-yl)piperazine-1-carboxylate (250 mg, 96% yield).

tert-Butyl 4-(5-cyclopropyl-3-ethynyl-1-(4-methoxybenzyl)-1H-pyrazolo[3,4-b]pyridin-4-yl)piperazine-1-carboxylate (200 mg, 0.4 mmol) was placed in MeOH (2 mL). Pd/C (175 mg, 0.08 mmol) was then added, and the reaction was stirred at room temperature for 1 hour. The reaction was then filtered and concentrated to give tert-butyl 4-(5-cyclopropyl-3-ethyl-1-(4-methoxybenzyl)-1H-pyrazolo[3,4-b]pyridin-4-yl)piperazine-1-carboxylate (150 mg, 74% yield).

tert-Butyl 4-(5-cyclopropyl-3-ethyl-1-(4-methoxybenzyl)-1H-pyrazolo[3,4-b]pyridin-4-yl)piperazine-1-carboxylate (0.21 g, 0.43 mmol) was placed in DCM (5 mL). TFA (1.5 mL) was then added, and the reaction was stirred at room temperature for 1 hour and concentrated to dryness. The crude product was then azeotroped with toluene (3×) and dried to give the crude 5-cyclopropyl-3-ethyl-1-(4-methoxybenzyl)-4-(piperazin-1-yl)-1H-pyrazolo[3,4-b]pyridine (0.16 g, 96% yield).

5-Cyclopropyl-3-ethyl-1-(4-methoxybenzyl)-4-(piperazin-1-yl)-1H-pyrazolo[3,4-b]pyridine (200 mg, 0.5 mmol) was placed in neat TFA (5 mL) and heated to 80° C. for 15 hours. The reaction was then cooled to room temperature and then concentrated to dryness. The crude residue was then dissolved in minimal DCM and added to a stirring solution of 1M HCl in ether. The resulting solid was filtered, washed with ether and dried to give 5-cyclopropyl-3-ethyl-4-(piperazin-1-yl)-1H-pyrazolo[3,4-b]pyridine hydrochloride (110 mg, 79% yield) as a solid. LCMS (APCI+) m/z 272 (M+H)+.

Example N

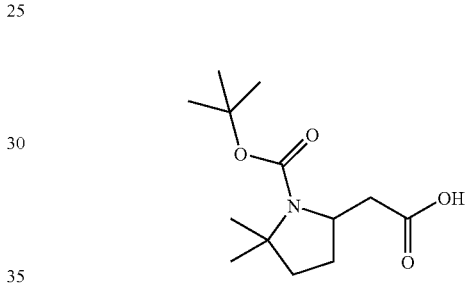

2-(1-(tert-butoxycarbonyl)-5,5-dimethylpyrrolidin-2-yl)acetic acid

A solution of 5,5-dimethylpyrrolidin-2-one (33.9 g, 300.3 mmol) in dry THF (300 mL) was chilled to −20° C., followed by the addition of LHMDS (330.4 mL, 330.4 mmol) (1M THF). The solution was allowed to stir for 30 minutes at −20° C., followed by the addition of a solution of di-tert-butyl dicarbonate (72.1 g, 330.4 mmol) in THF (20 mL). The reaction was allowed to warm to room temperature and stirred for 15 hours. The reaction was quenched with saturated NH$_4$Cl (50 mL) and diluted with EtOAc (100 mL). The layers were separated. The organic fraction was washed with saturated NH$_4$Cl (50 mL), NaHCO$_3$ (50 mL), brine (50 mL), dried (MgSO$_4$) and concentrated to a dark oil. Purification by column chromatography (10% EtOAc in hexane) gave tert-butyl 2,2-dimethyl-5-oxopyrrolidine-1-carboxylate (38.2 g, 60% yield).

DIBAL-H (73.6 mL, 110.4 mmol) (1.5M in Toluene) was added portionwise to a solution of tert-butyl 2,2-dimethyl-5-oxopyrrolidine-1-carboxylate (23.1 g, 108.3 mmol) in dry Et$_2$O (200 mL) cooled to −78° C. The reaction was stirred for 1 hour at −78° C., allowed to warm to room temperature and stirred for 15 hours. The reaction was quenched with NH$_4$OH (50 mL), stirred for 20 minutes, and then diluted with EtOAc (200 mL) and 0.5M Rochelle's Salt (100 mL). The layers were separated. The organic fraction was washed with 0.5M Rochelle's (2×100 mL), brine (100 mL), dried (MgSO$_4$) and concentrated to an oil. The oil was taken up in a solution of p-TsOH monohydrate (2.0 g, 10.8 mmol) in MeOH (200 mL)

and stirred for 15 hours at room temperature. The reaction was concentrated, taken up in EtOAc (200 mL), washed with saturated Na$_2$CO$_3$ (2×100 mL), brine (50 mL), dried (MgSO$_4$) and concentrated to an oil, tert-butyl 5-methoxy-2,2-dimethylpyrrolidine-1-carboxylate (24.1 g, 97% yield).

TiCl$_4$ (1.9 mL, 1.9 mmol) as a 1M DCM solution was added to a solution of dimethyl malonate (0.195 mL, 1.70 mmol) in DCM (10 mL) at 0° C. under N$_2$, and the reaction was stirred for 10 minutes. DIEA (0.3 mL, 1.7 mmol) was then added slowly, and the reaction was stirred for an additional 30 minutes at 0° C. A DCM (2 mL) solution of tert-butyl 5-methoxy-2,2-dimethylpyrrolidine-1-carboxylate (325 mg, 1.4 mmol) was then slowly added dropwise, and the reaction was stirred at 0° C. for 10 minutes. Saturated NH$_4$Cl was then added, and then reaction was diluted with DCM and washed with saturated NaHCO$_3$. The organic fractions were then dried, filtered, and concentrated to give the crude product, which was purified by column chromatography (500:50-500:90 hexanes:EtOAc) to give dimethyl 2-(1-(tert-butoxycarbonyl)-5,5-dimethylpyrrolidin-2-yl)malonate (0.35 g, 75%).

Dimethyl 2-(1-(tert-butoxycarbonyl)-5,5-dimethylpyrrolidin-2-yl)malonate (220 mg, 0.7 mmol) was placed in 1:1 THF:MeOH (3 mL). KOH (0.8 mL, 1.7 mmol) was then added, and the reaction heated to 65° C. for 6 hours. The reaction was then cooled to room temperature and concentrated to remove the THF and MeOH. The reaction was then acidified with 6M HCl and then heated to 85° C. overnight to achieve decarboxylation. The reaction was then cooled to room temperature and basicified with solid NaOH until a pH of 14. THF (10 mL) and Boc$_2$O (5 equivalents) were then added. The reaction was stirred for 20 hours at 50° C. and then cooled to room temperature. The reaction was extracted with DCM, and the organic fraction was discarded. The aqueous fraction was then acidified to a pH of 2 with 10% aqueous citric acid and then extracted with DCM. The combined organic fractions were dried, filtered, and concentrated to give the product 2-(1-(tert-butoxycarbonyl)-5,5-dimethylpyrrolidin-2-yl)acetic acid (130 mg, 75% yield).

Example O

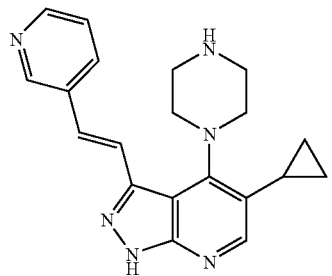 [SMILES: C(=C\c1n[nH]c2ncc(C3CC3)c(N3CCNCC3)c12)/c1cccnc1]

(E)-5-cyclopropyl-4-(piperazin-1-yl)-3-(2-(pyridin-3-yl)vinyl)-1H-pyrazolo[3,4-b]pyridine 1-(Chloromethyl)-4-methoxybenzene (734 mg, 4.69 mmol) was slowly added to a stirring mixture of tert-butyl 4-(5-cyclopropyl-3-iodo-1H-pyrazolo[3,4-b]pyridin-4-yl)piperazine-1-carboxylate (2.00 g, 4.26 mmol, see Example J) and potassium carbonate (883 mg, 6.39 mmol) in DMF (30 mL) at room temperature. After 2 hours, EtOAc (200 mL) and water (100 mL) were added to the mixture, and the phases were separated. The organic suspension was washed with water (3×50 mL), dried (MgSO$_4$), filtered, and concentrated in vacuo. The residue obtained was purified by flash chromatography on silica gel (Biotage Flash 40M+) eluting with 15% EtOAc/hexane to provide tert-butyl 4-(5-cyclopropyl-3-iodo-1-(4-methoxybenzyl)-1H-pyrazolo[3,4-b]pyridin-4-yl)piperazine-1-carboxylate (1.44 g, 57% yield) as a solid. LCMS (APCI+) m/z 590.1 (M+H)+.

A 50 mL round bottom flask charged with tert-butyl 4-(5-cyclopropyl-3-iodo-1-(4-methoxybenzyl)-1H-pyrazolo[3,4-b]pyridin-4-yl)piperazine-1-carboxylate (500 mg, 0.85 mmol), triethylamine (355 μL, 2.54 mmol), Pd$_2$dba$_3$ (19.4 mg, 0.021 mmol), tri-o-tolylphosphine (19.4 mg, 0.064 mmol), and DMF (7 mL) was purged under N$_2$ (3 cycles). 3-vinylpyridine (270.24 mg, 1.7 mmol) was added, and the mixture was stirred at 100° C. under a N$_2$ atmosphere for 6 hours. The reaction mixture was cooled to room temperature, diluted with warm EtOAc (100 mL) and washed with water (2×30 mL). The phases were separated, and the organic layer was dried (MgSO$_4$), filtered, and concentrated in vacuo. The residue was purified by flash chromatography on silica gel (Biotage Flash 40S+) eluting with 25% EtOAc/hexane followed by 50% EtOAc/hexane to provide (E)-tert-butyl 4-(5-cyclopropyl-1-(4-methoxybenzyl)-3-(2-(pyridin-3-yl)vinyl)-1H-pyrazolo[3,4-b]pyridin-4-yl)piperazine-1-carboxylate (390 mg, 81% yield) as a solid. LCMS (APCI+) m/z 567.3 (M+H)+.

A solution of (E)-tert-butyl 4-(5-cyclopropyl-1-(4-methoxybenzyl)-3-(2-(pyridin-3-yl)vinyl)-1H-pyrazolo[3,4-b]pyridin-4-yl)piperazine-1-carboxylate (385 mg, 0.68 mmol) in 25% TFA/CH$_2$Cl$_2$ was stirred at room temperature. Then the mixture was concentrated in vacuo, and the residue was evaporated from toluene (3×10 mL). TFA (10 mL) was added to the residue, and the mixture was stirred at 60° C. for 4 hours. The solvent was then removed in vacuo, and the residue was evaporated from toluene (20 mL). The residue was dissolved in CH$_2$Cl$_2$ (2 mL) and 2M HCl in Et$_2$O was added. The mixture was stirred at room temperature for 30 minutes. The resulting solid was filtered and washed with additional Et$_2$O and dried to provide (E)-5-cyclopropyl-4-(piperazin-1-yl)-3-(2-(pyridin-3-yl)vinyl)-1H-pyrazolo[3,4-b]pyridine hydrochloride salt (210 mg, 74% yield) as a solid. $^1$H NMR (400 MHz, d$_6$-DMSO) δ 9.76 (br s, 2H), 9.24 (s, 1H), 9.00 (d, 1H), 8.80 (d, 1H), 8.30 (s, 1H), 8.07 (dd, 1H), 7.93 (d, 1H), 7.59 (d, 1H), 3.78-3.72 (m, 4H), 3.33-3.26 (m, 4H), 2.17-2.10 (m, 1H), 1.06-1.02 (m, 2H), 0.83-0.79 (m, 2H); LCMS (APCI+) m/z 347.1 (M+H)+, Retention time=2.09 minutes.

Example P

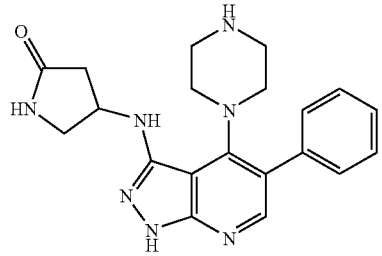 [SMILES: O=C1CC(Nc2n[nH]c3ncc(-c4ccccc4)c(N4CCNCC4)c23)CN1]

4-(5-phenyl-4-(piperazin-1-yl)-1H-pyrazolo[3,4-b]
pyridin-3-ylamino)pyrrolidin-2-one A mixture of tert-butyl 4-(3-iodo-1-(4-methoxybenzyl)-5-phenyl-1H-pyrazolo[3,4-b]pyridin-4-yl)piperazine-1-carboxylate (1.55 g, 2.4780 mmol, see Example 9), CuI (0.47 g, 2.48 mmol), N1,N2-dimethylethane-1,2-diamine (0.53 ml, 4.96 mmol) and tert-butyl carbamate (2.90 g, 24.78 mmol) in dioxane (50 mL) was stirred at 75° C. (oil bath) for 6 hours. Water (50 mL) and ethyl acetate (50 mL) were added, and the organic layer was separated, washed with saturated ammonium chloride, dried (sodium sulfate) and concentrated in vacuo. The residue was purified by flash chromatography on silica gel (hexane:ethyl acetate=1:1) to give 1-(4-methoxybenzyl)-5-phenyl-4-(piperazin-1-yl)-1H-pyrazolo[3,4-b]pyridin-3-amine (1.00 g, 97%) as a solid. This solid was dissolved in DCM (20 mL), and TFA (4.77 mL, 62.0 mmol) was added. The reaction was stirred at room temperature for 4 hours. The solvent was removed. The residue was partitioned between saturated NaHCO₃ (30 mL) and DCM (40 mL). The organic layer was separated, dried (sodium sulfate) and concentrated in vacuo to give 1-(4-methoxybenzyl)-5-phenyl-4-(piperazin-1-yl)-1H-pyrazolo[3,4-b]pyridin-3-amine (1.00 g, 97%) as a solid. LCMS (APCI+) m/z 415(M+H)+.

TEA (0.34 mL, 2.41 mmol) was added to a solution of 1-(4-methoxybenzyl)-5-phenyl-4-(piperazin-1-yl)-1H-pyrazolo[3,4-b]pyridin-3-amine (1.00 g, 2.41 mmol) and Boc₂O (0.53 g, 2.41 mmol) in DCM (20 mL) and stirred at room temperature for 1 hour. Water (20 mL) was added, and the organic layer was separated, dried (sodium sulfate) and concentrated in vacuo. The residue was purified by flash chromatography on silica gel to give tert-butyl 4-(3-amino-1-(4-methoxybenzyl)-5-phenyl-1H-pyrazolo[3,4-b]pyridin-4-yl)piperazine-1-carboxylate (1.00 g, 81%) as a solid. LCMS (APCI+) m/z 369(M+H)+.

Decaborane (0.014 g, 0.12 mmol) was added to a solution of tert-butyl 4-(3-amino-1-(4-methoxybenzyl)-5-phenyl-1H-pyrazolo[3,4-b]pyridin-4-yl)piperazine-1-carboxylate (0.20 g, 0.39 mmol) and 1-(4-methoxybenzyl)pyrrolidine-2,4-dione (0.10 g, 0.47 mmol) in MeOH (3 mL) and DCM (0.5 mL) and stirred at 48° C. (oil bath) for 20 hours. The solvent was removed. The resulting residue was dissolved in ethyl acetate (20 mL), washed with saturated NaHCO₃ (10 mL), dried (sodium sulfate) and concentrated in vacuo. The residue was purified by flash chromatography on silica gel (hexane:ethyl acetate=1:1) to give tert-butyl 4-(1-(4-methoxybenzyl)-3-(1-(4-methoxybenzyl)-5-oxopyrrolidin-3-ylamino)-5-phenyl-1H-pyrazolo[3,4-b]pyridin-4-yl)piperazine-1-carboxylate (0.20 g, 70%) as a solid. LCMS (APCI+) m/z 718(M+H)+.

TFA (0.52 mL, 6.79 mmol) was added to a solution of tert-butyl 4-(1-(4-methoxybenzyl)-3-(1-(4-methoxybenzyl)-5-oxopyrrolidin-3-ylamino)-5-phenyl-1H-pyrazolo[3,4-b]pyridin-4-yl)piperazine-1-carboxylate (0.195 g, 0.27 mmol) in DCM (1 mL) and stirred at room temperature for 1 hour. The solvent was removed. The residue was dissolved in TFA (4 mL) and heated at 100° C. in a sealed tube overnight. The TFA was removed. The residue was dissolved in DCM (0.5 mL), and HCl in ether (1 mL) was added. The solid formed was collected by filtration to give 4-(5-phenyl-4-(piperazin-1-yl)-1H-pyrazolo[3,4-b]pyridin-3-ylamino)pyrrolidin-2-one hydrochloride (0.20 g, 98% yield) as a solid.

Example Q

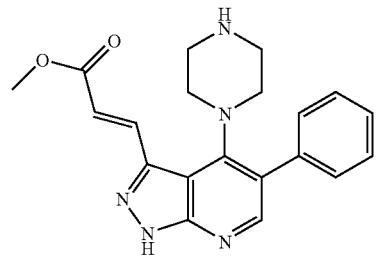 [SMILES: COC(=O)/C=C/c1n[nH]c2ncc(-c3ccccc3)c(N3CCNCC3)c12]

(E)-methyl 3-(5-phenyl-4-(piperazin-1-yl)-1H-pyrazolo[3,4-b]pyridin-3-yl)acrylate A mixture of 5-phenyl-4-(piperazin-1-yl)-1H-pyrazolo[3,4-b]pyridine hydrochloride salt (8.8 g, 25 mmol, see Example 1), di-tert-butyl dicarbonate (6 g, 27.5 mmol), and N-ethyl-N-isopropylpropan-2-amine (18 mL, 100 mmol) in THF (100 mL) was stirred at room temperature for 90 minutes. Then a solution of LiOH.H₂O (25 mmol) in water (4 mL) was added to the reaction. After 30 minutes, the mixture was concentrated in vacuo. The resulting residue was dissolved in EtOAc (200 mL) and washed with water (3×50 mL). The organic phase was separated, dried (MgSO₄), filtered, and concentrated in vacuo. The reaction did not go to completion. Therefore the crude product was dissolved in THF (150 mL), retreated with LiOH.H₂O (4.39 g, 4 equivalents) in water (15 mL) and stirred at room temperature for 18 hours. The mixture was then concentrated in vacuo, and the residue was dissolved in EtOAc (300 mL) and washed with water (2×50 mL). The phases were separated, and the organic layer was dried (MgSO₄), filtered, and concentrated in vacuo. The residue obtained was crystallized from EtOAc to provide tert-butyl 4-(5-phenyl-1H-pyrazolo[3,4-b]pyridin-4-yl)piperazine-1-carboxylate (4.75 g, 49% yield) as a solid. LCMS (APCI+) m/z 380.1 (M+H)+, Retention time=3.66 minutes.

A mixture of tert-butyl 4-(5-phenyl-1H-pyrazolo[3,4-b]pyridin-4-yl)piperazine-1-carboxylate (3 g, 7.75 mmol) and powdered potassium hydroxide (1.28 g, 19.4 mmol) in DMF (20 mL) was treated with iodine (3.93 g, 15.5 mmol), and the mixture was heated at 60° C. After 4 hours, the mixture was cooled to room temperature and treated with powdered KOH (700 mg, 10.7 mmol) and I₂ (1.97 g, 7.75 mmol). The mixture was stirred at 60° C. for 1 hour. The mixture was cooled to room temperature, diluted with EtOAc (200 mL) and successively washed with saturated Na₂S₂O₃ solution (2×20 mL) and water (2×50 mL). The organic layer was separated, dried (MgSO₄), filtered, and concentrated in vacuo. The residue obtained was crystallized from boiling CH₃CN to provide tert-butyl 4-(3-iodo-5-phenyl-1H-pyrazolo[3,4-b]pyridin-4-yl)piperazine-1-carboxylate (3.12 g, 79.7% yield) as a solid. LCMS (APCI+) m/z 506 (M+H)+, Retention time=4.04 minutes.

1-(Chloromethyl)-4-methoxybenzene (1 mL, 7.36 mmol) was slowly added to a stirring mixture of tert-butyl 4-(3-iodo-5-phenyl-1H-pyrazolo[3,4-b]pyridin-4-yl)piperazine-1-carboxylate (3.1 g, 6.134 mmol) and K₂CO₃ (1.27 g, 9.2 mmol) in DMF (30 mL) at room temperature. After 2 hours, EtOAc (200 mL) and water (100 mL) were added to the mixture, and the phases were separated with warming. The resulting organic suspension was washed with water (3×50 mL) with warming. Final organic phase was concentrated in vacuo without drying over MgSO₄ to prevent the loss of the product. The residue was triturated with CH₃CN, and the solid formed was filtered, washed with CH₃CN (2×10 mL) and dried under high vacuum to provide tert-butyl 4-(3-iodo-1-(4-methoxybenzyl)-5-phenyl-1H-pyrazolo[3,4-b]pyridin-4-yl)piperazine-1-carboxylate (2.65 g, 69% yield) as a solid. LCMS (APCI+) m/z 626.1 (M+H)+, Retention time=4.96 minutes.

A 50 mL round bottom flask charged with tert-butyl 4-(3-iodo-1-(4-methoxybenzyl)-5-phenyl-1H-pyrazolo[3,4-b]pyridin-4-yl)piperazine-1-carboxylate (500 mg, 0.8 mmol), tri(o-tolyl)phosphine (18.25 mg, 0.06 mmol), Pd₂dba₃ (18.3 mg, 0.02 mmol), triethylamine (334 µL, 2.4 mmol), and DMF (7 mL) was purged under N₂ (3 cycles). Next, methyl acrylate (216 µL, 2.4 mmol) was added, and the mixture was stirred at 100° C. under N₂ atmosphere for 18 hours. The reaction mixture was cooled to room temperature, diluted with EtOAc (50 mL) and water (100 mL) was added. The phases were separated, and the organic layer was washed with water (3×30 mL), dried (MgSO₄), filtered, and concentrated in vacuo. The residue obtained was crystallized from CH₃CN to provide (E)-tert-butyl 4-(3-(3-methoxy-3-oxoprop-1-enyl)-1-(4-methoxybenzyl)-5-phenyl-1H-pyrazolo[3,4-b]pyridin-4-yl)piperazine-1-carboxylate (390 mg, 84% yield) as a solid. LCMS (APCI+) m/z 584.2 (M+H)+, Retention time=4.96 minutes.

A solution of (E)-tert-butyl 4-(3-(3-methoxy-3-oxoprop-1-enyl)-1-(4-methoxybenzyl)-5-phenyl-1H-pyrazolo[3,4-b]pyridin-4-yl)piperazine-1-carboxylate (380 mg, 0.65 mmol) in 25% TFA/CH₂Cl₂ was stirred at room temperature. Next, the solvent was removed, and the residue was evaporated from toluene (2×30 mL). Neat TFA (10 mL) was added to the resulting residue and heated at 60° C. for 4 hours. TFA was removed in vacuo, and the residue was evaporated from toluene (2×10 mL). 2M HCl in ether (5 mL) was added to the residue, and the mixture was sonicated for a few minutes. The solid formed was filtered, washed with ether (3×10 mL) and dried under high vacuum for 6 hours to provide (E)-methyl 3-(5-phenyl-4-(piperazin-1-yl)-1H-pyrazolo[3,4-b]pyridin-3-yl)acrylate hydrochloride salt (300 mg, 106% yield) as a solid. LCMS (APCI+) m/z 364.1 (M+H)+, Retention time=2.61 minutes.

Example R

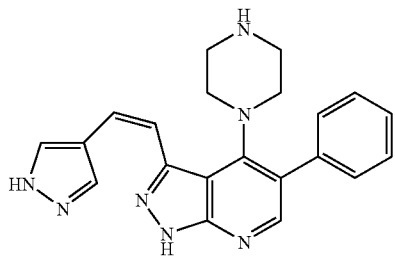 [SMILES: C(=C/c1n[nH]c2ncc(-c3ccccc3)c(N3CCNCC3)c12)/c1cn[nH]c1]

(Z)-3-(2-(1H-pyrazol-4-yl)vinyl)-5-phenyl-4-(piperazin-1-yl)-1H-pyrazolo[3,4-b]pyridine 4-Ethynyl-1-(4-methoxybenzyl)-1H-pyrazole (0.068 g, 0.32 mmol) was added to a solution of tert-butyl 4-(3-iodo-1-(4-methoxybenzyl)-5-phenyl-1H-pyrazolo[3,4-b]pyridin-4-yl)piperazine-1-carboxylate (0.10 g, 0.16 mmol), Cu(I)I (0.0015 g, 0.008 mmol), PdCl₂(PPh₃)₂ (0.0056 g, 0.008 mmol) and TEA (0.11 ml, 0.80 mmol) in THF (10 mL) and stirred at 40° C. for 18 hours. Water (10 mL) and ethyl acetate (20 mL) were added. The organic layer was separated, washed with brine, dried (sodium sulfate) and concentrated in vacuo. The residue obtained was purified by flash chromatography (hexane:ethyl acetate=5:1) to give tert-butyl 4-(1-(4-methoxybenzyl)-3-((1-(4-methoxybenzyl)-1H-pyrazol-4-yl)ethynyl)-5-phenyl-1H-pyrazolo[3,4-b]pyridin-4-yl)piperazine-1-carboxylate (0.134 g, 95%) as a solid. LCMS (APCI+) m/z 710 (M+H)+.

A solution of tert-butyl 4-(1-(4-methoxybenzyl)-3-((1-(4-methoxybenzyl)-1H-pyrazol-4-yl)ethynyl)-5-phenyl-1H-pyrazolo[3,4-b]pyridin-4-yl)piperazine-1-carboxylate (0.12 g, 0.169 mmol), quinoline (0.011 g, 0.085 mmol) and Lindlar's Catalyst (0.18 g, 0.085 mmol) in MeOH (3 mL) and benzene (3 mL) was charged with 1 atmosphere H₂ and stirred at room temperature for 6 hours. The catalyst was removed by filtration and washed with ethyl acetate. The filtrate was concentrated in vacuo, and the residue obtained was purified flash chromatography on silica gel (hexane:ethyl acetate=1:1) to give (Z)-tert-butyl 4-(1-(4-methoxybenzyl)-3-(2-(1-(4-methoxybenzyl)-1H-pyrazol-4-yl)vinyl)-5-phenyl-1H-pyrazolo[3,4-b]pyridin-4-yl)piperazine-1-carboxylate (0.089 g, 74%) as a solid.

(Z)-tert-Butyl 4-(1-(4-methoxybenzyl)-3-(2-(1-(4-methoxybenzyl)-1H-pyrazol-4-yl)vinyl)-5-phenyl-1H-pyrazolo[3,4-b]pyridin-4-yl)piperazine-1-carboxylate (0.084 g, 0.12 mmol) in DCM (1 mL) was added TFA (0.5 mL) and stirred at room temperature for 1 hour. The solvent was removed. The residue was dissolved in TFA (4 ml) and heated at 78° C. (bath) in a sealed tube overnight. The solvent was removed. The residue was dissolved in DCM (0.5 mL) and 2N HCl in ether (1 mL) was added. The solid formed was collected by filtration to give (Z)-3-(2-(1H-pyrazol-4-yl)vinyl)-5-phenyl-4-(piperazin-1-yl)-1H-pyrazolo[3,4-b]pyridine hydrochloride (0.051 g, 97%) as a solid.

Example S

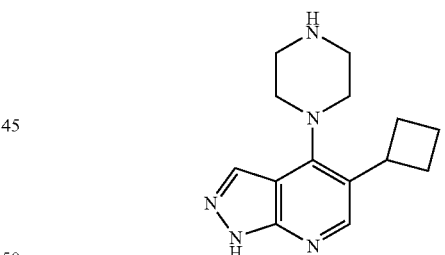

5-cyclobutyl-4-(piperazin-1-yl)-1H-pyrazolo[3,4-b]pyridine 1.7M t-BuLi in heptane (1.23 mL, 2.09 mmol) was added to a solution of tert-butyl 4-(5-bromo-1-(4-methoxybenzyl)-1H-pyrazolo[3,4-b]pyridin-4-yl)piperazine-1-carboxylate (0.50 g, 1.00 mmol) in THF (5 mL) at −78° C. The reaction was stirred at −78° C. for 30 minutes, and cyclobutanone (0.23 mL, 2.99 mmol) was added. The reaction mixture was allowed to warm to room temperature and stirred for 1 hour. Saturated NH₄Cl (10 mL) was added, extracted with ethyl acetate (30 mL), washed with brine, dried (sodium sulfate) and concentrated in vacuo. The residue was suspended in triethylsilane (2.31 g, 19.9 mmol), and TFA (2 mL) was added. After 1 hour, the solvent was removed, and the residue was dissolved in TFA (5 mL) and heated at 68° C. for 5 hours. The solvent was removed. The residue was dissolved in DCM (10 mL) and Boc$_2$O (0.434 g, 1.99 mmol) was added. The reaction was stirred at room temperature for 1 hour. The solvent was removed. The residue was dissolved in THF (5 mL) and 2N LiOH in water (5 mL) was added. It was stirred at room temperature for 2 hours. Ethyl acetate (50 mL) was added. The organic layer was separated, washed with brine, dried (sodium sulfate) and concentrated in vacuo. The residue obtained was purified by flash chromatography on silica gel (hexane:ethyl acetate=1:1) to give a solid. It was dissolved in EtOH (10 mL), and 10% Pd/C (0.11 g, 0.10 mmol) was added. The mixture was charged with 50 psi hydrogen and shaken for 6 hours. The catalyst was removed by filtration and concentrated in vacuo. The residue obtained was purified by flash chromatography (hexane:ethyl acetate=1:1) to give tert-butyl 4-(5-cyclobutyl-1H-pyrazolo[3,4-b]pyridin-4-yl)piperazine-1-carboxylate (0.14 g, 39%) as a solid. LCMS (APCI+) m/z 358(M+H)+.

TFA (0.60 mL, 7.83 mmol) was added to a solution of tert-butyl 4-(5-cyclobutyl-1H-pyrazolo[3,4-b]pyridin-4-yl)piperazine-1-carboxylate (0.14 g, 0.39 mmol) in DCM (10 mL) and stirred at room temperature for 1 hour. The solvent was removed. The resulting residue was dissolved in DCM (0.5 mL), and 2N HCl in ether (2 mL) was added. The solid formed was collected by filtration to give 5-cyclobutyl-4-(piperazin-1-yl)-1H-pyrazolo[3,4-b]pyridine hydrochloride (0.125 g, 97%).

Example 1

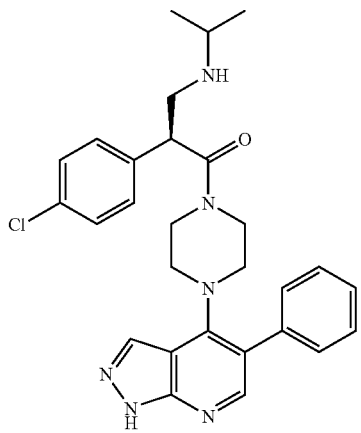 [SMILES: CC(C)NC[C@@H](C(=O)N1CCN(c2c(-c3ccccc3)cnc3[nH]ncc23)CC1)c1ccc(Cl)cc1]

(S)-2-(4-chlorophenyl)-3-(isopropylamino)-1-(4-(5-phenyl-1H-pyrazolo[3,4-b]pyridin-4-yl)piperazin-1-yl)propan-1-one Bromine (1.39 mL, 27.03 mmol) was added drop wise over 5 minutes to a solution of 1-(4-methoxybenzyl)-1H-pyrazolo[3,4-b]pyridin-4-ol (6.00 g, 23.50 mmol, prepared as described in WO 2007/103308) in absolute ethanol (60 mL) at 0° C. The reaction was stirred at 0° C. for 1 hour. 5% Sodium bicarbonate solution (100 mL) was then added, and the mixture was concentrated to give a slurry. The pH was next adjusted with 1N HCl to a pH of 4. The resulting solid was collected by filtration and dried. This solid was then suspended in ether (50 mL), stirred for 10 minutes, collected by filtration and dried to give 5-bromo-1-(4-methoxybenzyl)-1H-pyrazolo[3,4-b]pyridin-4-ol (6.8 g, 87%). MS ESI (+) m/z 334 detected. $^1$H NMR (400 Hz, DMSO-d6) δ 12.68 (s, 1H), 8.34 (s, 1H), 8.13 (s, 1H), 7.18 (d, J=8.8 Hz, 2H), 6.87 (d, J=8.4 Hz, 2H), 5.47 (s, 2H), 3.70 (s, 3H).

NaH (0.144 g, 3.59 mmol) in DMF (5 mL) was added dropwise to a solution of 5-bromo-1-(4-methoxybenzyl)-1H-pyrazolo[3,4-b]pyridin-4-ol (1.00 g, 2.99 mmol) in dimethylformamide ("DMF") (10 mL). The reaction mixture was warmed to 40° C. and stirred for 30 minutes. After cooling to room temperature, 1,1,1-trifluoro-N-phenyl-N-(trifluoromethylsulfonyl)methanesulfonamide (1.28 g, 3.59 mmol) was added and stirred at room temperature for 1 hour. tert-Butyl piperazine-1-carboxylate (1.23 g, 6.58 mmol) was then added. The mixture was warmed to 80° C. and stirred for 1 hour. The reaction was then cooled to room temperature, and a saturated ammonium chloride solution (30 mL) was added. The reaction mixture was extracted with ethyl acetate (2×20 mL) and dried over sodium sulfate, filtered and concentrated. The resulting residue was purified by column chromatography (hexane:ethyl acetate, 5:1) to give tert-butyl 4-(5-bromo-1-(4-methoxybenzyl)-1H-pyrazolo[3,4-b]pyridin-4-yl)piperazine-1-carboxylate (1.23 g, 82%) as a solid. MS ESI (+) m/z 504.3 detected. $^1$H NMR (400 Hz, DMSO-d6) δ 8.42 (s, 1H), 8.28 (s, 1H), 7.17 (d, J=8.8 Hz, 2H), 6.82 (d, J=8.8 Hz, 2H), 5.48 (s, 2H), 3.66 (s, 3H), 3.49 (m, 8H), 1.40 (s, 9H).

tert-Butyl 4-(5-bromo-1-(4-methoxybenzyl)-1H-pyrazolo[3,4-b]pyridin-4-yl)piperazine-1-carboxylate (0.50 g, 0.995 mmol), phenylboronic acid (0.182 g, 1.49 mmol), Pd(PPh$_3$)$_4$ (0.115 g, 0.0995 mmol) and Cs$_2$CO$_3$ (1.30 g, 3.98 mmol) were placed in dioxane:H$_2$O (8 mL, 3:1). The solution was heated to 80° C. for 6 hours. Ether (50 mL) and H$_2$O (20 mL) were then added. The organic layer was separated, washed with brine, dried over sodium sulfate, filtered and concentrated. The resulting residue was purified by column chromatography (DCM:ethyl acetate=5:1) to give tert-butyl 4-(1-(4-methoxybenzyl)-5-phenyl-1H-pyrazolo[3,4-b]pyridin-4-yl)piperazine-1-carboxylate (0.442 g, 89%) as a foam solid. MS ESI (+) m/z 500.4 detected. $^1$H NMR (400 Hz, DMSO-d6) δ 8.26 (s, 1H), 8.10 (s, 1H), 7.51 (m, 2H), 7.44 (m, 2H), 7.32 (m, 1H), 7.20 (d, J=8.4 Hz, 2H), 6.83 (d, J=8.4 Hz, 2H), 5.50 (s, 2H), 3.67 (s, 3H), 3.23 (m, 4H), 3.20 (m, 4H).

A solution of tert-butyl 4-(1-(4-methoxybenzyl)-5-phenyl-1H-pyrazolo[3,4-b]pyridin-4-yl)piperazine-1-carboxylate (0.440 g, 0.881 mmol) in DCM (5 mL) was added to TFA (1 mL) and stirred at room temperature for 1 hour. The reaction was then concentrated to dryness and dried under vacuum for 1 hour. TFA (3.39 mL, 44.0 mmol) was then added, and the mixture was stirred at 65° C. for 4 hours. The reaction was then concentrated to dryness, and the resulting residue was dissolved in DCM (3 mL). HCl in ether (2 mL, 2N) and ether (10 mL) were then added, and the resulting solid was collected by filtration to give 5-phenyl-4-(piperazin-1-yl)-1H-pyrazolo[3,4-b]pyridine dihydrochloride (0.29 g, 75%). MS ESI (+) m/z 280.1 detected.

DIEA (0.111 mL, 0.636 mmol) was added to a solution of 5-phenyl-4-(piperazin-1-yl)-1H-pyrazolo[3,4-b]pyridine dihydrochloride (0.070 g, 0.159 mmol), (S)-3-(tert-butoxycarbonyl(isopropyl)amino)-2-(4-chlorophenyl)propanoic acid (0.0543 g, 0.159 mmol, see Example B) and O-(benzotriazol-1-yl)-N,N,N,N'-tetramethyluronium tetrafluoroborate ("TBTU") (0.0613 g, 0.191 mmol) in DCM (1 mL) and stirred at room temperature for 1 hour. The mixture was then directly loaded onto a silica column and purified by chromatography (hexane:ethyl acetate, 1:1) to give (S)-tert-butyl 2-(4-chlorophenyl)-3-oxo-3-(4-(5-phenyl-1H-pyrazolo[3,4-b]pyridin-4-yl)piperazin-1-yl)propyl(isopropyl)carbamate as a solid. The solid was then dissolved in DCM (1 mL), and TFA (0.2 mL) was added. The mixture was stirred at room temperature for 1 hour and concentrated to dryness. The resulting residue was dissolved in DCM (0.5 mL), and HCl in ether (1 mL, 2N) was added. The resulting solid was collected by filtration to give (S)-2-(4-chlorophenyl)-3-(isopropylamino)-1-(4-(5-phenyl-1H-pyrazolo[3,4-b]pyridin-4-yl)piperazin-1-yl)propan-1-one dihydrochloride (0.044 g, 48%). MS ESI (+) m/z 503.4 detected.

Example 2

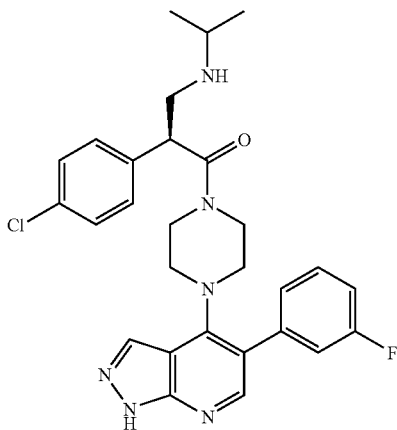 [SMILES: CC(C)NC[C@@H](C(=O)N1CCN(c2c(-c3cccc(F)c3)cnc3[nH]ncc23)CC1)c1ccc(Cl)cc1]

(S)-2-(4-chlorophenyl)-1-(4-(5-(3-fluorophenyl)-1H-pyrazolo[3,4-b]pyridin-4-yl)piperazin-1-yl)-3-(isopropylamino)propan-1-one A solution of tert-butyl 4-(5-bromo-1-(4-methoxybenzyl)-1H-pyrazolo[3,4-b]pyridin-4-yl)piperazine-1-carboxylate (0.30 g, 0.597 mmol, see Example 1), 3-fluorophenylboronic acid (0.125 g, 0.896 mmol), Pd(PPh$_3$)$_4$ (0.0690 g, 0.0597 mmol) and Cs$_2$CO$_3$ (0.778 g, 2.39 mmol) in dioxane:H$_2$O (8 mL, 3:1) was heated at 80° C. for 6 hours. Ether (50 mL) and H$_2$O (20 mL) were then added. The organic layer was separated, washed with brine and dried over sodium sulfate. After removal of solvent, the resulting residue was purified by column chromatography (DCM:ethyl acetate, 5:1) to give tert-butyl 4-(5-(3-fluorophenyl)-1-(4-methoxybenzyl)-1H-pyrazolo[3,4-b]pyridin-4-yl)piperazine-1-carboxylate (0.25 g, 81%) as a solid. MS ESI (+) m/z 518.4 detected. $^1$H NMR (400 Hz, DMSO-d6) δ 8.31 (s, 1H), 8.16 (s, 1H), 7.51 (m, 1H), 7.39 (m, 2H), 7.23 (d, J=8.8 Hz, 2H), 7.18 (m,1 H), 6.86 (d, J=8.8 Hz, 2H), 5.53 (s, 2H), 3.70 (s, 3H), 3.29 (m, 4H), 3.25 (m, 4H).

TFA (1 mL) was added to tert-butyl 4-(5-(3-fluorophenyl)-1-(4-methoxybenzyl)-1H-pyrazolo[3,4-b]pyridin-4-yl)piperazine-1-carboxylate (0.25 g, 0.483 mmol) in DCM (5 mL) and stirred at room temperature for 2 hours. The reaction was then concentrated to dryness and dried under vacuum for 3 hours. TFA (1.86 mL, 24.2 mmol) was then added, and the mixture was heated to 65° C. for 3 hours. The reaction was then concentrated to dryness. The resulting residue was dissolved in DCM (2 mL), and HCl in ether (2 mL, 2M) and ether (5 mL) were added. The resulting solid was collected by filtration to give 5-(3-fluorophenyl)-4-(piperazin-1-yl)-1H-pyrazolo[3,4-b]pyridine dihydrochloride (0.17 g, 94%). MS ESI (+) m/z 298.1 detected.

DIEA (d 0.742; 0.0790 mL, 0.454 mmol) was added to a solution of 5-(3-fluorophenyl)-4-(piperazin-1-yl)-1H-pyrazolo[3,4-b]pyridine dihydrochloride (0.070 g, 0.113 mmol), (S)-3-(tert-butoxycarbonyl(isopropyl)amino)-2-(4-chlorophenyl)propanoic acid (0.0388 g, 0.113 mmol, see Example B) and TBTU (0.0437 g, 0.136 mmol) in DCM (1 mL) and stirred at room temperature for 18 hours. The mixture was directly loaded onto a silica column and purified by chromatography (hexane:ethyl acetate, 1:1) to give (S)-tert-butyl 2-(4-chlorophenyl)-3-(4-(5-(3-fluorophenyl)-1H-pyrazolo[3,4-b]pyridin-4-yl)piperazin-1-yl)-3-oxopropyl(isopropyl)carbamate as a solid. The solid was dissolved in DCM (1 mL), and TFA (0.2 mL) was added. The mixture was stirred at room temperature for 1 hour and then concentrated to dryness. The resulting residue was dissolved in DCM (0.5 mL), and HCl in ether (1 mL, 2N) was added. The resulting solid was collected by filtration to give (S)-2-(4-chlorophenyl)-1-(4-(5-(3-fluorophenyl)-1H-pyrazolo[3,4-b]pyridin-4-yl)piperazin-1-yl)-3-(isopropylamino)propan-1-one dihydrochloride (0.022 g, 32%). MS APCI (+) m/z 521.4 detected.

Example 3

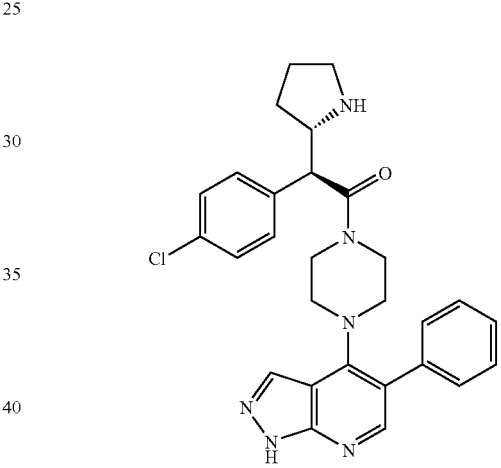

(S)-2-(4-chlorophenyl)-1-(4-(5-phenyl-1H-pyrazolo[3,4-b]pyridin-4-yl)piperazin-1-yl)-2-((S)-pyrrolidin-2-yl)ethanone DIEA (d 0.742; 0.0410 mL, 0.235 mmol) was added to a solution of 5-phenyl-4-(piperazin-1-yl)-1H-pyrazolo[3,4-b]pyridine dihydrochloride (0.0311 g, 0.0883 mmol, See Example 1), (S)-2-((S)-1-(tert-butoxycarbonyl)pyrrolidin-2-yl)-2-(4-chlorophenyl)acetic acid (0.020 g, 0.0589 mmol, see Example C) and TBTU (0.0227 g, 0.0706 mmol) in DCM (1 mL) and stirred at room temperature for 1 hour. The mixture was directly loaded onto a silica column and purified by chromatography (hexane:ethyl acetate, 1:1) to give (S)-tert-butyl 2-((S)-1-(4-chlorophenyl)-2-oxo-2-(4-(5-phenyl-1H-pyrazolo[3,4-b]pyridin-4-yl)piperazin-1-yl)ethyl)pyrrolidine-1-carboxylate as a solid. The solid was then dissolved in DCM (1 mL), and TFA (0.2 mL) was added. The mixture was stirred at room temperature for 1 hour and concentrated to dryness. The resulting residue was dissolved in DCM (0.5 mL), and HCl in ether (1 mL, 2N) was added. The resulting solid was collected by filtration to give (S)-2-(4-chlorophenyl)-1-(4-(5-phenyl-1H-pyrazolo[3,4-b]pyridin-4-yl)piperazin-1-yl)-2-((S)-pyrrolidin-2-yl)ethanone dihydrochloride (0.008 g, 24%). MS APCI (+) m/z 501.3 detected.

Example 4

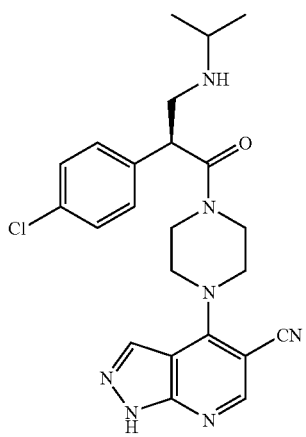 [SMILES: CC(C)NC[C@@H](C(=O)N1CCN(c2c(C#N)cnc3[nH]ncc23)CC1)c1ccc(Cl)cc1]

(S)-4-(4-(2-(4-chlorophenyl)-3-(isopropylamino) propanoyl)piperazin-1-yl)-1H-pyrazolo[3,4-b]pyridine-5-carbonitrile A solution of tert-butyl 4-(5-bromo-1-(4-methoxybenzyl)-1H-pyrazolo[3,4-b]pyridin-4-yl)piperazine-1-carboxylate (0.20 g, 0.398 mmol, see Example 1), Zn(CN)$_2$ (0.0304 g, 0.259 mmol), Zn dust (0.00625 g, 0.0955 mmol), Pd$_2$dba$_3$ (0.00729 g, 0.00796 mmol) and 1,1'-bis(diphenylphosphino) ferrocene ("dppf") (0.00883 g, 0.0159 mmol) in dimethylacetamide ("DMA"; 5 mL) were heated at 110° C. for 20 hours. Ether (50 mL) and H$_2$O (20 mL) were then added. The organic layer was separated, washed with brine and dried over sodium sulfate. After removal of the solvent, the resulting residue was purified by column chromatography (hexane: ethyl acetate, 1:1) to give tert-butyl 4-(5-cyano-1-(4-methoxybenzyl)-1H-pyrazolo[3,4-b]pyridin-4-yl)piperazine-1-carboxylate (0.16 g, 89%) as a solid. MS APCI (+) m/z 449.1 detected. $^1$H NMR (400 Hz, DMSO-d6) δ 8.47 (s, 1H), 7.20 (d, J=8.8 Hz, 2H), 6.86 (d, J=8.8 Hz, 2H), 5.51 (s, 2H), 3.88 (m, 4H), 3.70 (s, 3H), 3.58 (m, 4H).

TFA (1 mL) was added to tert-butyl 4-(5-cyano-1-(4-methoxybenzyl)-1H-pyrazolo[3,4-b]pyridin-4-yl)piperazine-1-carboxylate (0.158 g, 0.352 mmol) in DCM (5 mL) and stirred at room temperature for 1 hour. The reaction was then concentrated to dryness and dried under vacuum for 3 hours. TFA (1.1 mL, 14.7 mmol) was added, and the mixture was heated at 65° C. for 2 hours. The reaction was concentrated to dryness. The resulting residue was dissolved in DCM (3 mL), and HCl in ether (2 mL, 2M) and ether (5 mL) were added. The resulting solid was collected by filtration to give 4-(piperazin-1-yl)-1H-pyrazolo[3,4-b]pyridine-5-carbonitrile dihydrochloride (0.091 g, 70%). MS APCI (+) m/z 229.1 detected.

DIEA (d 0.742; 0.102 mL, 0.585 mmol) was added to a solution of 4-(piperazin-1-yl)-1H-pyrazolo[3,4-b]pyridine-5-carbonitrile dihydrochloride (0.0661 g, 0.219 mmol), (S)-3-(tert-butoxycarbonyl(isopropyl)amino)-2-(4-chlorophenyl)propanoic acid (0.050 g, 0.146 mmol, see Example B) and TBTU (0.0564 g, 0.176 mmol) in DCM (1 mL) and stirred at room temperature for 18 hours. The mixture was directly loaded onto a silica column and purified by chromatography (hexane:ethyl acetate, 1:1) to give (S)-tert-butyl 2-(4-chlorophenyl)-3-(4-(5-cyano-1H-pyrazolo[3,4-b]pyridin-4-yl)piperazin-1-yl)-3-oxopropyl(isopropyl)carbamate as a solid. The solid was dissolved in DCM (1 mL), and TFA (0.2 mL) was added. The mixture was stirred at room temperature for 1 hour and concentrated to dryness. The resulting residue was dissolved in DCM (0.5 mL), and HCl in ether (1 mL, 2N) was added. The resulting solid was collected by filtration to give (S)-4-(4-(2-(4-chlorophenyl)-3-(isopropylamino)propanoyl)piperazin-1-yl)-1H-pyrazolo[3,4-b]pyridine-5-carbonitrile dihydrochloride (0.043 g, 56%). MS APCI (+) m/z 452.1 detected.

Example 5

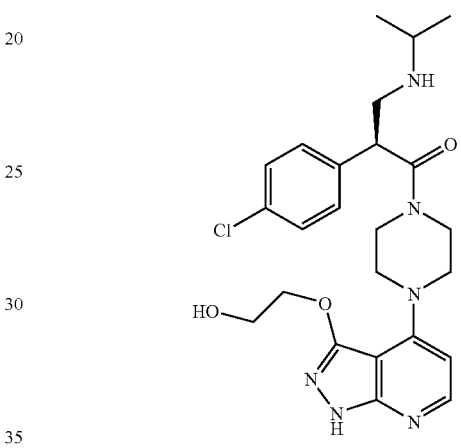

(S)-2-(4-chlorophenyl)-1-(4-(3-(2-hydroxyethoxy)-1H-pyrazolo[3,4-b]pyridin-4-yl)piperazin-1-yl)-3-(isopropylamino)propan-1-one NaH (0.188 g, 4.70 mmol) in DMF (5 mL) was added dropwise to 1-(4-methoxybenzyl)-1H-pyrazolo[3,4-b]pyridin-4-ol (1.00 g, 3.92 mmol, prepared as described in WO 2007/103308) in DMF (10 mL). The reaction mixture was then warmed to 40° C. and stirred for 30 minutes. After cooling to room temperature, 1,1,1-trifluoro-N-phenyl-N-(trifluoromethylsulfonyl)methanesulfonamide (1.68 g, 4.70 mmol) was added and stirred at room temperature for 1 hour. Then tert-butyl piperazine-1-carboxylate (1.61 g, 8.62 mmol) was added. The mixture was warmed to 80° C. and stirred for 3 hours. The reaction was then cooled to room temperature, and a saturated solution of NH$_4$Cl (30 mL) was added. The mixture was extracted with ethyl acetate (2×30 mL) and dried over sodium sulfate. After removal of solvent, the resulting residue was purified by column chromatography (hexane: ethyl acetate, 5:1) to give tert-butyl 4-(1-(4-methoxybenzyl)-1H-pyrazolo[3,4-b]pyridin-4-yl)piperazine-1-carboxylate (1.64 g, 99% yield) as a solid. MS APCI (+) m/z 424.1 detected. $^1$H NMR (400 Hz, DMSO-d6) δ 8.24 (s, 1H), 8.13 (d, J=5.2 Hz, 1H), 7.18 (d, J=8.4 Hz, 2H), 6.84 (d, J=8.4 Hz, 2H), 6.42 (d, J=5.2 Hz, 1H), 5.49 (s, 2H), 3.69 (s, 3H), 3.64 (m, 4H), 3.53 (m, 4H).

TFA (6 mL) was added to tert-butyl 4-(1-(4-methoxybenzyl)-1H-pyrazolo[3,4-b]pyridin-4-yl)piperazine-1-carboxylate (1.59 g, 3.754 mmol) in DCM (30 mL) and stirred at room temperature for 1 hour. The reaction was then concentrated to dryness and dried under vacuum for 3 hours. TFA (8.68 mL, 112.6 mmol) was added, and the mixture was heated at 65° C. for 2 hours. The reaction was then concentrated to dryness. The resulting residue was added to THF (10 mL), a LiOH solution (3.8 mL, 7.5 mmol, 2N) and Boc₂O (0.98 g, 4.50 mmol) and stirred at room temperature for 1 hour. Ether (20 mL) and water (10 mL) were then added. The organic layer was separated, washed with brine, and dried over sodium sulfate. After removal of solvent, the resulting residue was purified by chromatography (hexane:ethyl acetate, 3:1) to give tert-butyl 4-(1H-pyrazolo[3,4-b]pyridin-4-yl)piperazine-1-carboxylate (0.55 g, 48%) as a solid. MS APCI (+) m/z 304.1 detected. ¹H NMR (400 Hz, DMSO-d6) δ 8.21 (s, 1H), 8.08 (d, J=5.6 Hz, 1H), 6.37 (d, J=5.6 Hz, 1H), 3.60 (m, 4H), 3.54 (m, 4H), 2.50 (s, 9H).

I₂ (0.920 g, 3.63 mmol) was added to tert-butyl 4-(1H-pyrazolo[3,4-b]pyridin-4-yl)piperazine-1-carboxylate (0.55 g, 1.81 mmol) and KOH (0.305 g, 5.44 mmol) (crushed by motar and pestle) in DMF (10 mL). The resulting mixture was warmed to 60° C. and stirred for 2 hours. Ether (20 mL) and saturated Na₂SO₃ (10 mL) were then added. The organic layer was separated, washed with brine and dried over sodium sulfate. After removal of the solvent, the resulting residue was purified by chromatography (hexane:ethyl acetate, 3:1) to give tert-butyl 4-(3-iodo-1H-pyrazolo[3,4-b]pyridin-4-yl) piperazine-1-carboxylate (0.45 g, 58%) as a solid. MS APCI (+) m/z 430.0 detected. ¹H NMR (400 Hz, DMSO-d6) δ 8.31 (d, J=5.2 Hz, 1H), 6.63 (d, J=5.6 Hz, 1H), 3.63 (m, 4H), 3.18 (m, 4H), 1.44 (s, 9H).

1-(Chloromethyl)-4-methoxybenzene (0.219 mL, 1.61 mmol) was added to tert-butyl 4-(3-iodo-1H-pyrazolo[3,4-b] pyridin-4-yl)piperazine-1-carboxylate (0.575 g, 1.34 mmol) and K₂CO₃ (0.222 g, 1.61 mmol) in DMF (10 mL). The reaction was stirred at room temperature for 2 hours. Ether (30 mL) and water (10 mL) were added. The organic layer was separated, washed with brine, and dried over sodium sulfate. After removal of the solvent, the resulting residue was purified by chromatography (hexane:ethyl acetate, 3:1) to give tert-butyl 4-(3-iodo-1-(4-methoxybenzyl)-1H-pyrazolo [3,4-b]pyridin-4-yl)piperazine-1-carboxylate (0.59 g, 80%) as a solid. MS APCI (+) m/z 549.7 detected. ¹H NMR (400 Hz, DMSO-d6) δ 8.37 (d, J=5.2 Hz, 1H), 7.21 (d, J=8.4 Hz, 2H), 6.87 (d, J=8.4 Hz, 2H), 6.68 (d, J=5.2 Hz, 1H), 5.53 (s, 2H), 3.70 (s, 3H), 3.62 (m, 4H), 3.19 (m, 4H), 1.43 (s, 9H).

tert-Butyl 4-(3-iodo-1-(4-methoxybenzyl)-1H-pyrazolo [3,4-b]pyridin-4-yl)piperazine-1-carboxylate (0.12 g, 0.218 mmol), Cu(I)I (0.0416 g, 0.218 mmol), 1,10-phenanthroline (0.0394 g, 0.218 mmol), 2-tert-butoxyethanol (0.774 g, 6.55 mmol) and KF on Al₂O₃ (40%; 0.222 g, 1.53 mmol) in toluene (4 mL) were stirred at 120° C. for 40 hours. The reaction was then cooled to room temperature. Ethyl acetate (10 mL) was then added. The reaction was filtered through a pad of celite and concentrated to dryness. The resulting residue was purified by chromatography (hexane:ethyl acetate, 3:1) to give tert-butyl 4-(3-(2-tert-butoxyethoxy)-1-(4-methoxybenzyl)-1H-pyrazolo[3,4-b]pyridin-4-yl)piperazine-1-carboxylate (0.080 g, 68%) as a solid. MS APCI (+) m/z 540.5 detected.

TFA (1 mL) was added to tert-butyl 4-(3-(2-tert-butoxyethoxy)-1-(4-methoxybenzyl)-1H-pyrazolo[3,4-b]pyridin-4-yl)piperazine-1-carboxylate (0.080 g, 0.148 mmol) in DCM (1 mL) and stirred at room temperature for 4 hours. The reaction was then concentrated to dryness and dried under vacuum for 3 hours. TFA (2 mL) was then added, and the mixture was heated at 100° C. in a sealed tube for 18 hours. The reaction was then cooled to room temperature and concentrated to dryness. The resulting residue was dissolved in DCM (2 mL), and HCl in ether (1 mL, 2N) was added. The resulting solid was collected by filtration to give 2-(4-(piperazin-1-yl)-1H-pyrazolo[3,4-b]pyridin-3-yloxy)ethanol dihydrochloride (0.050 g, 100%).

DIEA (0.0815 mL, 0.468 mmol) was added to 2-(4-(piperazin-1-yl)-1H-pyrazolo[3,4-b]pyridin-3-yloxy)ethanol dihydrochloride (0.0472 g, 0.140 mmol), (S)-3-(tert-butoxycarbonyl(isopropyl)amino)-2-(4-chlorophenyl)propanoic acid (0.234 mL, 0.117 mmol, see Example B) and TBTU (0.0451 g, 0.140 mmol) in DCM (1 mL) and stirred at room temperature for 1 hour. The reaction was concentrated to dryness. The resulting residue was dissolved in THF/MeOH (2 mL, 1:1). A LiOH solution (1 mL, 2M) was added and stirred for 10 minutes. Ether (20 mL) was added. The organic layer was separated, washed with brine (5 mL), and dried over sodium sulfate. After removal of the solvent, the resulting residue was purified by chromatography (ethyl acetate) to give (S)-tert-butyl 2-(4-chlorophenyl)-3-(4-(3-(2-hydroxyethoxy)-1H-pyrazolo[3,4-b]pyridin-4-yl)piperazin-1-yl)-3-oxopropyl(isopropyl)carbamate as a solid. The solid was then dissolved in DCM (1 mL), and TFA (0.4 mL) was added. The mixture was stirred at room temperature for 1 hour and then concentrated to dryness. The resulting residue was dissolved in DCM (0.5 mL), and HCl in ether (1 mL, 2N) was added. The solvent was removed, and the resulting solid was dissolved in MeOH (2 mL). A LiOH solution (2 mL, 2M) was added and stirred for 10 minutes. DCM (20 mL) and water (10 mL) were added. The organic layer was separated, dried over sodium sulfate and concentrated to give (S)-2-(4-chlorophenyl)-1-(4-(3-(2-hydroxyethoxy)-1H-pyrazolo[3,4-b]pyridin-4-yl)piperazin-1-yl)-3-(isopropylamino)propan-1-one (0.018 g, 32%) as a solid. MS APCI (+) m/z 487.3 detected.

Example 6

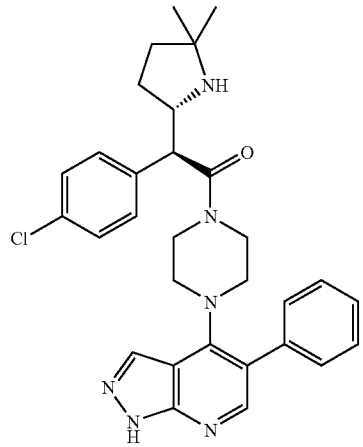 [SMILES: CC1(C)CC[C@@H]([C@@H](C(=O)N2CCN(c3c(-c4ccccc4)cnc4[nH]ncc34)CC2)c2ccc(Cl)cc2)N1]

(S)-2-(4-chlorophenyl)-2-((S)-5,5-dimethylpyrrolidin-2-yl)-1-(4-(5-phenyl-1H-pyrazolo[3,4-b]pyridin-4-yl)piperazin-1-yl)ethanone DIEA (0.0475 mL, 0.273 mmol) was added to a solution of 5-phenyl-4-(piperazin-1-yl)-1H-pyrazolo[3,4-b]pyridine dihydrochloride (0.030 g, 0.0681 mmol, See Example 1), (S)-2-((S)-1-(tert-butoxycarbonyl)-5,5-dimethylpyrrolidin-2-yl)-2-(4-chlorophenyl)acetic acid (0.0251 g, 0.0681 mmol, see Example D) and TBTU (0.0263 g, 0.0818 mmol) in DCM (1 mL) and stirred at room temperature for 16 hours. The mixture was directly loaded onto a silica column and purified by chromatography (hexane:ethyl acetate, 1:1) to give (S)-tert-butyl 5-((S)-1-(4-chlorophenyl)-2-oxo-2-(4-(5-phenyl-1H-pyrazolo[3,4-b]pyridin-4-yl)piperazin-1-yl)ethyl)-2,2-dimethylpyrrolidine-1-carboxylate as a solid. The solid was dissolved in DCM (1 mL), and TFA (0.2 mL) was added. The mixture was stirred at room temperature for 1 hour and then concentrated to dryness. The resulting residue was dissolved in DCM (0.5 mL), and HCl in ether (1 mL, 2N) was added. The resulting solid was collected by filtration to give (S)-2-(4-chlorophenyl)-2-((S)-5,5-dimethylpyrrolidin-2-yl)-1-(4-(5-phenyl-1H-pyrazolo[3,4-b]pyridin-4-yl)piperazin-1-yl)ethanone (0.019, 46%). MS APCI (+) m/z 529.3 detected.

Example 7

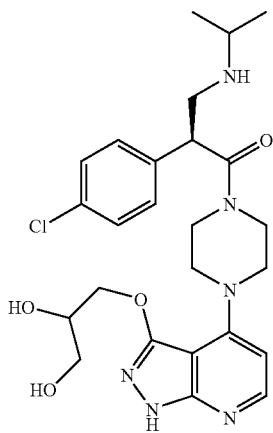 [SMILES: CC(C)NC[C@@H](C(=O)N1CCN(c2ccnc3[nH]nc(OCC(O)CO)c23)CC1)c1ccc(Cl)cc1]

(2S)-2-(4-chlorophenyl)-1-(4-(3-(2,3-dihydroxypropoxy)-1H-pyrazolo[3,4-b]pyridin-4-yl)piperazin-1-yl)-3-(isopropylamino)propan-1-one A mixture of tert-Butyl 4-(3-iodo-1-(4-methoxybenzyl)-1H-pyrazolo[3,4-b]pyridin-4-yl)piperazine-1-carboxylate (0.12 g, 0.218 mmol, see Example 5), Cu(I)I (0.0416 g, 0.218 mmol), 1,10-phenanthroline (0.0393 g, 0.218 mmol), (2,2-dimethyl-1,3-dioxolan-4-yl)methanol (0.812 mL, 6.55 mmol) and KF on Al$_2$O$_3$ (40%; 0.222 g, 1.53 mmol) in toluene (4 mL) was stirred at 120° C. for 75 hours. Ethyl acetate (10 mL) was then added, and the reaction was filtered through a pad of celite. The filtrate was then concentrated to dryness. The resulting residue was purified by chromatography (hexane:ethyl acetate, 1:1) to give tert-butyl 4-(3-((2,2-dimethyl-1,3-dioxolan-4-yl)methoxy)-1-(4-methoxybenzyl)-1H-pyrazolo[3,4-b]pyridin-4-yl)piperazine-1-carboxylate (0.068 g, 56%) as a solid. MS APCI (+) m/z 554.4 detected.

TFA (1 mL) was added to tert-butyl 4-(3-((2,2-dimethyl-1,3-dioxolan-4-yl)methoxy)-1-(4-methoxybenzyl)-1H-pyrazolo[3,4-b]pyridin-4-yl)piperazine-1-carboxylate (0.068 g, 0.123 mmol) in DCM (1 mL) and stirred at room temperature for 2 hours. The reaction was then concentrated to dryness and dried under vacuum for 1 hour. TFA (2 mL) was added, and the mixture was heated at 100° C. in a sealed tube for 20 hours. The reaction was concentrated to dryness. The resulting residue was dissolved in DCM (1 mL), and HCl in ether (1 mL, 2N) was added. The resulting solid was collected by filtration to give 3-(4-(piperazin-1-yl)-1H-pyrazolo[3,4-b]pyridin-3-yloxy)propane-1,2-diol dihydrochloride (0.042 g, 70%). MS APCI (+) m/z 294.2 detected.

DIEA (0.0514 mL, 0.295 mmol) was added to 3-(4-(piperazin-1-yl)-1H-pyrazolo[3,4-b]pyridin-3-yloxy)propane-1,2-diol dihydrochloride (0.030 g, 0.0737 mmol), (S)-3-(tert-butoxycarbonyl(isopropyl)amino)-2-(4-chlorophenyl)propanoic acid (0.0252 g, 0.0737 mmol, see Example B) and TBTU (0.0284 g, 0.0885 mmol) in DCM (1 mL) and stirred at room temperature for 2 hours. The reaction was concentrated to dryness. The resulting residue was dissolved in THF:MeOH (2 mL, 1:1), and a LiOH solution (1 mL, 2M) was added. The solution was stirred for 30 minutes, followed by the addition of ether (20 mL). The organic layer was separated, washed with brine (10 mL), and dried over sodium sulfate. After removal of the solvent, the resulting residue was purified by column chromatography (ethyl acetate:MeOH, 20:1) to give tert-butyl(2S)-2-(4-chlorophenyl)-3-(4-(3-(2,3-dihydroxypropoxy)-1H-pyrazolo[3,4-b]pyridin-4-yl)piperazin-1-yl)-3-oxopropyl(isopropyl)carbamate as a solid. The solid was dissolved in DCM (1 mL), and TFA (0.4 mL) was added. The mixture was stirred at room temperature for 1 hour and then concentrated to dryness. The resulting residue was dissolved in DCM (0.5 mL), and 2N HCl in ether (1 mL) was added. The resulting solid was collected by filtration to give (2S)-2-(4-chlorophenyl)-1-(4-(3-(2,3-dihydroxypropoxy)-1H-pyrazolo[3,4-b]pyridin-4-yl)piperazin-1-yl)-3-(isopropylamino)propan-1-one dihydrochloride (0.014 g, 33%). MS APCI (+) m/z 517.2 detected.

Example 8

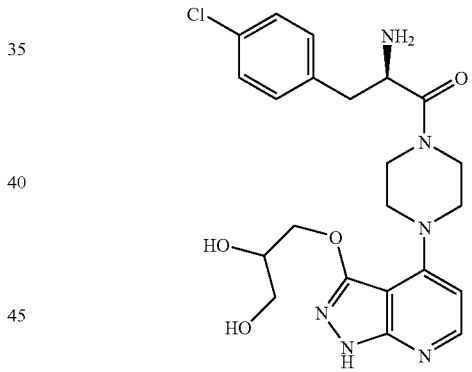

(2R)-2-amino-3-(4-chlorophenyl)-1-(4-(3-(2,3-dihydroxypropoxy)-1H-pyrazolo[3,4-b]pyridin-4-yl)piperazin-1-yl)propan-1-one DIEA (0.0514 mL, 0.295 mmol) was added to 3-(4-(piperazin-1-yl)-1H-pyrazolo[3,4-b]pyridin-3-yloxy)propane-1,2-diol dihydrochloride (0.030 g, 0.0737 mmol, see Example 7), (R)-2-(tert-butoxycarbonylamino)-3-(4-chlorophenyl)propanoic acid (0.022 g, 0.074 mmol) and TBTU (0.0284 g, 0.0885 mmol) in DCM (1 mL) and stirred at room temperature for 1 hour. The reaction was concentrated to dryness. The resulting residue was dissolved in THF/MeOH (2 mL, 1:1), and a LiOH solution (1 mL, 2M) was added. The solution was stirred for 30 minutes. Ether (20 mL) was then added. The organic layer was separated, washed with brine (10 mL), and dried over sodium sulfate. After removal of solvent, the resulting residue was purified by chromatography (ethyl acetate:MeOH, 20:1) to give tert-butyl(2R)-3-(4-chlorophenyl)-1-(4-(3-(2,3-dihydroxypropoxy)-1H-pyrazolo[3,4-b]pyridin-4-yl)piperazin-1-yl)-1-oxopropan-2-ylcarbamate as a solid. The solid was dissolved in DCM (1 mL), and TFA (0.4 mL) was added. The mixture was stirred at room temperature for 1 hour and then concentrated to dryness. The resulting residue was dissolved in DCM (0.5 mL), and HCl in ether (1 mL, 2N) was added. The resulting solid was collected by filtration to give (2R)-2-amino-3-(4-chlorophenyl)-1-(4-(3-(2,3-dihydroxypropoxy)-1H-pyrazolo[3,4-b]pyridin-4-yl)piperazin-1-yl)propan-1-one (0.010 g, 25%). MS APCI (+) m/z 475.2 detected.

Example 9

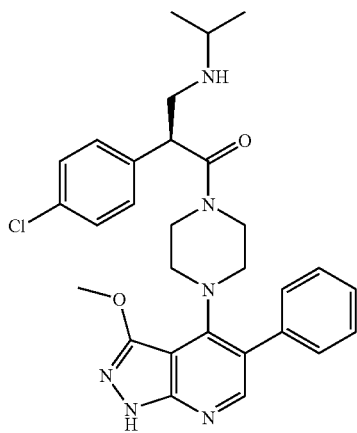 [SMILES: COc1n[nH]c2ncc(-c3ccccc3)c(N3CCN(C(=O)[C@H](CNC(C)C)c4ccc(Cl)cc4)CC3)c12]

(S)-2-(4-chlorophenyl)-3-(isopropylamino)-1-(4-(3-methoxy-5-phenyl-1H-pyrazolo[3,4-b]pyridin-4-yl)piperazin-1-yl)propan-1-one TFA (3 mL) was added to tert-butyl 4-(1-(4-methoxybenzyl)-5-phenyl-1H-pyrazolo[3,4-b]pyridin-4-yl)piperazine-1-carboxylate (1.7 g, 3.40 mmol, see Example 1) in DCM (10 mL) and stirred at room temperature for 2 hours. The reaction was concentrated to dryness and dried under vacuum for 3 hours. TFA (13.1 mL, 170 mmol) was then added, and the mixture was heated at 65° C. for 1 hour. The reaction was then concentrated to dryness. The resulting residue was added to THF (10 mL), an aqueous LiOH solution (6.81 mL, 2M) and $Boc_2O$ (2.23 g, 10.2 mmol) and stirred at room temperature for 3 days. Ether (50 mL) was then added. The organic layer was separated, washed with brine, and dried over sodium sulfate. After removal of the solvent, the resulting residue was purified by column chromatography (hexane:ethyl acetate, 1:1) to give tert-butyl 4-(5-phenyl-1H-pyrazolo[3,4-b]pyridin-4-yl)piperazine-1-carboxylate (1.1 g, 85%) as a solid. MS APCI (+) m/z 380.1 detected.

$I_2$ (0.421 g, 1.66 mmol) was added to a solution of tert-butyl 4-(5-phenyl-1H-pyrazolo[3,4-b]pyridin-4-yl)piperazine-1-carboxylate (0.63 g, 0.830 mmol) and KOH (0.140 g, 2.49 mmol) (crushed by mortar and pestle) in DMF (10 mL). The resulting mixture was heated to 60° C. for 3 hours. Ether (20 mL) and saturated $Na_2SO_3$ (10 mL) were then added. The organic layer was separated, washed with brine, and dried over sodium sulfate. After removal of the solvent, the resulting residue was purified by chromatography (hexane:ethyl acetate, 3:1) to give tert-butyl 4-(3-iodo-5-phenyl-1H-pyrazolo[3,4-b]pyridin-4-yl)piperazine-1-carboxylate (0.40 g, 95%) as a solid. MS APCI (+) m/z 506.2 detected. $^1$H NMR (400 Hz, DMSO-d6) δ 8.30 (s, 1H), 7.60 (m, 3H), 7.49 (m, 2H), 3.63 (m, 4H), 2.95 (m, 4H), 1.51 (s, 9H).

1-(Chloromethyl)-4-methoxybenzene (0.128 mL, 0.938 mmol) was added to tert-butyl 4-(3-iodo-5-phenyl-1H-pyrazolo[3,4-b]pyridin-4-yl)piperazine-1-carboxylate (0.395 g, 0.782 mmol) and $K_2CO_3$ (0.130 g, 0.938 mmol) in DMF (10 mL). The reaction was stirred at room temperature for 2 hours. Ether (30 mL) and water (10 mL) were then added. The organic layer was separated, washed with brine, and dried over sodium sulfate. After removal of the solvent, the resulting residue was purified by column chromatography (hexane:ethyl acetate, 3:1) to give tert-butyl 4-(3-iodo-1-(4-methoxybenzyl)-5-phenyl-1H-pyrazolo[3,4-b]pyridin-4-yl)piperazine-1-carboxylate (0.33 g, 68%) as a solid. $^1$H NMR (400 Hz, $CD_2Cl_2$) δ 8.23 (s, 1H), 7.44 (m, 3H), 7.33 (d, J=8.8 Hz, 2H), 7.26 (m, 2H), 6.84 (d, J=8.8 Hz, 2H), 5.59 (s, 2H), 3.76 (s, 3H), 3.55 (m, 4H), 2.86 (m, 4H), 1.40 (s, 9H).

tert-Butyl 4-(3-iodo-1-(4-methoxybenzyl)-5-phenyl-1H-pyrazolo[3,4-b]pyridin-4-yl)piperazine-1-carboxylate (0.12 g, 0.192 mmol), Cu(I)I (0.0365 g, 0.192 mmol), 1,10-phenanthroline (0.0346 g, 0.192 mmol), methanol (0.389 mL, 9.59 mmol) and KF on $Al_2O_3$ (40%; 0.195 g, 1.34 mmol) in toluene (4 mL) was stirred at 110° C. for 20 hours. The reaction was cooled to room temperature. Ethyl acetate (10 mL) was then added, and the reaction mixture was filtered through a pad of celite. The filtrate was concentrated to dryness. The resulting residue was purified by column chromatography (hexane:ethyl acetate, 1:1) to give tert-butyl 4-(3-methoxy-1-(4-methoxybenzyl)-5-phenyl-1H-pyrazolo[3,4-b]pyridin-4-yl)piperazine-1-carboxylate (0.098 g, 96%) as a solid. MS APCI (+) m/z 530.4 detected. $^1$H NMR (400 Hz, DMSO-d6) δ 8.06 (s, 1H), 7.46 (m, 2H), 7.33 (m, 3H), 7.20 (d, J=8.8 Hz, 2H), 6.87 (d, J=8.8 Hz, 2H), 5.38 (s, 2H), 3.98 (s, 3H), 3.71 (s, 3H), 3.29 (m, 4H), 2.94 (m, 4H), 1.37 (s, 9H).

TFA (0.5 mL) was added to tert-butyl 4-(3-methoxy-1-(4-methoxybenzyl)-5-phenyl-1H-pyrazolo[3,4-b]pyridin-4-yl)piperazine-1-carboxylate (0.098 g, 0.185 mmol) in DCM (2 mL) and stirred at room temperature for 2 hours. The reaction mixture was then concentrated to dryness. The resulting residue was dissolved in TFA (2.85 mL, 37.01 mmol) and heated at 100° C. in a sealed tube for 5 hours. The reaction mixture was again concentrated to dryness. The resulting residue was dissolved in DCM (0.5 mL), followed by the addition of HCl in ether (2 mL, 2N). The resulting solid was collected by filtration to give 3-methoxy-5-phenyl-4-(piperazin-1-yl)-1H-pyrazolo[3,4-b]pyridine (0.068 g, 96%). MS APCI (+) m/z 310.1 detected.

DIEA (0.0558 mL, 0.320 mmol) was added to 3-methoxy-5-phenyl-4-(piperazin-1-yl)-1H-pyrazolo[3,4-b]pyridine dihydrochloride (0.034 g, 0.080 mmol), 2-(1H-benzo[d][1,2,3]triazol-1-yl)-1,1,3,3-tetramethyluronium tetrafluoroborate (0.0308 g, 0.0961 mmol) and (S)-3-(tert-butoxycarbonyl(isopropyl)amino)-2-(4-chlorophenyl)propanoic acid (0.0274 g, 0.080 mmol, see Example B) in DCM (1 mL) and stirred at room temperature for 1 hour. The reaction was concentrated to dryness. The resulting residue was dissolved in THF/MeOH (2 mL, 1:1), and an aqueous LiOH solution (1 mL, 2M) was added. It was stirred for 30 minutes, and then ether (20 mL) was added. The organic layer was separated, washed with brine (10 mL), and dried over sodium sulfate. After removal of solvent, the resulting residue was purified by column chromatography (hexane:ethyl acetate, 1:1) to give (S)-tert-butyl 2-(4-chlorophenyl)-3-(4-(3-methoxy-5-phenyl-1H-pyrazolo[3,4-b]pyridin-4-yl)piperazin-1-yl)-3-oxopropyl(isopropyl)carbamate as a solid. The solid was then dissolved in DCM (1 mL), and TFA (0.4 mL) was added. The mixture was stirred at room temperature for 2 hours and concentrated to dryness. The resulting residue was dissolved in DCM (0.5 mL), and HCl in ether (1 mL, 2N) was added. The resulting solid was collected by filtration to give (S)-2-(4-chlorophenyl)-3-(isopropylamino)-1-(4-(3-methoxy-5-phenyl-1H-pyrazolo[3,4-b]pyridin-4-yl)piperazin-1-yl)propan-1-one dihydrochloride (0.029 g, 60%). MS APCI (+) m/z 533.3 detected.

Example 10

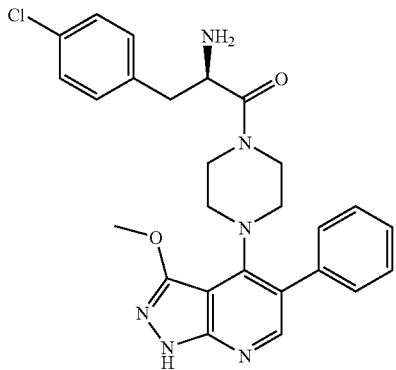 [SMILES: COc1n[nH]c2ncc(-c3ccccc3)c(N3CCN(C(=O)[C@H](N)Cc4ccc(Cl)cc4)CC3)c12]

((R)-2-amino-3-(4-chlorophenyl)-1-(4-(3-methoxy-5-phenyl-1H-pyrazolo[3,4-b]pyridin-4-yl)piperazin-1-yl)propan-1-one DIEA (0.0558 mL, 0.320 mmol) was added to 3-methoxy-5-phenyl-4-(piperazin-1-yl)-1H-pyrazolo[3,4-b]pyridine dihydrochloride (0.034 g, 0.080 mmol, see Example 9), (R)-2-(tert-butoxycarbonylamino)-3-(4-chlorophenyl)propanoic acid (0.024 g, 0.080 mmol) and TBTU (0.0308 g, 0.0961 mmol) in DCM (1 mL) and stirred at room temperature for 1 hour. The reaction was then concentrated to dryness. The resulting residue was dissolved in THF/MeOH (2 mL, 1:1), and an aqueous LiOH solution (1 mL, 2M) was added. It was stirred for 20 minutes, and then ether (20 mL) was added. The organic layer was separated, washed with brine (10 mL), and dried over sodium sulfate. After removal of the solvent, the resulting residue was purified by chromatography (hexane:ethyl acetate, 1:1) to give (R)-tert-butyl 3-(4-chlorophenyl)-1-(4-(3-methoxy-5-phenyl-1H-pyrazolo[3,4-b]pyridin-4-yl)piperazin-1-yl)-1-oxopropan-2-ylcarbamate as a solid. The solid was dissolved in DCM (1 mL), and TFA (0.4 mL) was added. The mixture was stirred at room temperature for 2 hours and then concentrated to dryness. The resulting residue was dissolved in DCM (0.5 mL), and HCl in ether (1 mL, 2N) was added. The resulting solid was collected by filtration to give (R)-2-amino-3-(4-chlorophenyl)-1-(4-(3-methoxy-5-phenyl-1H-pyrazolo[3,4-b]pyridin-4-yl)piperazin-1-yl)propan-1-one (0.036 g, 79%). MS APCI (+) m/z 491.3 detected.

Example 11

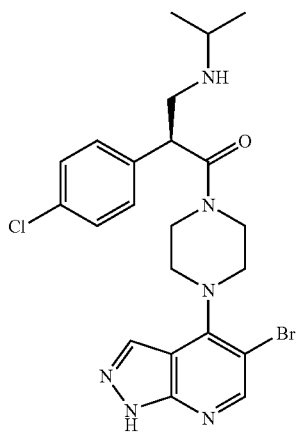 [SMILES: CC(C)NC[C@@H](C(=O)N1CCN(c2c(Br)cnc3[nH]ncc23)CC1)c1ccc(Cl)cc1]

(S)-1-(4-(5-bromo-1H-pyrazolo[3,4-b]pyridin-4-yl)piperazin-1-yl)-2-(4-chlorophenyl)-3-(isopropylamino)propan-1-one TFA (0.5 mL) was added to a solution of tert-butyl 4-(5-bromo-1-(4-methoxybenzyl)-1H-pyrazolo[3,4-b]pyridin-4-yl)piperazine-1-carboxylate (0.10 g, 0.20 mmol, see Example 1) in DCM (2 mL) and stirred at room temperature for 1 hour. The reaction mixture was then concentrated to dryness. The resulting residue was dissolved in TFA (3.067 mL, 39.81 mmol) and heated at 60° C. for 3 hours. The reaction was concentrated to dryness. The resulting residue was dissolved in DCM (0.5 mL), and HCl in ether (2 mL, 2N) was added. The resulting solid was collected by filtration to give 5-bromo-4-(piperazin-1-yl)-1H-pyrazolo[3,4-b]pyridine dihydrochloride (0.050 g, 70%). MS APCI (+) m/z 282.0 detected.

DIEA (0.0687 mL, 0.394 mmol) was added to 5-bromo-4-(piperazin-1-yl)-1H-pyrazolo[3,4-b]pyridine dihydrochloride (0.050 g, 0.0986 mmol), 2-(1H-benzo[d][1,2,3]triazol-1-yl)-1,1,3,3-tetramethyluronium tetrafluoroborate (0.0380 g, 0.118 mmol) and (S)-3-(tert-butoxycarbonyl(isopropyl)amino)-2-(4-chlorophenyl)propanoic acid (0.0337 g, 0.0986 mmol, see Example B) in DCM (1 mL) and stirred at room temperature for 16 hours. The reaction was concentrated to dryness. The resulting residue was dissolved in THF/MeOH (2 mL, 1:1), and a LiOH solution (1 mL, 2M) was added. The solution was stirred for 30 minutes, and then ether (20 mL) was added. The organic layer was separated, washed with brine (10 mL), and dried over sodium sulfate. After removal of the solvent, the resulting residue was purified by column chromatography (hexane:ethyl acetate, 1:1) to give (S)-tert-butyl 3-(4-(5-bromo-1H-pyrazolo[3,4-b]pyridin-4-yl)piperazin-1-yl)-2-(4-chlorophenyl)-3-oxopropyl(isopropyl)carbamate as a solid. The solid was dissolved in DCM (1 mL), and TFA (0.4 mL) was added. The mixture was stirred at room temperature for 1 hour. The reaction was again concentrated to dryness. The resulting residue was dissolved in DCM (0.5 mL), and HCl in ether (1 mL, 2N) was added. The resulting solid was collected by filtration to give (S)-1-(4-(5-bromo-1H-pyrazolo[3,4-b]pyridin-4-yl)piperazin-1-yl)-2-(4-chlorophenyl)-3-(isopropylamino)propan-1-one dihydrochloride (0.030 g, 53%). MS APCI (+) m/z 507.2 detected.

Example 12

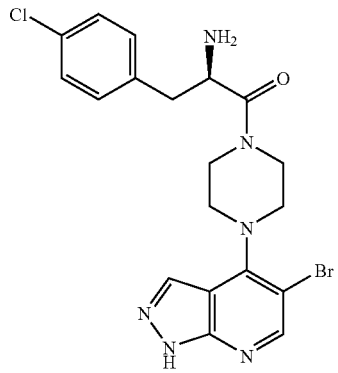 [SMILES: N[C@H](Cc1ccc(Cl)cc1)C(=O)N1CCN(c2c(Br)cnc3[nH]ncc23)CC1]

(R)-2-amino-1-(4-(5-bromo-1H-pyrazolo[3,4-b]pyridin-4-yl)piperazin-1-yl)-3-(4-chlorophenyl)propan-1-one DIEA (0.0687 mL, 0.394 mmol) was added to a solution of 5-bromo-4-(piperazin-1-yl)-1H-pyrazolo[3,4-b]pyridine dihydrochloride (0.050 g, 0.0986 mmol, see Example 11), (R)-2-(tert-butoxycarbonylamino)-3-(4-chlorophenyl)propanoic acid (0.0295 g, 0.099 mmol) and TBTU (0.0380 g, 0.118 mmol) in DCM (1 mL) and stirred at room temperature for 16 hours. The reaction was concentrated to dryness. The resulting residue was dissolved in THF/MeOH (2 mL, 1:1), and an aqueous LiOH solution (1 mL, 2M) was added. The solution was stirred for 30 minutes, and then ether (20 mL) was added. The organic layer was separated, washed with brine (10 mL), and dried over sodium sulfate. After removal of the solvent, the resulting residue was purified by column chromatography (hexane:ethyl acetate, 1:1) to give (R)-tert-butyl 1-(4-(5-bromo-1H-pyrazolo[3,4-b]pyridin-4-yl)piperazin-1-yl)-3-(4-chlorophenyl)-1-oxopropan-2-ylcarbamate as a solid. The solid was dissolved in DCM (1 mL), and TFA (0.4 mL) was added. The mixture was stirred at room temperature for 1 hour, and the reaction was concentrated to dryness. The resulting residue was dissolved in DCM (0.5 mL), and HCl in ether (1 mL, 2N) was added. The resulting solid was collected by filtration to give (R)-2-amino-1-(4-(5-bromo-1H-pyrazolo[3,4-b]pyridin-4-yl)piperazin-1-yl)-3-(4-chlorophenyl)propan-1-one dihydrochloride (0.015 g, 29%). MS APCI (+) m/z 463.1 detected.

Example 13

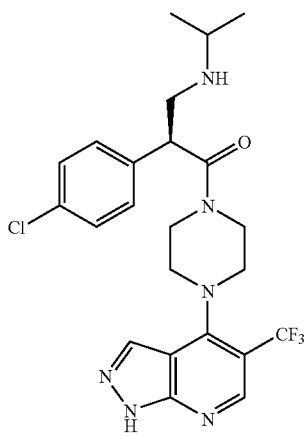 [SMILES: CC(C)NC[C@@H](C(=O)N1CCN(c2c(C(F)(F)F)cnc3[nH]ncc23)CC1)c1ccc(Cl)cc1]

(S)-2-(4-chlorophenyl)-3-(isopropylamino)-1-(4-(5-(trifluoromethyl)-1H-pyrazolo[3,4-b]pyridin-4-yl)piperazin-1-yl)propan-1-one Diiodine (0.547 g, 2.16 mmol) in ethanol (5 mL) was added dropwise over 5 minutes to a solution of 1-(4-methoxybenzyl)-1H-pyrazolo[3,4-b]pyridin-4-ol (0.50 g, 1.96 mmol, prepared similarly as that described in WO 2007/103308) in absolute ethanol (20 mL) at 0° C. The reaction was stirred at 0° C. for 3 hours, followed by addition of 5% sodium bicarbonate (20 mL). The mixture was concentrated to give a slurry. The pH was then adjusted with saturated $KHSO_4$ to a pH of 4. The resulting solid was collected by filtration and dried to give 5-iodo-1-(4-methoxybenzyl)-1H-pyrazolo[3,4-b]pyridin-4-ol (0.70 g, 94%). MS APCI (+) m/z 382.0 detected.

Sodium hydride (0.0881 g, 2.20 mmol) in DMF (5 mL) was added dropwise to 5-iodo-1-(4-methoxybenzyl)-1H-pyrazolo[3,4-b]pyridin-4-ol (0.70 g, 1.84 mmol) in DMF (5 mL). Then the reaction mixture was warmed to 40° C. and stirred for 30 minutes. After cooling to room temperature, 1,1,1-trifluoro-N-phenyl-N-(trifluoromethylsulfonyl)methanesulfonamide (0.787 g, 2.20 mmol) was added and stirred at room temperature for 1 hour. tert-Butyl piperazine-1-carboxylate (0.787 g, 4.22 mmol) was then added, and the mixture was stirred at 80° C. for 1 hour. Saturated $NH_4Cl$ (20 mL) was added, and the reaction was extracted with ethyl acetate and dried over sodium sulfate. After removal of the solvent, the resulting residue was purified by column chromatography (hexane:ethyl acetate, 5:1) to give tert-butyl 4-(5-iodo-1-(4-methoxybenzyl)-1H-pyrazolo[3,4-b]pyridin-4-yl)piperazine-1-carboxylate (0.94 g, 93%) as a solid. MS ESI (+) m/z 550.3 detected. $^1$H NMR (400 Hz, DMSO-d6) δ 8.64 (s, 1H), 8.31 (s, 1H), 7.20 (d, J=7.6 Hz, 2H), 6.82 (d, J=7.6 Hz, 2H), 5.52 (s, 2H), 3.69 (s, 3H), 3.56 (m, 4H), 3.46 (m, 4H), 1.44 (s, 9H).

A solution of tert-butyl 4-(5-iodo-1-(4-methoxybenzyl)-1H-pyrazolo[3,4-b]pyridin-4-yl)piperazine-1-carboxylate (0.150 g, 0.273 mmol), Cu(I)I (0.0520 g, 0.273 mmol) and methyl 2,2-difluoro-2-(fluorosulfonyl)acetate (0.122 mL, 0.956 mmol) in DMF (3 mL) were heated at 100° C. for 1 hour. The reaction was cooled to room temperature. Ethyl acetate (10 mL) was added, and the reaction mixture was filtered through a pad of celite. The filtrate was washed with water (5 mL), brine (5 mL), and dried over sodium sulfate. After removal of the solvent, the resulting residue was purified by column chromatography (hexane:ethyl acetate, 3:1) to give tert-butyl 4-(1-(4-methoxybenzyl)-5-(trifluoromethyl)-1H-pyrazolo[3,4-b]pyridin-4-yl)piperazine-1-carboxylate (0.114 g, 85%) as a solid. MS APCI (+) m/z 492.3 detected. $^1$H NMR (400 Hz, DMSO-d6) δ 8.59 (s, 1H), 8.41 (s, 1H), 7.22 (d, J=8.4 Hz, 2H), 6.82 (d, J=8.4 Hz, 2H), 5.55 (s, 2H), 3.70 (s, 3H), 3.52 (m, 8H), 1.43 (s, 9H).

TFA (0.5 mL) was added to a solution of tert-butyl 4-(1-(4-methoxybenzyl)-5-(trifluoromethyl)-1H-pyrazolo[3,4-b]pyridin-4-yl)piperazine-1-carboxylate (0.114 g, 0.232 mmol) in DCM (2 mL) and stirred at room temperature for 1 hour. The reaction was then concentrated to dryness. The resulting residue was dissolved in TFA (1.79 mL, 23.2 mmol) and heated at 65° C. for 2 hours. The reaction was again concentrated to dryness. The resulting residue was dissolved in DCM (0.5 mL), and HCl in ether (2 mL, 2N) was added. The resulting solid was collected by filtration to give 4-(piperazin-1-yl)-5-(trifluoromethyl)-1H-pyrazolo[3,4-b]pyridine dihydrochloride (0.075 g, 94%). MS APCI (+) m/z 272.0 detected.

DIEA (0.0607 mL, 0.349 mmol) was added to a solution of 4-(piperazin-1-yl)-5-(trifluoromethyl)-1H-pyrazolo[3,4-b]

pyridine dihydrochloride (0.030 g, 0.0872 mmol), 2-(1H-benzo[d][1,2,3]triazol-1-yl)-1,1,3,3-tetramethyluronium tetrafluoroborate (0.0336 g, 0.105 mmol) and (S)-3-(tert-butoxycarbonyl(isopropyl)amino)-2-(4-chlorophenyl) propanoic acid (0.0298 g, 0.0872 mmol, see Example B) in DCM (1 mL) and stirred at room temperature for 2 hours. The reaction was then concentrated to dryness. The resulting residue was dissolved in THF/MeOH (2 mL, 1:1) and an aqueous LiOH solution (1 mL, 2M) was added. The solution was stirred for 30 minutes, and then ether (20 mL) was added. The organic layer was separated, washed with brine (10 mL), and dried over sodium sulfate. After removal of the solvent, the resulting residue was purified by column chromatography (hexane:ethyl acetate, 1:1) to give (S)-tert-butyl 2-(4-chlorophenyl)-3-oxo-3-(4-(5-(trifluoromethyl)-1H-pyrazolo[3,4-b]pyridin-4-yl)piperazin-1-yl)propyl(isopropyl)carbamate as a solid. The solid was dissolved in DCM (1 mL), and TFA (0.4 mL) was added. The mixture was stirred at room temperature for 1 hour and then concentrated to dryness. The residue was dissolved in DCM (0.5 mL), and HCl in ether (1 mL, 2N) was added. The resulting solid was collected by filtration to give (S)-2-(4-chlorophenyl)-3-(isopropylamino)-1-(4-(5-(trifluoromethyl)-1H-pyrazolo[3,4-b]pyridin-4-yl) piperazin-1-yl)propan-1-one dihydrochloride (0.027 g, 54%). MS APCI (+) m/z 495.3 detected.

Example 14

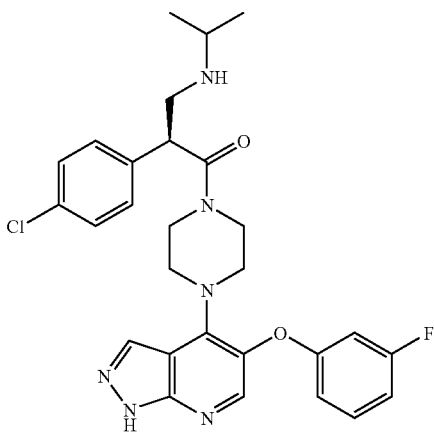 [SMILES: CC(C)NC[C@@H](C(=O)N1CCN(c2c(Oc3cccc(F)c3)cnc3[nH]ncc23)CC1)c1ccc(Cl)cc1]

(S)-2-(4-chlorophenyl)-1-(4-(5-(3-fluorophenoxy)-1H-pyrazolo[3,4-b]pyridin-4-yl)piperazin-1-yl)-3-(isopropylamino)propan-1-one A solution of tert-butyl 4-(5-iodo-1-(4-methoxybenzyl)-1H-pyrazolo[3,4-b]pyridin-4-yl)piperazine-1-carboxylate (0.100 g, 0.182 mmol, see Example 13), Cu(I)Cl (0.00901 g, 0.0910 mmol), 2,2,6,6-tetramethylheptane-3,5-dione (0.00950 mL, 0.0455 mmol), Cs$_2$CO$_3$ (0.119 g, 0.364 mmol) and 3-fluorophenol (0.165 mL, 1.82 mmol) in NMP (2 mL) was stirred at 106° C. for 20 hours. The reaction was then cooled to room temperature, and H$_2$O (5 mL) was added. The reaction mixture was then extracted with ethyl acetate (15 mL), washed with brine, and dried over sodium sulfate. After removal of the solvent, the resulting residue was purified by column chromatography (hexane:ethyl acetate, 2.5:1) to give tert-butyl 4-(5-(3-fluorophenoxy)-1-(4-methoxybenzyl)-1H-pyrazolo[3,4-b]pyridin-4-yl)piperazine-1-carboxylate (0.020 g, 21%) as a solid. MS APCI (+) m/z 534.4 detected.

TFA (0.5 mL) was added to tert-butyl 4-(5-(3-fluorophenoxy)-1-(4-methoxybenzyl)-1H-pyrazolo[3,4-b]pyridin-4-yl)piperazine-1-carboxylate (0.020 g, 0.0375 mmol) in DCM (2 mL) and stirred at room temperature for 1 hour. The reaction was concentrated to dryness. The resulting residue was dissolved in TFA (1 mL) and heated at 65° C. for 2 hours. The reaction was concentrated to dryness. The resulting residue was dissolved in DCM (0.5 mL), and HCl in ether (1 mL, 2N) was added. The reaction was concentrated to dryness to give 5-(3-fluorophenoxy)-4-(piperazin-1-yl)-1H-pyrazolo[3,4-b]pyridine dihydrochloride (0.014 g, 99%) as a solid. MS APCI (+) m/z 314.1 detected.

DIEA (0.0271 mL, 0.155 mmol) was added to 5-(3-fluorophenoxy)-4-(piperazin-1-yl)-1H-pyrazolo[3,4-b]pyridine dihydrochloride (0.015 g, 0.0388 mmol), 2-(1H-benzo[d][1,2,3]triazol-1-yl)-1,1,3,3-tetramethyluronium tetrafluoroborate (0.0150 g, 0.0466 mmol) and (S)-3-(tert-butoxycarbonyl (isopropyl)amino)-2-(4-chlorophenyl)propanoic acid (0.0133 g, 0.0388 mmol, see Example B) in DCM (1 mL) and stirred at room temperature for 30 minutes. The reaction was then concentrated to dryness. The resulting residue was dissolved in THF/MeOH (2 mL, 1:1), and an aqueous LiOH solution (1 mL, 2M) was added. The reaction was stirred for 30 minutes, and then ether (20 mL) was added. The organic layer was separated, washed with brine (10 mL), and dried over sodium sulfate. After removal of the solvent, the resulting residue was purified by column chromatography (hexane:ethyl acetate, 1:1) to give (S)-tert-butyl 2-(4-chlorophenyl)-3-(4-(5-(3-fluorophenoxy)-1H-pyrazolo[3,4-b]pyridin-4-yl) piperazin-1-yl)-3-oxopropyl(isopropyl)carbamate as a solid. The solid was dissolved in DCM (1 mL), and TFA (0.4 mL) was added. The reaction was stirred at room temperature for 30 minutes and concentrated to dryness. The residue was dissolved in DCM (0.5 mL), and HCl in ether (1 mL, 2N) was added. The resulting solid was collected by filtration to give (S)-2-(4-chlorophenyl)-1-(4-(5-(3-fluorophenoxy)-1H-pyrazolo[3,4-b]pyridin-4-yl)piperazin-1-yl)-3-(isopropylamino)propan-1-one (0.006 g, 25%). MS APCI (+) m/z 537.3 detected.

Example 15

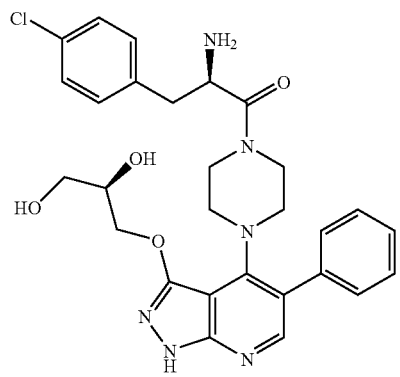 [SMILES: N[C@H](Cc1ccc(Cl)cc1)C(=O)N1CCN(c2c(-c3ccccc3)cnc3[nH]nc(OC[C@H](O)CO)c23)CC1]

(R)-2-amino-3-(4-chlorophenyl)-1-(4-(3-((R)-2,3-dihydroxypropoxy)-5-phenyl-1H-pyrazolo[3,4-b]pyridin-4-yl)piperazin-1-yl)propan-1-one tert-Butyl 4-(3-iodo-1-(4-methoxybenzyl)-5-phenyl-1H-pyrazolo[3,4-b]pyridin-4-yl)piperazine-1-carboxylate (0.15 g, 0.24 mmol, see Example 9), Cu(I)I (0.046 g, 0.24 mmol), 1,10-phenanthroline (0.043 g, 0.24 mmol), (R)-(2,2-dimethyl-1,3-dioxolan-4-yl)methanol (0.95 g, 7.2 mmol) and KF on Al₂O₃ (40%; 0.24 g, 1.68 mmol) in toluene (4 mL) was stirred at 110° C. for 60 hours. Ethyl acetate (10 mL) was then added, and the reaction mixture was filtered through a pad of celite. The reaction was then concentrated to dryness, and the residue was purified by column chromatography (hexane: ethyl acetate=1:1) to give (R)-tert-butyl 4-(3-((2,2-dimethyl-1,3-dioxolan-4-yl)methoxy)-5-phenyl-1H-pyrazolo[3,4-b]pyridin-4-yl)piperazine-1-carboxylate (0.14 g, 93%) as a solid. MS APCI (+) m/z 630.2 detected.

TFA (1 mL) was added to a solution of (R)-tert-butyl 4-(3-((2,2-dimethyl-1,3-dioxolan-4-yl)methoxy)-1-(4-methoxybenzyl)-5-phenyl-1H-pyrazolo[3,4-b]pyridin-4-yl)piperazine-1-carboxylate (0.14 g, 0.22 mmol) in DCM (1 mL), and the resulting solution was stirred at room temperature for 4 hours. The reaction was then concentrated to dryness and dried under vacuum for 1 hour. TFA (2 mL) was next added, and the mixture was stirred at 100° C. in a sealed tube for 18 hours. The reaction was then concentrated to dryness, and the resulting residue was dissolved in DCM (0.5 mL). HCl in ether (2 mL, 2N) and ether (3 mL) were then added, and the resulting solid was collected by filtration to give (S)-3-(5-phenyl-4-(piperazin-1-yl)-1H-pyrazolo[3,4-b]pyridin-3-yloxy)propane-1,2-diol dihydrochloride (0.105, 96%) as a solid. MS APCI (+) m/z 370.2 detected.

DIEA (0.055 mL, 0.32 mmol) was added to a solution of (S)-3-(5-phenyl-4-(piperazin-1-yl)-1H-pyrazolo[3,4-b]pyridin-3-yloxy)propane-1,2-diol dihydrochloride (0.050 g, 0.079 mmol), (R)-2-(tert-butoxycarbonylamino)-3-(4-chlorophenyl)propanoic acid (0.024 g, 0.079 mmol) and TBTU (0.031 g, 0.095 mmol) in DCM (1 mL) and stirred at room temperature for 1 hour. The reaction was then concentrated to dryness, and the residue was dissolved in THF/MeOH (2 mL, 1:1), and an aqueous LiOH solution (1 mL, 2 M) was added. The reaction was then stirred for an additional 10 minutes. Ethyl acetate (20 mL) was added, and the organic layer was separated, washed with brine (10 mL), and dried over sodium sulfate. After removal of the solvent, the resulting residue was purified by column chromatography (ethyl acetate:MeOH, 20:1) to give tert-butyl(R)-3-(4-chlorophenyl)-1-(4-(3-((S)-2,3-dihydroxypropoxy)-5-phenyl-1H-pyrazolo[3,4-b]pyridin-4-yl)piperazin-1-yl)-1-oxopropan-2-ylcarbamate as a solid. The solid was then dissolved in DCM (1 mL), and TFA (0.4 mL) was added. The mixture was stirred at room temperature for 1 hour and concentrated to dryness. The resulting residue was dissolved in DCM (0.5 mL), and HCl in ether (1 mL, 2 N) was added. The resulting solid was collected by filtration to give (R)-2-amino-3-(4-chlorophenyl)-1-(4-(3-((S)-2,3-dihydroxypropoxy)-5-phenyl-1H-pyrazolo[3,4-b]pyridin-4-yl)piperazin-1-yl)propan-1-one dihydrochloride (0.018 g, 36%). MS APCI (+) m/z 551.2 detected.

Example 16

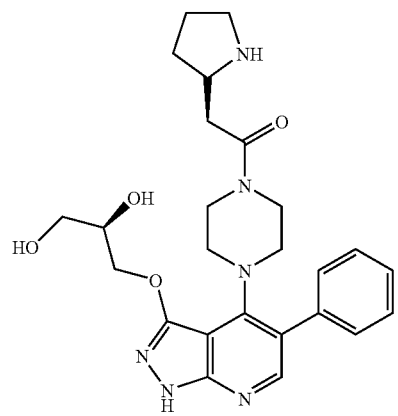

1-(4-(3-((R)-2,3-dihydroxypropoxy)-5-phenyl-1H-pyrazolo[3,4-b]pyridin-4-yl)piperazin-1-yl)-2-((S)-pyrrolidin-2-yl)ethanone DIEA (0.055 mL, 0.32 mmol) was added to a solution of (S)-3-(5-phenyl-4-(piperazin-1-yl)-1H-pyrazolo[3,4-b]pyridin-3-yloxy)propane-1,2-diol dihydrochloride (0.050 g, 0.079 mmol, see Example 15), (S)-2-(1-(tert-butoxycarbonyl)pyrrolidin-2-yl)acetic acid (0.018 g, 0.079 mmol) and TBTU (0.031 g, 0.095 mmol) in DCM (1 mL) and stirred at room temperature for 1 hour. The reaction was then concentrated to dryness, and the residue was dissolved in THF/MeOH (2 mL, 1:1), and an aqueous LiOH solution (1 mL, 2 M) was added. The mixture was stirred for 10 minutes. Ethyl acetate (20 mL) was then added, and the organic layer was separated, washed with brine (10 mL), and dried over sodium sulfate. After removal of the solvent, the residue was purified by column chromatography (ethyl acetate:MeOH, 20:1) to give tert-butyl(R)-3-(4-chlorophenyl)-1-(4-(3-((S)-2,3-dihydroxypropoxy)-5-phenyl-1H-pyrazolo[3,4-b]pyridin-4-yl)piperazin-1-yl)-1-oxopropan-2-ylcarbamate as a solid. The solid was then dissolved in DCM (1 mL), and TFA (0.4 mL) was added. The mixture was stirred at room temperature for 1 hour and concentrated to dryness. The resulting residue was dissolved in DCM (0.5 mL), and HCl in ether (1 mL, 2 N)) was added. The resulting solid was collected by filtration to give (1-(4-(3-((S)-2,3-dihydroxypropoxy)-5-phenyl-1H-pyrazolo[3,4-b]pyridin-4-yl)piperazin-1-yl)-2-((S)-pyrrolidin-2-yl)ethanone dihydrochloride (0.019 g, 43%). MS APCI (+) m/z 481.2 detected.

Example 17

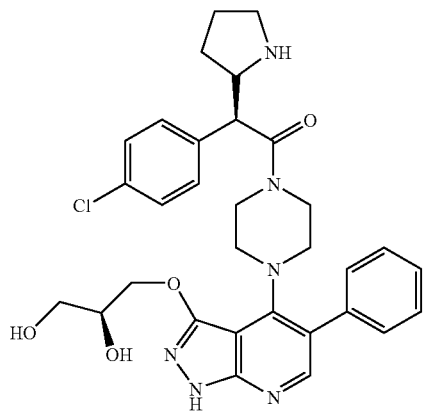 [SMILES: O=C([C@@H](c1ccc(Cl)cc1)C1CCCN1)N1CCN(c2c(-c3ccccc3)cnc3[nH]nc(OC[C@@H](O)CO)c23)CC1]

(S)-2-(4-chlorophenyl)-1-(4-(3-((S)-2,3-dihydroxypropoxy)-5-phenyl-1H-pyrazolo[3,4-b]pyridin-4-yl)piperazin-1-yl)-2-((S)-pyrrolidin-2-yl)ethanone DIEA (0.055 mL, 0.32 mmol) was added to a solution of (S)-3-(5-phenyl-4-(piperazin-1-yl)-1H-pyrazolo[3,4-b]pyridin-3-yloxy)propane-1,2-diol dihydrochloride (0.050 g, 0.079 mmol, see Example 15), (S)-2-((S)-1-(tert-butoxycarbonyl)pyrrolidin-2-yl)-2-(4-chlorophenyl)acetic acid (0.027 g, 0.079 mmol, see Example C) and TBTU (0.031 g, 0.095 mmol) in DCM (1 mL) and stirred at room temperature for 1 hour. The reaction was then concentrated to dryness. The resulting residue was dissolved in THF/MeOH (2 mL, 1:1), and an aqueous LiOH solution (1 mL, 2 M) was added. The mixture was stirred for 10 minutes. Ethyl acetate (20 mL) was then added, and the organic layer was separated, washed with brine (10 mL), and dried over sodium sulfate. After removal of the solvent, the residue was purified by column chromatography (ethyl acetate:MeOH, 20:1) to give tert-butyl(R)-3-(4-chlorophenyl)-1-(4-(3-((S)-2,3-dihydroxypropoxy)-5-phenyl-1H-pyrazolo[3,4-b]pyridin-4-yl)piperazin-1-yl)-1-oxopropan-2-ylcarbamate as a solid. The solid was then dissolved in DCM (1 mL), and TFA (0.4 mL) was added. The mixture was stirred at room temperature for 1 hour and concentrated to dryness. The resulting residue was dissolved in DCM (0.5 mL), and HCl in ether (1 mL, 2 N) was added. The solvent was then removed. The residue was dissolved in MeOH (3 mL), and an aqueous LiOH solution (3 mL, 2 N) was added. The mixture was stirred for 5 minutes, and then extracted with DCM (20 mL) and dried over sodium sulfate. Removal of the solvent provided (S)-2-(4-chlorophenyl)-1-(4-(3-((S)-2,3-dihydroxypropoxy)-5-phenyl-1H-pyrazolo[3,4-b]pyridin-4-yl)piperazin-1-yl)-2-((S)-pyrrolidin-2-yl)ethanone (0.011 g, 24% yield) as a solid. MS APCI (+) m/z 591.2 detected.

Example 18

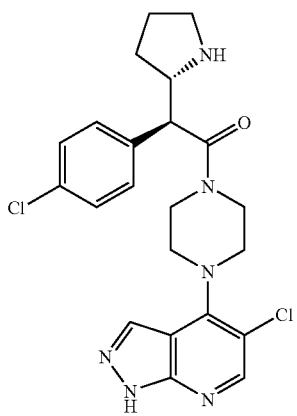 [SMILES: O=C([C@@H](c1ccc(Cl)cc1)[C@@H]1CCCN1)N1CCN(c2c(Cl)cnc3[nH]ncc23)CC1]

(S)-1-(4-(5-chloro-1H-pyrazolo[3,4-b]pyridin-4-yl)piperazin-1-yl)-2-(4-chlorophenyl)-2-((S)-pyrrolidin-2-yl)ethanone NCS (1.57 g, 11.8 mmol) was added in one portion to a solution of 1-(4-methoxybenzyl)-1H-pyrazolo[3,4-b]pyridin-4-ol (3.00 g, 11.8 mmol) in DMF (30 mL) at room temperature. The mixture was stirred at 60° C. for 1 hour and then cooled to room temperature. After 18 hours, an additional lot of NCS (0.5 eq.) was added to the reaction mixture and stirred at room temperature for an additional 48 hours. The reaction mixture was poured into water (150 mL) and extracted with EtOAc (3×50 mL). The combined organic layers were washed once with water (50 mL), dried (MgSO$_4$), filtered, and concentrated in vacuo. The crude material was purified by flash chromatography on silica gel (Biotage Flash 40M+) eluting with 2% MeOH/CH$_2$Cl$_2$ to provide 5-chloro-1-(4-methoxybenzyl)-1H-pyrazolo[3,4-b]pyridin-4-ol (466 mg, 1.61 mmol, 13.7% yield). LCMS (APCI+) m/z 290 (M+H)+.

A solution of 5-chloro-1-(4-methoxybenzyl)-1H-pyrazolo[3,4-b]pyridin-4-ol (450 mg, 1.55 mmol) in DMF (5 mL) was added dropwise to a suspension of sodium hydride (60% dispersion in mineral oil, 74.5 mg, 1.86 mmol) in DMF (5 mL) at room temperature. The mixture was stirred at 40° C. for 30 minutes. The resulting solution was cooled to room temperature and treated with 1,1,1-trifluoro-N-phenyl-N-(trifluoromethylsulfonyl)methanesulfonamide (666 mg, 1.86 mmol). The reaction mixture was stirred at room temperature for 1 hour. Next, the solid tert-butyl piperazine-1-carboxylate (636 mg, 3.42 mmol) was added in 2 portions, and the mixture was stirred at 80° C. for 1.5 hours. The mixture was then allowed to cool to room temperature for 18 hours. Saturated NH$_4$Cl solution (30 mL) and water (15 mL) were added, and the mixture was extracted with EtOAc (100 mL). The organic layer was washed with half saturated brine (2×20 mL), dried (MgSO$_4$), filtered, and concentrated in vacuo. The resulting residue was purified by flash chromatography on silica gel (Biotage Flash 40 S+) eluting with 15-20%) EtOAc/hexane (step gradient) to provide tert-butyl 4-(5-chloro-1-(4-methoxybenzyl)-1H-pyrazolo[3,4-b]pyridin-4-yl)piperazine-1-carboxylate (433 mg, 0.946 mmol, 60.9% yield) as a solid after drying under high vacuum for 18 hours. LCMS (APCI+) m/z 458.1, 460 (M+H)+.

25% TFA/CH$_2$Cl$_2$ (10 mL) was added to tert-butyl 4-(5-chloro-1-(4-methoxybenzyl)-1H-pyrazolo[3,4-b]pyridin-4-yl)piperazine-1-carboxylate (430 mg, 0.939 mmol), and the solution was stirred at room temperature. After 30 minutes, the solvent was removed under reduced pressure. The resulting residue was evaporated from toluene (3×10 mL) and dried under high vacuum for 18 hours to provide 5-chloro-1-(4-methoxybenzyl)-4-(piperazin-1-yl)-1H-pyrazolo[3,4-b]pyridine 2,2,2-trifluoroacetate. Neat TFA (10 mL) was added to this material, and the mixture was stirred at reflux for 90 minutes. TFA was removed under reduced pressure, and the residue was evaporated from CH$_2$Cl$_2$ (2×10 mL). The residue was redissolved in CH$_2$Cl$_2$, and 2M HCl in ether (6 mL) was added. The resulting suspension was concentrated in vacuo. The residue obtained was treated with 2M HCl in diethyl ether once more (5 mL) and subjected to sonication for 2 minutes. Then the solvent was removed in vacuo, and the resulting residue was triturated with Et$_2$O. The solid formed was filtered, washed with ether (2×5 mL) and dried under high vacuum to provide 5-chloro-4-(piperazin-1-yl)-1H-pyrazolo[3,4-b]pyridine dihydrochloride (280 mg, 0.901 mmol, 62.0% yield) as a solid. LCMS (APCI+) m/z 238.0 (M+H)+.

A solution of 5-chloro-4-(piperazin-1-yl)-1H-pyrazolo[3,4-b]pyridine dihydrochloride (75 mg, 0.205 mmol), 2-(3H-[1,2,3]triazolo[4,5-b]pyridin-3-yl)-1,1,3,3-tetramethylisouronium hexafluorophosphate (V) ("HATU"; 78.0 mg, 0.205 mmol), N-ethyl-N-isopropylpropan-2-amine (143 μL, 0.821 mmol), and (S)-2-((S)-1-(tert-butoxycarbonyl)pyrrolidin-2-yl)-2-(4-chlorophenyl)acetic acid (83.7 mg, 0.246 mmol, see Example C) in CH$_2$Cl$_2$ (5 mL) was stirred at room temperature for 1 hour. The solvent was removed, and the resulting residue was redissolved in EtOAc (20 mL) and washed with water. The organic phase was dried over MgSO$_4$, filtered, and concentrated in vacuo. The crude obtained was purified by C-18 reverse phase column chromatography (Biotage C-18 12M+) using 10-90% CHsCN/water gradient on Biotage SP4 unit. The fractions containing the product were pooled, and the solvents were removed and evaporated from CH$_3$CN (3×10 mL). The residue was transferred to a 25 mL round bottom flask using EtOAc (about 5 to about 10 mL). The residue was concentrated in vacuo and dried under high vacuum for 2 hours to provide (S)-tert-butyl 2-((S)-2-(4-(5-chloro-1H-pyrazolo[3,4-b]pyridin-4-yl)piperazin-1-yl)-1-(4-chlorophenyl)-2-oxoethyl)pyrrolidine-1-carboxylate (95 mg, 0.170 mmol, 82.7% yield) as a solid. LCMS (APCI+) m/z 459.1 [(M-Boc)+H]+.

4N HCl in dioxane (2 mL) was added to a solution of (S)-tert-butyl 2-((S)-2-(4-(5-chloro-1H-pyrazolo[3,4-b]pyridin-4-yl)piperazin-1-yl)-1-(4-chlorophenyl)-2-oxoethyl)pyrrolidine-1-carboxylate (90 mg, 0.16 mmol) in CH$_2$Cl$_2$ (1 ml). The mixture was stirred at room temperature for 30 minutes. After 30 minutes, the solvent was removed in vacuo, and the resulting residue was triturated with ether. The solid material was filtered, washed with additional ether (2×2 mL) and dried to provide (S)-1-(4-(5-chloro-1H-pyrazolo[3,4-b]pyridin-4-yl)piperazin-1-yl)-2-(4-chlorophenyl)-2-((S)-pyrrolidin-2-yl)ethanone dihydrochloride (71 mg, 0.13 mmol, 83% yield) as a cream solid. LCMS (APCI+) m/z 459.1, 461.1 [(M+H)]$^+$. NMR (400 Hz, DMSO-d$_6$) δ 9.61 (br s, 1H), 9.08 (br s, 1H), 8.30 (s, 1H), 8.19 (s, 1H), 7.49 (d, 2H), 7.44 (d, 2H), 4.53 (d, 1H), 4.03-3.96 (m, 1H), 3.79-3.70 (m, 3H), 3.69-3.57 (m, 3H), 3.51-3.45 (m, 1H), 3.21-3.14 (m, 2H), 3.09-3.00 (m, 1H), 1.97-1.89 (m, 1H), 1.78-1.71 (m, 1H), 1.63-1.52 (m, 2H).

Example 19

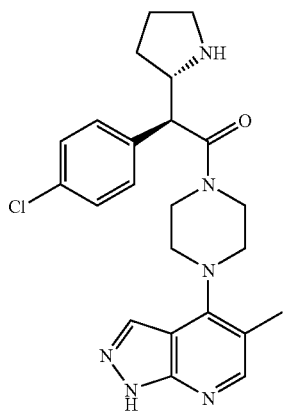 [SMILES: Cc1cnc2[nH]ncc2c1N1CCN(C(=O)[C@@H](c2ccc(Cl)cc2)[C@@H]2CCCN2)CC1]

(S)-2-(4-chlorophenyl)-1-(4-(5-methyl-1H-pyrazolo [3,4-b]pyridin-4-yl)piperazin-1-yl)-2-((S)-pyrrolidin-2-yl)ethanone Methylzinc (II) chloride (2M solution in THF, 1244 μL, 2.488 mmol) was added to a solution of tert-butyl 4-(5-bromo-1-(4-methoxybenzyl)-1H-pyrazolo[3,4-b]pyridin-4-yl)piperazine-1-carboxylate (500 mg, 0.995 mmol) and Pd(PPh$_3$)$_4$ (86.25 mg, 0.07464 mmol) in THF (5 mL) under a nitrogen atmosphere. The reaction mixture was stirred at 75° C. for 1.5 hours and allowed to cool to room temperature. The mixture was poured into a saturated aqueous NH$_4$Cl solution (50 mL) and extracted with EtOAc (3×50 mL). The combined organic layers were dried (MgSO$_4$), filtered and concentrated in vacuo. The resulting residue was purified by flash chromatography on silica gel (Biotage Flash 40S+) eluting with 2% MeOH/CH$_2$Cl$_2$ to provide tert-butyl 4-(1-(4-methoxybenzyl)-5-methyl-1H-pyrazolo[3,4-b]pyridin-4-yl)piperazine-1-carboxylate (470 mg, 0.806 mmol, 81.0% yield) as a solid. LCMS (APCI+) m/z 438.2 (M+H)+.

tert-Butyl 4-(1-(4-methoxybenzyl)-5-methyl-1H-pyrazolo[3,4-b]pyridin-4-yl)piperazine-1-carboxylate (465 mg, 1.06 mmol) in 25% TFA/CH$_2$Cl$_2$ (25 mL) was stirred at room temperature for 2 hours. The solvent was removed, and the gum obtained was evaporated from toluene (3×20 mL; water bath 60° C.). Neat TFA was added to the residue and stirred at reflux for 3 hours. Next, TFA was removed under reduced pressure, and the resulting residue was evaporated form CH$_2$Cl$_2$ (2×10 mL). The residue was resuspended in CH$_2$Cl$_2$ (2 mL), and 2M HCl in diethyl ether (5 mL) was added. The resulting suspension was concentrated in vacuo, and the residue was crystallized from boiling EtOH to provide 5-methyl-4-(piperazin-1-yl)-1H-pyrazolo[3,4-b]pyridine dihydrochloride (175 mg, 0.603 mmol, 56.7% yield) as a powder after drying under high vacuum for 4 hours. LCMS (APCI+) m/z 218.1 (M+H)+.

A solution of 5-methyl-4-(piperazin-1-yl)-1H-pyrazolo[3,4-b]pyridine dihydrochloride (75 mg, 0.194 mmol), diisopropylethylamine (135 μL, 0.775 mmol), HATU (73.7 mg, 0.194 mmol) and (S)-2-((S)-1-(tert-butoxycarbonyl)pyrrolidin-2-yl)-2-(4-chlorophenyl)acetic acid (79.0 mg, 0.233 mmol, see Example C) in DMF (5 mL) was stirred at room temperature for 18 hours. The reaction mixture was concentrated in vacuo. The resulting residue was redissolved in THF (5 mL) and treated with an aqueous solution of LiOH (2 mL, 0.5M) for 30 minutes. Next, the solvent was removed, and the resulting residue was suspended in EtOAc (50 mL) and washed with water (2×10 mL). The dried (MgSO$_4$) organic phase was concentrated in vacuo, and the resulting residue was purified by reverse phase chromatography (Biotage, C-18 12M+) on Biotage SP4 unit using a gradient of 5-80% CH3CN/water to provide (S)-tert-butyl 2-((S)-1-(4-chlorophenyl)-2-(4-(5-methyl-1H-pyrazolo[3,4-b]pyridin-4-yl)piperazin-1-yl)-2-oxoethyl)pyrrolidine-1-carboxylate (70 mg, 0.130 mmol, 67.0% yield) as a solid after drying under high vacuum. LCMS (APCI+) m/z 539.2, 541.2 (M+H)+.

4N HCl in dioxane (5 mL) was added to (S)-tert-butyl 2-((S)-1-(4-chlorophenyl)-2-(4-(5-methyl-1H-pyrazolo[3,4-b]pyridin-4-yl)piperazin-1-yl)-2-oxoethyl)pyrrolidine-1-carboxylate (68 mg, 0.13 mmol), and the mixture was stirred at room temperature. After 30 minutes, the solvent was removed under reduced pressure, and the resulting residue was triturated with ether. The solid material was filtered, washed with additional ether (2×2 mL) and dried under high vacuum for 24 hours to provide (S)-2-(4-chlorophenyl)-1-(4-(5-methyl-1H-pyrazolo[3,4-b]pyridin-4-yl)piperazin-1-yl)-2-((S)-pyrrolidin-2-yl)ethanone dihydrochloride (62 mg, 0.12 mmol, 96% yield) as a solid. LCMS (APCI+) m/z 439.1 (M+H)$^+$. NMR (400 Hz, DMSO-d$_6$) δ 9.98 (brs, 1H), 9.06 (s, 1H), 8.23 (s, 1H), 7.49 (d, 2H), 7.43 (d, 2H), 4.56 (d, 1H), 4.03-3.96 (m, 2H), 3.93-3.87 (m, 3H), 3.71-3.65 (m, 1H), 3.64-3.57 (m, 2H), 3.50-3.46 (m, 1H), 3.19-3.13 (m, 2H), 2.31 (s, 3H), 1.97-1.89 (m, 1H), 1.78-1.70 (m, 1H), 1.63-1.52 (m, 2H).

Example 20

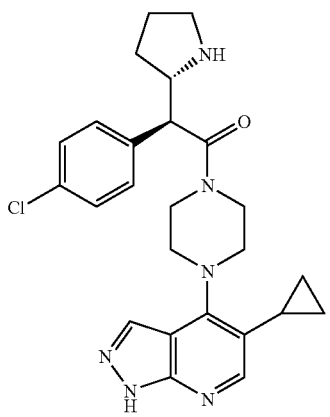 [SMILES: O=C([C@@H](c1ccc(Cl)cc1)[C@@H]1CCCN1)N1CCN(c2c(C3CC3)cnc3[nH]ncc23)CC1]

(S)-2-(4-chlorophenyl)-1-(4-(5-cyclopropyl-1H-pyrazolo[3,4-b]pyridin-4-yl)piperazin-1-yl)-2-((S)-pyrrolidin-2-yl)ethanone Cyclopropylzinc (II) bromide (2.5 mL, 2.49 mmol) was added to a solution of tert-butyl 4-(5-bromo-1-(4-methoxybenzyl)-1H-pyrazolo[3,4-b]pyridin-4-yl)piperazine-1-carboxylate (500 mg, 0.995 mmol, see Example 1) and Pd(PPh$_3$)$_4$ (86 mg, 0.075 mmol) in THF (5 mL) under nitrogen, and the reaction mixture was heated to 75° C. (oil bath) for 18 hours under a nitrogen atmosphere. Then the reaction mixture was allowed to cool to room temperature and poured into a saturated aqueous NH$_4$Cl (50 mL) solution and extracted with EtOAc (3×50 mL). The crude product was purified by C-18 reverse phase flash chromatography (Biotage 25M+) using a gradient of 15-90% CH$_3$CN/water on Biotage SP4 unit to provide tert-butyl 4-(5-cyclopropyl-1-(4-methoxybenzyl)-1H-pyrazolo[3,4-b]pyridin-4-yl)piperazine-1-carboxylate (275 mg, 0.59 mmol, 59.6% yield) as a solid. LCMS (APCI+) m/z 464.2 (M+H).

(S)-2-(4-Chlorophenyl)-1-(4-(5-cyclopropyl-1H-pyrazolo[3,4-b]pyridin-4-yl)piperazin-1-yl)-2-((S)-pyrrolidin-2-yl)ethanone dihydrochloride was prepared as described in Example 19 by using tert-butyl 4-(5-cyclopropyl-1-(4-methoxybenzyl)-1H-pyrazolo[3,4-b]pyridin-4-yl)piperazine-1-carboxylate to provide a solid (51 mg, 60% yield). LCMS (APCI+) m/z 465.1 (M+H)+. NMR (400 Hz, DMSO-d6) δ 9.99 (br s, 0.6H), 9.06 (br s, 1H), 8.13 (s, 1H), 7.50 (d, 2H), 7.45 (d, 2H0, 4.56 (d, 1H), 4.03-3.89 (m, 6H), 3.67-3.61 (m, 2H), 3.44-3.38 (m, 1H), 3.18-3.14 (m 2H), 2.06-1.91 (m, 2H), 1.78-1.71 (m, 1H), 1.61-1.53 (m, 2H), 0.95 (d, 2H), 0.67 (d, 2H).

Examples 21-38 shown in Table 1 can also be made according to the above described methods.

TABLE 1

| Ex # | Structure | Name | NMR/LCMS |
|---|---|---|---|
| 21 | 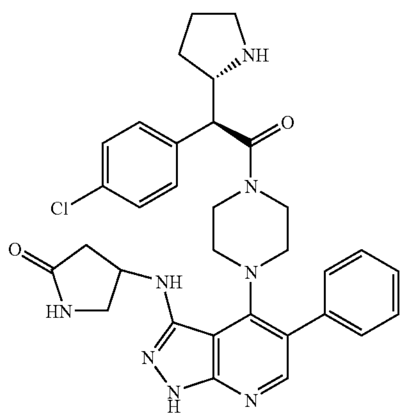 [SMILES: O=C1CC(Nc2n[nH]c3ncc(-c4ccccc4)c(N4CCN(C(=O)[C@@H](c5ccc(Cl)cc5)[C@@H]5CCCN5)CC4)c23)CN1] | 4-(4-(4-((S)-2-(4-chlorophenyl)-2-((S)-pyrrolidin-2-yl)acetyl)piperazin-1-yl)-5-phenyl-1H-pyrazolo[3,4-b]pyridin-3-ylamino)pyrrolidin-2-one hydrochloride | LCMS (APCI+) m/z 599 (M + H)+ |
| 22 | 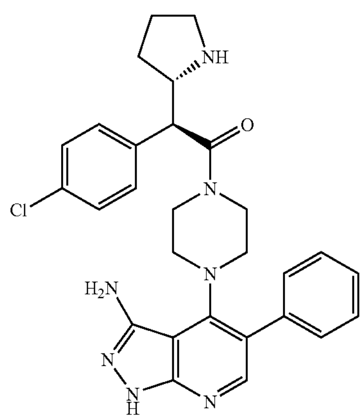 [SMILES: Nc1n[nH]c2ncc(-c3ccccc3)c(N3CCN(C(=O)[C@@H](c4ccc(Cl)cc4)[C@@H]4CCCN4)CC3)c12] | (S)-1-(4-(3-amino-5-phenyl-1H-pyrazolo[3,4-b]pyridin-4-yl)piperazin-1-yl)-2-(4-chlorophenyl)-2-((S)-pyrrolidin-2-yl)ethanone | LCMS (APCI+) m/z 516 (M + H)+ |

TABLE 1-continued

| Ex # | Structure | Name | NMR/LCMS |
|---|---|---|---|
| 23 | 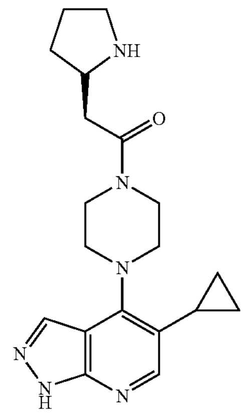 | (S)-1-(4-(5-cyclopropyl-1H-pyrazolo[3,4-b]pyridin-4-yl)piperazin-1-yl)-2-(pyrrolidin-2-yl)ethanone hydrochloride | $^1$H NMR (400 MHz, d$_6$-DMSO) δ 9.27 (m, 2H), 8.17 (s, 1H), 4.13-3.94 (m, 4H), 3.81-3.72 (m, 5H), 3.17-3.10 (m, 2H), 3.00-2.67 (m, 2H), 2.17-2.10 (m, 1H), 2.06-2.01 (m, 1H), 1.98-1.89 (m, 1H), 1.88-1.81 (m, 1H), 1.63-1.57 (m, 1H), 1.03-0.98 (m, 2H), 0.76-0.72 (m, 2H); LCMS (APCI+) m/z 355.1 (M + H)+ |
| 24 | 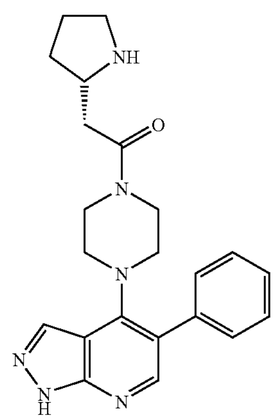 | (S)-1-(4-(5-phenyl-1H-pyrazolo[3,4-b]pyridin-4-yl)piperazin-1-yl)-2-(pyrrolidin-2-yl)ethanone hydrochloride | $^1$H NMR (400 MHz, D$_2$O) δ 8.48 (s, 1H), 7.95 (s, 1H), 7.37 (m, 5H), 3.73 (m, 1H), 3.41-3.60 (m, 8H), 3.12 (m, 2H), 2.83 (m, 1H), 2.64 (m, 1H), 2.05 (m, 1H), 1.88 (m, 1H), 1.81 (m, 1H), 1.55 (m, 1H); LCMS (APCI+) m/z 391 (M + H)+ |
| 25 | 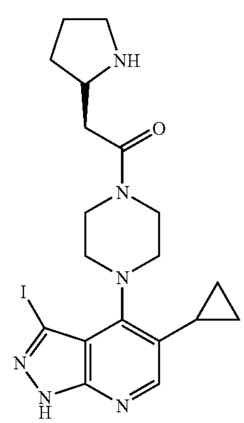 | (S)-1-(4-(5-cyclopropyl-3-iodo-1H-pyrazolo[3,4-b]pyridin-4-yl)piperazin-1-yl)-2-(pyrrolidin-2-yl)ethanone hydrochloride | $^1$H NMR (400 MHz, d$_6$-DMSO) δ 9.15-8.97 (m, 2H), 8.27 (s, 1H), 3.89-3.85 (m, 2H), 3.81-3.76 (m, 2H), 3.71-3.66 (m, 2H), 3.50-3.46 (m, 2H), 3.43-3.39 (m, 2H), 3.17-3.10 (m, 2H), 2.99-2.96 (m, 2H), 2.16-2.04 (m, 1H), 1.97-1.89 (m, 1H), 1.87-1.80 (m, 1H), 1.66-1.61 (m, 1H), 1.01-0.97 (m, 2H), 0.79-0.75 (m, 2H); LCMS (APCI+) m/z 481.1 (M + H)+ |

| Ex # | Structure | Name | NMR/LCMS |
|---|---|---|---|
| 26 | 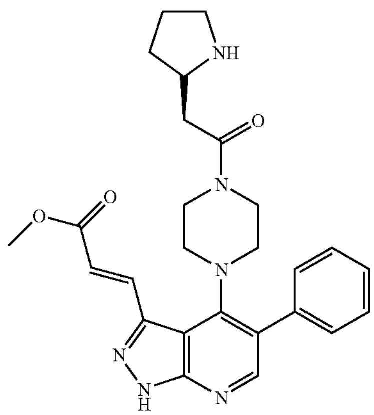 | (S,E)-methyl 3-(5-phenyl-4-(4-(2-(pyrrolidin-2-yl)acetyl)piperazin-1-yl)-1H-pyrazolo[3,4-b]pyridin-3-yl)acrylate hydrochloride | $^1$H NMR (400 MHz, d$_6$-DMSO) δ 8.27 (d, 1H), 8.15 (s, 1H), 7.49-7.41 (m, 3H), 7.34-7.32 (m, 2H), 6.73 (d, 1H), 3.75 (s, 3H), 3.62-3.53 (m, 4H), 3.22-3.15 (m, 1H), 2.85-2.77 (m, 4H), 2.73-2.67 (m, 1H), 2.42-2.28 (m, 2H), 1.80-1.71 (m, 1H), 1.66-1.56 (m, 2H), 1.25-1.15 (m, 1H); LCMS (APCI+) m/z 475.2 (M + H)+ |
| 27 | 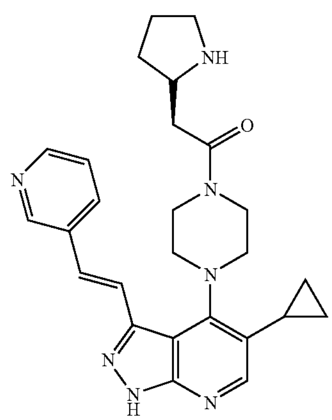 | (S,E)-1-(4-(5-cyclopropyl-3-(2-(pyridin-3-yl)vinyl)-1H-pyrazolo[3,4-b]pyridin-4-yl)piperazin-1-yl)-2-(pyrrolidin-2-yl)ethanone hydrochloride | $^1$H NMR (400 MHz, d$_6$-DMSO) δ 9.23-9.07 (m, 3H), 8.75 (d, 2H), 8.27 (s, 1H), 8.03-7.96 (m, 1H), 7.94 (d, 1H), 7.56 (d, 1H), 3.80-3.66 (m, 7H), 3.63-3.53 (m, 2H), 3.18-3.10 (m, 2H), .0-2.93 (m, 2H), 2.15-2.06 (m, 2H), 1.98-1.76 (m, 2H), 1.65-1.55 (m, 1H), 1.04-0.98 (m, 2H), 0.83-0.77 (m, 2H); LCMS (APCI+) m/z 389.2 (M + H)+ |
| 28 | 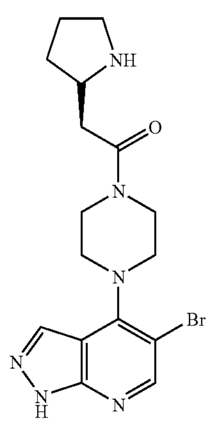 | (S)-1-(4-(5-bromo-1H-pyrazolo[3,4-b]pyridin-4-yl)piperazin-1-yl)-2-(pyrrolidin-2-yl)ethanone hydrochloride | $^1$H NMR (400 MHz, d$_6$-DMSO) δ 9.10 (br s, 1H), 8.90 (br s, 1H), 8.43 (s, 1H), 8.31 (s, 1H), 3.81-3.69 (m, 3H), 3.68-3.59 (m, 4H), 3.58-3.54 (m, 2H), 3.16-3.11 (m, 2H), 2.99-2.94 (m, 2H), 2.17-2.08 (m, 1H), 1.97-1.79 (m, 2H), 1.66-1.56 (m, 1H); LCMS (APCI+) m/z 325.9 (M + H)+ |

TABLE 1-continued

| Ex # | Structure | Name | NMR/LCMS |
|---|---|---|---|
| 29 | 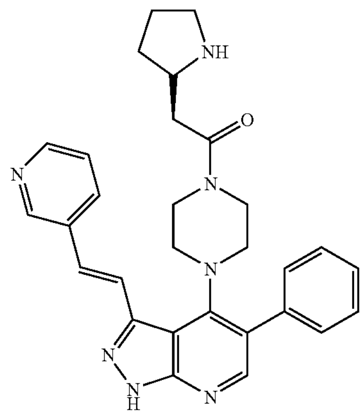 | (S,E)-1-(4-(5-phenyl-3-(2-(pyridin-3-yl)vinyl)-1H-pyrazolo[3,4-b]pyridin-4-yl)piperazin-1-yl)-2-(pyrrolidin-2-yl)ethanone hydrochloride | $^1$H NMR (400 MHz, d$_6$-DMSO) δ 9.19 (s, 1H), 9.09-9.01 (br s, 2H), 8.82-8.75 (m, 2H), 8.15 (s, 1H), 8.05-8.0 (m, 2H), 7.90 (d, 1H), 7.62 (d, 1H), 7.51-7.44 (m, 3H), 7.41-7.35 (m, 2H), 3.72-3.62 (m, 1H), 3.59-3.43 (m, 4H), 3.14-3.05 (m, 3H), 3.03-2.85 (m, 3H), 2.81 (d, 2H), 2.10-2.0 (m, 1H), 1.95-1.73 (m, 2H), 1.56-1.47 (m, 1H); LCMS (APCI+) m/z 425.2 (M + H)+ |
| 30 | 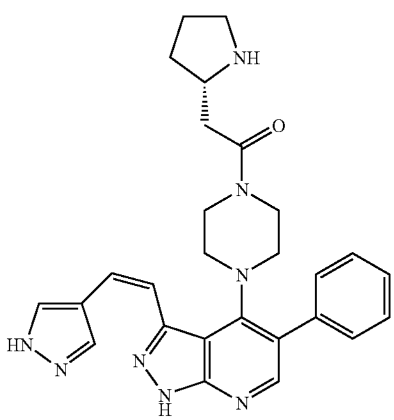 [SMILES: O=C(C[C@@H]1CCCN1)N1CCN(c2c(-c3ccccc3)cnc3[nH]nc(/C=C\c4cn[nH]c4)c23)CC1] | (S,Z)-1-(4-(3-(2-(1H-pyrazol-4-yl)vinyl)-5-phenyl-1H-pyrazolo[3,4-b]pyridin-4-yl)piperazin-1-yl)-2-(pyrrolidin-2-yl)ethanone hydrochloride | LCMS (APCI+) m/z 483 (M + H)+ |
| 31 | 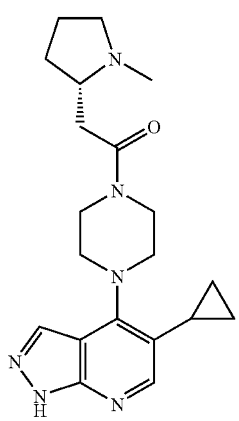 [SMILES: CN1CCC[C@H]1CC(=O)N1CCN(c2c(C3CC3)cnc3[nH]ncc23)CC1] | (S)-1-(4-(5-cyclopropyl-1H-pyrazolo[3,4-b]pyridin-4-yl)piperazin-1-yl)-2-(1-methylpyrrolidin-2-yl)ethanone hydrochloride | LCMS (APCI+) m/z 369 (M + H)+ |

TABLE 1-continued

| Ex # | Structure | Name | NMR/LCMS |
|---|---|---|---|
| 32 | 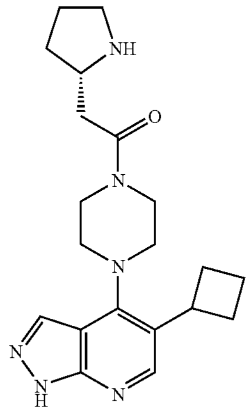 [SMILES: O=C(C[C@@H]1CCCN1)N1CCN(c2c(C3CCC3)cnc3[nH]ncc23)CC1] | (S)-1-(4-(5-cyclobutyl-1H-pyrazolo[3,4-b]pyridin-4-yl)piperazin-1-yl)-2-(pyrrolidin-2-yl)ethanone hydrochloride | $^1$H NMR (400 MHz, D$_2$O) δ 8.42 (s, 1H), 8.13 (s, 1H), 3.63-3.81 (m, 9 H), 3.58 (m, 1H), 3.18 (m, 2H), 2.97 (m, 1H), 2.78 (m, 1H), 2.25 (m, 2H), 2.15 (m, 1H), 1.80-1.98 (m, 5H), 1.72 (m, 1H), 1.62 (m, 1H); LCMS (APCI+) m/z 369 (M + H)+ |
| 33 | 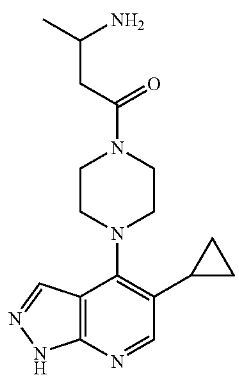 [SMILES: CC(N)CC(=O)N1CCN(c2c(C3CC3)cnc3[nH]ncc23)CC1] | 3-amino-1-(4-(5-cyclopropyl-1H-pyrazolo[3,4-b]pyridin-4-yl)piperazin-1-yl)butan-1-one hydrochloride | $^1$H NMR (400 MHz, d$_6$-DMSO) δ 8.17 (br s, 1H), 8.05 (br s, 1H), 4.10-3.90 (m, 3H), 3.85-3.73 (m, 4H), 3.58-3.55 (m, 1H), 2.76 (d, 2H), 2.09-2.00 (m, 1H), 1.27 (d, 3H), 1.04-0.98 (m, 2H), 0.77-0.72 (m, 2H); m/z (APCI pos) 329.1 (M + H) |
| 34 | 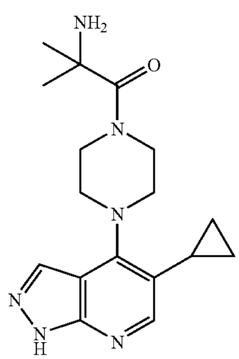 [SMILES: CC(C)(N)C(=O)N1CCN(c2c(C3CC3)cnc3[nH]ncc23)CC1] | 2-amino-1-(4-(5-cyclopropyl-1H-pyrazolo[3,4-b]pyridin-4-yl)piperazin-1-yl)-2-methylpropan-1-one hydrochloride | $^1$H NMR (400 MHz, d$_6$-DMSO) δ 8.39 (br s, 2H), 8.19 (br s, 1H), 4.10-4.00 (m, 4H), 3.90-3.85 (m, 4H), 3.17(s, 1H), 2.05-1.98 (m, 1H), 1.64 (d, 6H), 1.06-0.99 (m, 2H), 0.77-0.72 (m, 2H); m/z (APCI pos) 329.1 (M + H) |
| 35 | 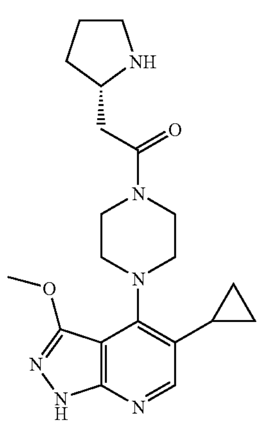 [SMILES: COc1n[nH]c2ncc(C3CC3)c(N3CCN(C(=O)C[C@@H]4CCCN4)CC3)c12] | (S)-1-(4-(5-cyclopropyl-3-methoxy-1H-pyrazolo[3,4-b]pyridin-4-yl)piperazin-1-yl)-2-(pyrrolidin-2-yl)ethanone hydrochloride | $^1$H NMR (400 MHz, D$_2$O) δ 7.89 (s, 1H), 3.95 (s, 3H), 3.82-3.72 (m, 5H), 3.65-3.60 (m, 4H), 3.22-3.17 (m, 2H), 3.05-2.95 (m, 1H), 2.82-2.62 (m, 2H), 2.19-2.03 (m, 1H), 2.00-1.78 (m, 3H), 1.68-1.51 (m, 1H), 0.95-0.92 (m, 2H), 0.58-0.52 (m, 2H); LCMS (APCI+) m/z 385 (M + H)+ |

TABLE 1-continued

| Ex # | Structure | Name | NMR/LCMS |
|---|---|---|---|
| 36 | 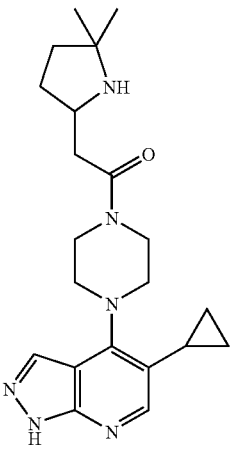 [SMILES: CC1(C)CCC(CC(=O)N2CCN(c3c(C4CC4)cnc4[nH]ncc34)CC2)N1] | 1-(4-(5-cyclopropyl-1H-pyrazolo[3,4-b]pyridin-4-yl)piperazin-1-yl)-2-(5,5-dimethylpyrrolidin-2-yl)ethanone hydrochloride | $^1$H NMR (400 MHz, D$_2$O) δ 8.38 (s, 1H), 8.03 (s, 1H), 4.02-3.92 (m, 5H), 3.79-3.67 (m, 4H), 2.99-2.81 (m, 2H), 2.28-2.17 (m, 1H), 1.92-1.75 (m, 4H), 1.35-1.33 (d, 6H), 0.92-0.90 (m, 2H), 0.60-0.58 (m, 2H); LCMS (APCI+) m/z 383 (M + H)+ |
| 37 | 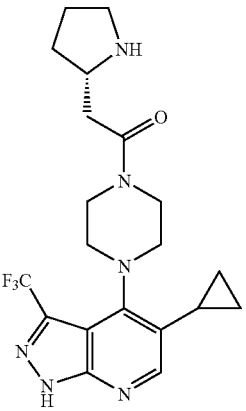 [SMILES: O=C(C[C@@H]1CCCN1)N1CCN(c2c(C3CC3)cnc3[nH]nc(C(F)(F)F)c23)CC1] | (S)-1-(4-(5-cyclopropyl-3-(trifluoromethyl)-1H-pyrazolo[3,4-b]pyridin-4-yl)piperazin-1-yl)-2-(pyrrolidin-2-yl)ethanone hydrochloride | $^1$H NMR (400 MHz, D$_2$O) δ 8.10 (s, 1H), 3.85-3.76 (m, 1H), 3.61-3.50 (m, 4H), 3.42-3.30 (m, 4H), 3.22-3.11 (m, 2H), 3.00-2.92 (m, 1H), 2.82-2.74 (m, 1H), 2.20-2.05 (m, 1H), 1.99-1.80 (m, 3H), 1.68-1.54 (m, 1H), 0.95-0.90 (m, 2H), 0.65-0.60 (m, 2H); LCMS (APCI+) m/z 423 (M + H)+ |
| 38 | 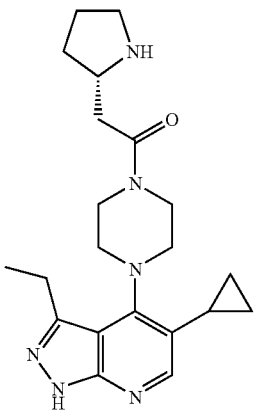 | (S)-1-(4-(5-cyclopropyl-3-ethyl-1H-pyrazolo[3,4-b]pyridin-4-yl)piperazin-1-yl)-2-(pyrrolidin-2-yl)ethanone hydrochloride | $^1$H NMR (400 MHz, D$_2$O) δ 8.11 (s, 1H), 3.88-3.79 (m, 5H), 3.70-3.61 (m, 4H), 3.22-3.17 (m, 2H), 3.05-2.95 (m, 3H), 2.82-2.78 (m, 1H), 2.20-2.10 (m, 1H), 2.00-1.81 (m, 3H), 1.65-1.57 (m, 1H), 1.19 (t, 3H), 0.96-0.92 (m, 2H), 0.69-0.60 (m, 2H); LCMS (APCI+) m/z 383 (M + H)+ |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:
1. A compound selected from Formula I:

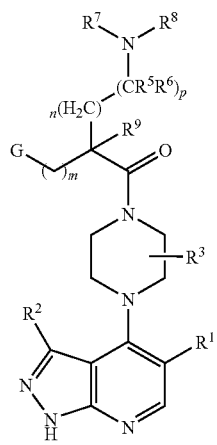

and stereoisomers and pharmaceutically acceptable salts thereof, wherein:
G is phenyl optionally substituted by 1-3 independent $R^4$ groups,
or when m is 0, G may additionally be absent or $C_1$-$C_4$ alkyl;
$R^1$ is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;
$R^2$ is selected from hydrogen, $CH_3$, $CH_2CH_3$, $CF_3$, $C_2$-$C_4$ alkenyl optionally substituted with one or two $R^c$ groups, $NHR^a$ or —$OR^f$, provided that when $R^1$ is hydrogen, then $R^2$ is —$OR^f$;
$R^3$ is selected from hydrogen or $C_1$-$C_4$ alkyl;
$R^4$ is selected from halogen, $CF_3$, $OCF_3$ and CN;
$R^5$ and $R^6$ are independently selected from hydrogen or $CH_3$;
$R^7$ and $R^8$ are independently selected from hydrogen or $C_1$-$C_6$ alkyl;
$R^9$ is hydrogen or $CH_3$;
$R^a$ is hydrogen or a five to six membered heterocycle optionally substituted with an oxo group;
$R^b$ is halogen;
$R^c$ is OH, $OCH_3$, oxo, or a 5 to 6 membered heteroaryl;
$R^e$ is $C_1$-$C_4$ alkyl optionally substituted with OH or a 5-6 membered heterocycle;
$R^f$ is $C_1$-$C_4$ alkyl optionally substituted with one or more OH groups;

m, n and p are independently 0 or 1;
or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl), such that the compound of Formula I has the structure of Formula II:

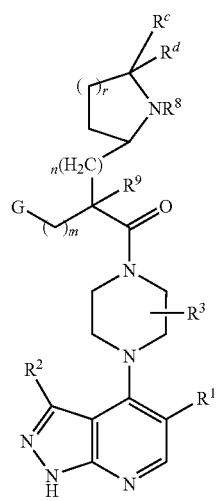

wherein $R^c$ and $R^d$ are independently selected from hydrogen or $C_1$-$C_4$ alkyl; and
r is 1 or 2.
2. A compound of claim 1 selected from Formula I:

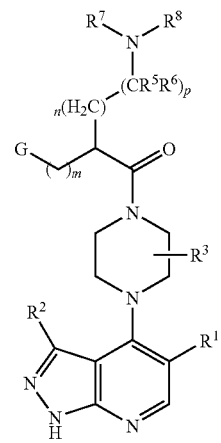

and stereoisomers and pharmaceutically acceptable salts thereof, wherein:
G is phenyl optionally substituted by 1-3 independent $R^4$ groups,
or when m is 0, G may additionally be absent or $C_1$-$C_4$ alkyl;
$R^1$ is selected from hydrogen, halogen, CN, $C_1$-$C_4$ alkyl optionally substituted with halogen, —$OR^e$, $C_3$-$C_6$ cycloalkyl, 5 or 6 membered heteroaryl, phenyl or —O-phenyl, wherein the heteroaryl, phenyl or —O-phenyl may be optionally substituted with one or two $R^b$ groups;

$R^2$ is selected from hydrogen, $CH_3$ or $-OR^f$, provided that when $R^1$ is hydrogen, then $R^2$ is $-OR^f$;
$R^3$ is selected from hydrogen or $C_1$-$C_4$ alkyl;
$R^4$ is selected from halogen, $CF_3$, $OCF_3$ and CN;
$R^5$ and $R^6$ are independently selected from hydrogen or $CH_3$;
$R^7$ and $R^8$ are independently selected from hydrogen or $C_1$-$C_6$ alkyl;
$R^b$ is halogen;
$R^e$ is $C_1$-$C_4$ alkyl optionally substituted with OH or a 5-6 membered heterocycle;
$R^f$ is $C_1$-$C_4$ alkyl optionally substituted with one or more OH groups;
m, n and p are independently 0 or 1;
or $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or $O(C_1$-$C_3$ alkyl), such that the compound of Formula I has the structure of Formula II:

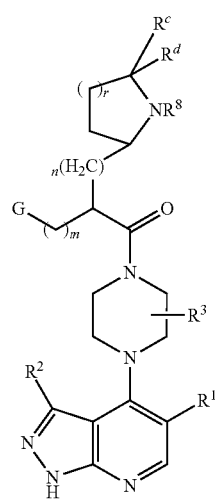

wherein $R^c$ and $R^d$ are independently selected from hydrogen or $C_1$-$C_4$ alkyl; and
r is 1 or 2.
3. A compound of claim 1, wherein $R^1$ is CN.
4. A compound of claim 1, wherein $R^1$ is $C_1$-$C_4$ alkyl optionally substituted with halogen.
5. A compound of claim 4, wherein $R^1$ is methyl.
6. A compound of claim 4, wherein $R^1$ is $CF_3$.
7. A compound of claim 1, wherein $R^1$ is $C_3$-$C_6$ cycloalkyl.
8. A compound of claim 7, wherein $R^1$ is cyclopropyl.
9. A compound of claim 1, wherein $R^1$ is phenyl optionally substituted with one or two $R^b$ groups.
10. A compound of claim 9, wherein $R^1$ is phenyl.
11. A compound of claim 9, wherein $R^1$ is 3-fluorophenyl.
12. A compound of claim 1, wherein $R^1$ is —O-phenyl, optionally substituted with one or two $R^b$ groups.
13. A compound of claim 12, wherein $R^1$ is 3-fluorophenoxy.
14. A compound of claim 1, wherein $R^1$ is halogen.
15. A compound of claim 14, wherein $R^1$ is selected from Cl and Br.
16. A compound of claim 1, wherein $R^1$ is hydrogen.
17. A compound claim 1, wherein $R^2$ is hydrogen.
18. A compound of claim 1, wherein $R^2$ is —$OR^f$.
19. A compound of claim 18, wherein $R^2$ is selected from —$OCH_3$, —$OCH_2CH_2OH$ and —$OCH_2CH(OH)CH_2OH$.
20. A compound of claim 1, wherein $R^7$ is hydrogen.
21. A compound of claim 1, wherein $R^7$ is isopropyl.
22. A compound of claim 1, wherein $R^8$ is hydrogen.
23. A compound of claim 1, wherein p is 1.
24. A compound of claim 1, wherein $R^5$ is hydrogen.
25. A compound of claim 1, wherein $R^6$ is hydrogen.
26. A compound of claim 1, wherein p is 0.
27. A compound of claim 1, wherein $R^3$ is hydrogen.
28. A compound of claim 1, wherein n is 0.
29. A compound of claim 1, wherein n is 1.
30. A compound of claim 1, wherein m is 1.
31. A compound of claim 1, wherein m is 0.
32. A compound of claim 1, wherein G is phenyl optionally substituted by one to three $R^4$ groups.
33. A compound of claim 32, wherein G is 4-chlorophenyl.
34. A compound of claim 31, wherein G is absent or $C_1$-$C_4$ alkyl.
35. A compound of claim 34, wherein G is absent.
36. A compound as claimed in claim 31, wherein m is 0 and G is $G^1$, having the structure of Formula V:

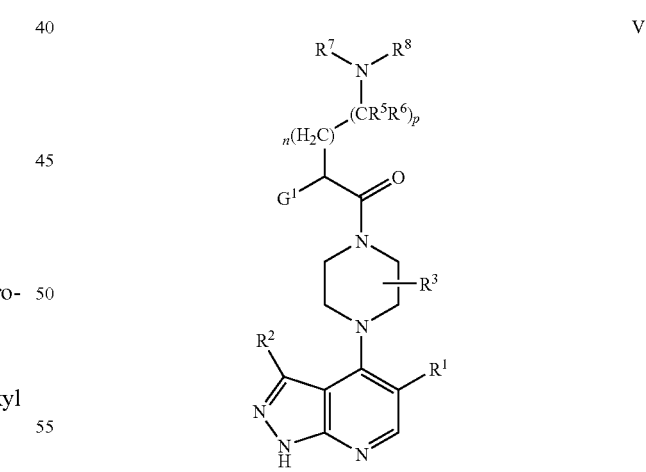

wherein $G^1$ is absent or $C_1$-$C_4$ alkyl.
37. A compound of claim 36, wherein G is absent.
38. A compound of claim 1, wherein $R^5$ is hydrogen, $R^6$ and $R^7$ together with the atoms to which they are attached form an optionally substituted 5-6 membered heterocyclic ring having one ring nitrogen atom, and $R^8$ is selected from the group consisting of hydrogen or $C_1$-$C_4$ alkyl optionally substituted with OH or O($C_1$-$C_3$ alkyl), having the Formula II:

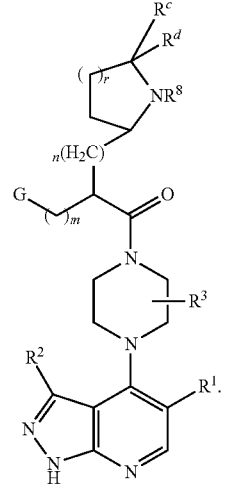

39. A compound of claim 38, wherein r is 1.
40. A compound of claim 38, wherein r is 2.
41. A compound of claim 38, wherein $R^c$ is hydrogen.
42. A compound of claim 38, wherein $R^c$ is methyl.
43. A compound of claim 38, wherein $R^d$ is hydrogen.
44. A compound of claim 38, wherein $R^d$ is methyl.
45. A compound of claim 38, wherein $R^8$ is hydrogen.
46. A compound as claimed in claim 1, wherein $R^1$ is I.
47. A compound as claimed in claim 1, wherein $R^2$ is selected from $CH_3$, $CH_2CH_3$ and $CF_3$.
48. A compound as claimed in claim 1, wherein $R^2$ is selected from —CH=CHC(=O)OCH$_3$, 2-(pyridin-3-yl)vinyl, and 2-(1H-pyrazol-4-yl)vinyl.
49. A compound as claimed in claim 1, wherein $R^2$ is selected from $NH_2$ and NH-4-pyrrolidin-2-one.
50. A compound of claim 1, wherein $R^9$ is hydrogen.
51. A compound as claimed in claim 1, wherein $R^9$ is $CH_3$.
52. A compound of Formula I as defined in claim 1 and having the structure:

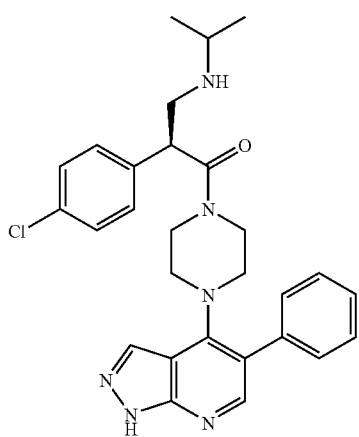

-continued

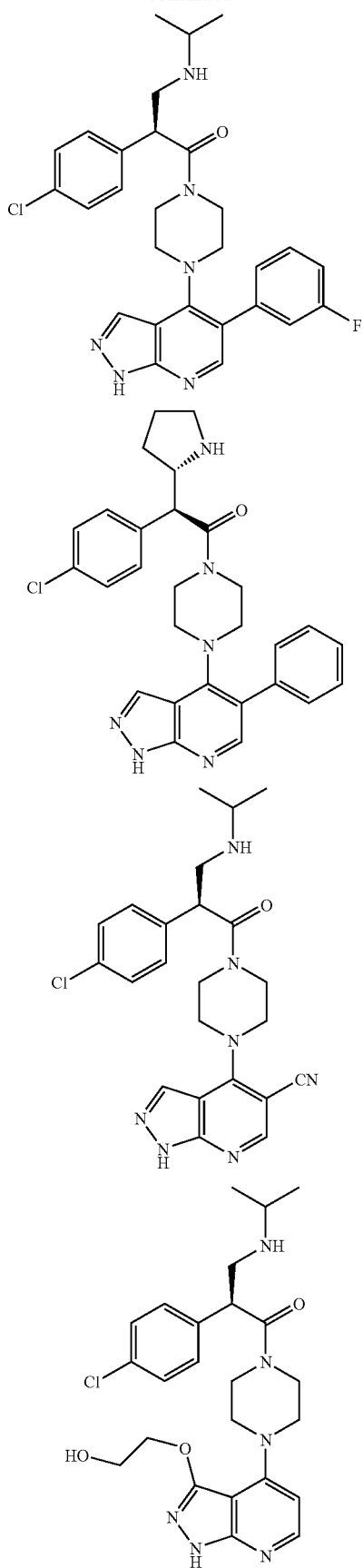

107
-continued
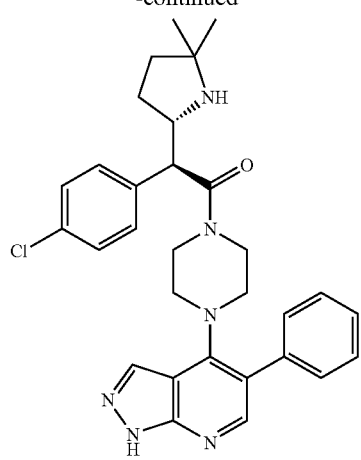
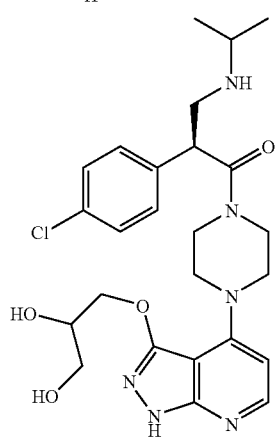
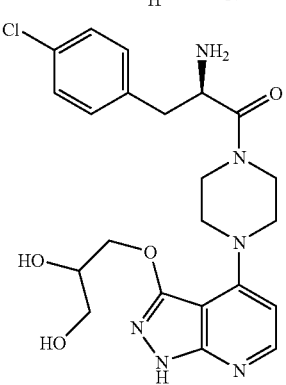
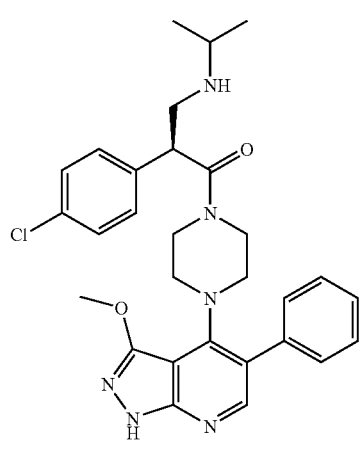
108
-continued
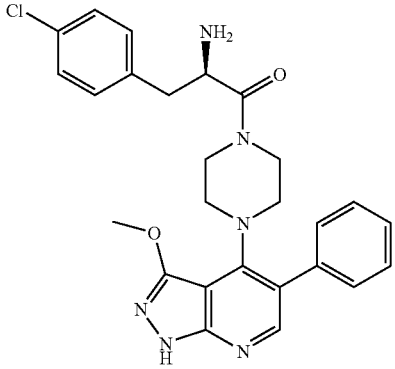
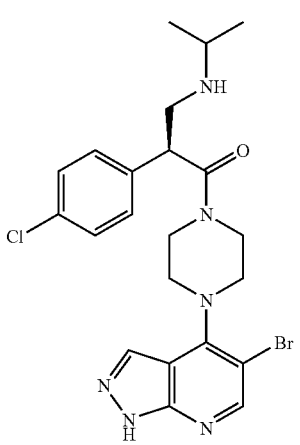
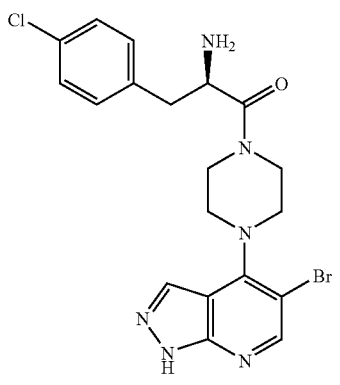
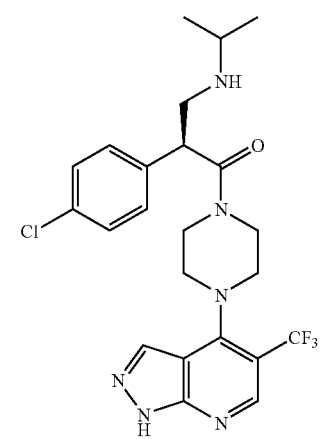

109
-continued
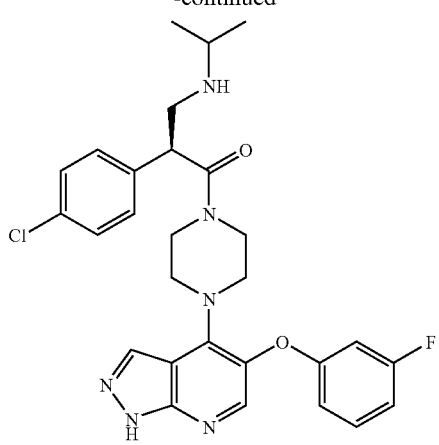
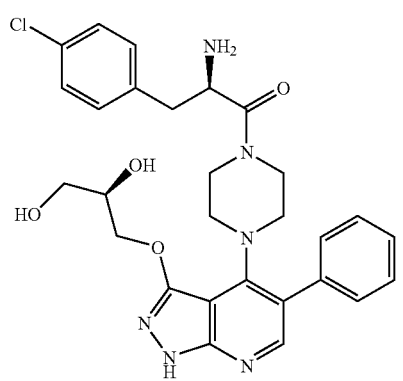
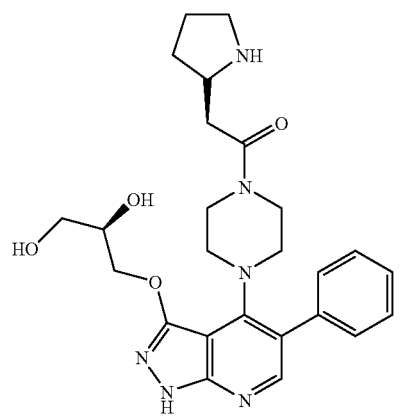
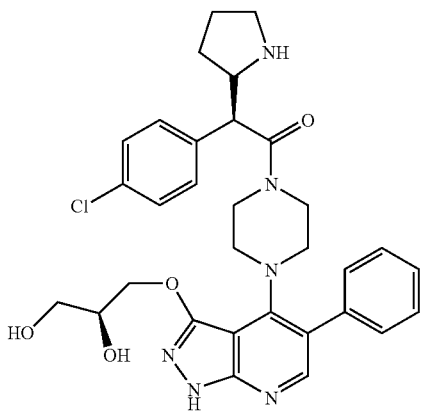
110
-continued
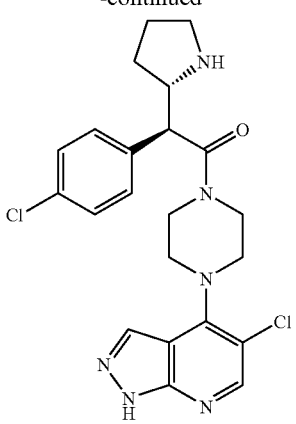
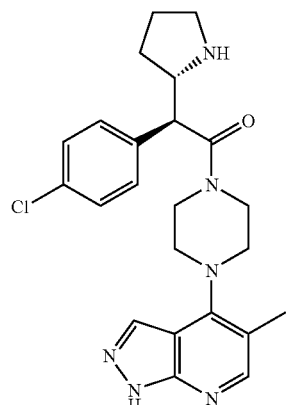
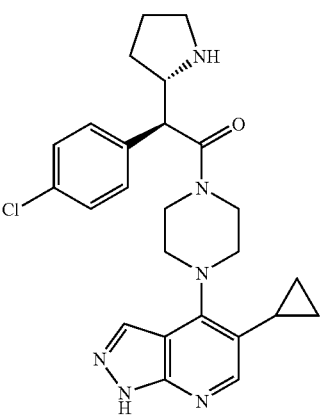
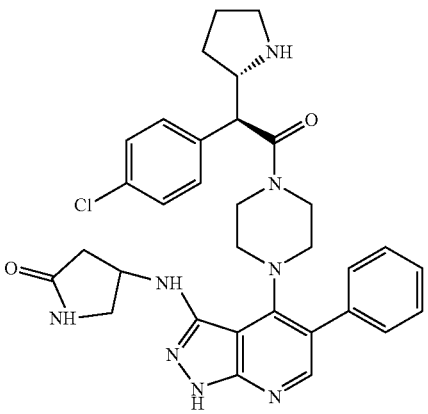

111
-continued
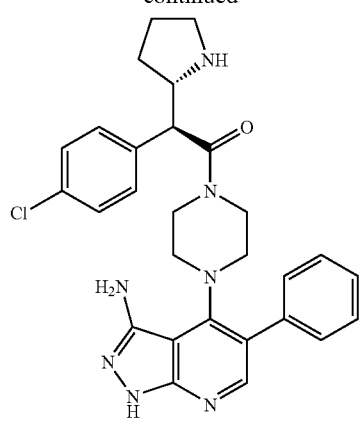
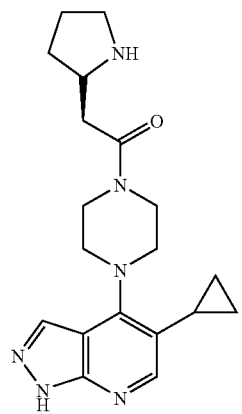
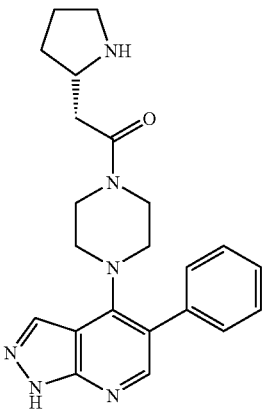
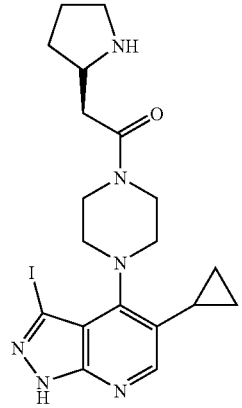
112
-continued
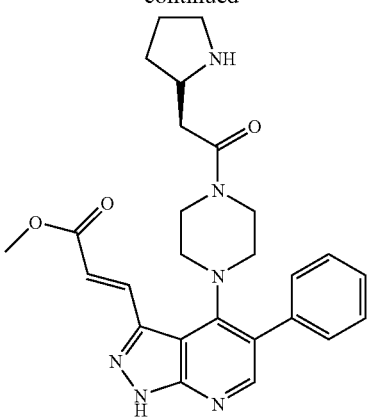
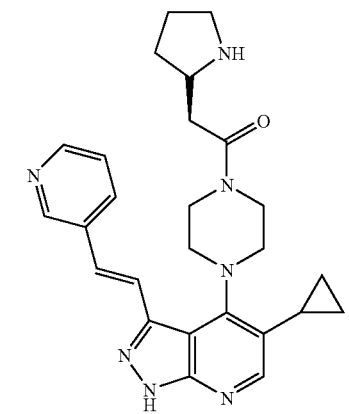
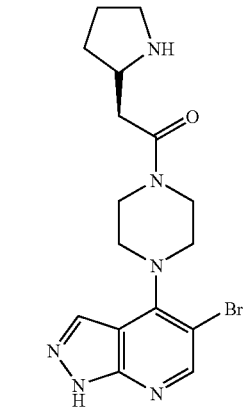
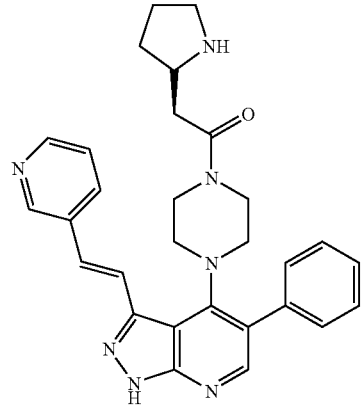

113
-continued
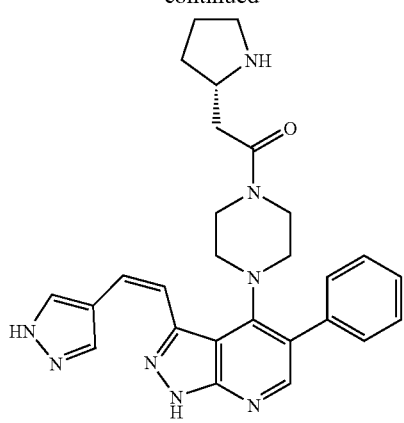
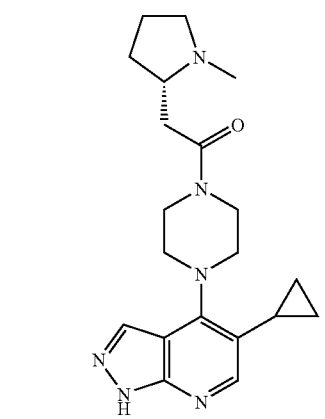
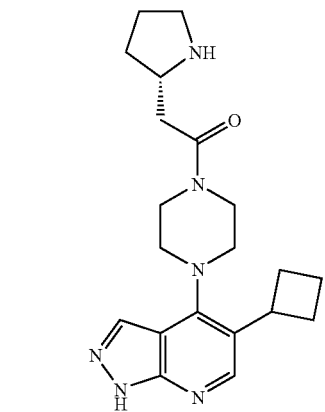
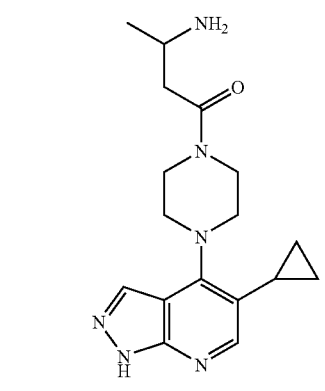
114
-continued
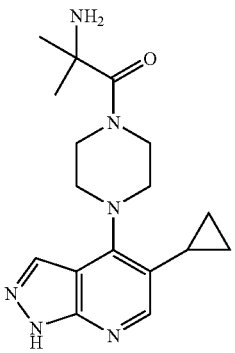
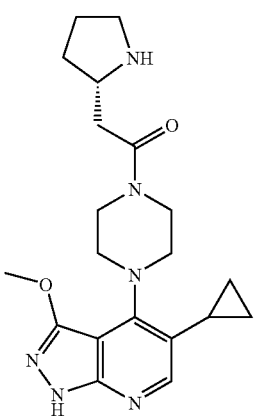
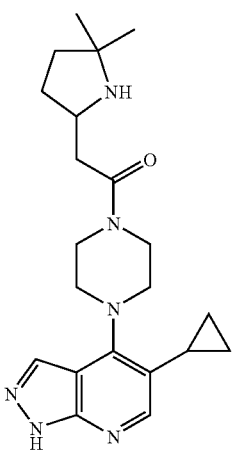

115
-continued
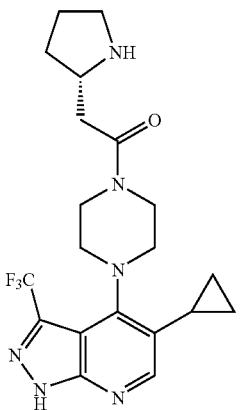
116
-continued
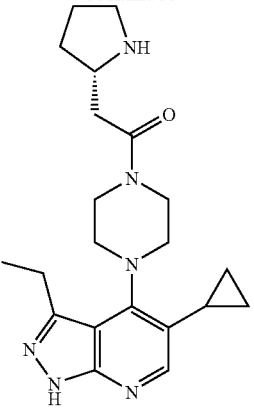 [SMILES: CCc1n[nH]c2ncc(C3CC3)c(N3CCN(C(=O)C[C@@H]4CCCN4)CC3)c12]
or a pharmaceutically acceptable salt thereof.
53. A pharmaceutical composition comprising a compound of claim 1, and a pharmaceutically acceptable carrier or excipient.
* * * * *